(12) United States Patent
Brown et al.

(10) Patent No.: US 9,914,909 B2
(45) Date of Patent: Mar. 13, 2018

(54) COSTIMULATORY CHIMERIC ANTIGEN RECEPTOR T CELLS TARGETING IL13Rα2

(71) Applicant: City of Hope, Duarte, CA (US)

(72) Inventors: Christine E. Brown, Duarte, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 15/167,869

(22) Filed: May 27, 2016

(65) Prior Publication Data

US 2016/0340649 A1 Nov. 24, 2016

Related U.S. Application Data

(63) Continuation of application No. PCT/US2015/051089, filed on Sep. 18, 2015.

(60) Provisional application No. 62/053,068, filed on Sep. 19, 2014.

(51) Int. Cl.
| | | |
|---|---|---|
| C12N 5/0783 | (2010.01) | |
| C07K 14/54 | (2006.01) | |
| C07K 14/715 | (2006.01) | |
| A61K 35/17 | (2015.01) | |
| C07K 14/725 | (2006.01) | |
| C07K 14/73 | (2006.01) | |
| C07K 14/705 | (2006.01) | |
| A61K 38/00 | (2006.01) | |

(52) U.S. Cl.
CPC ............ *C12N 5/0636* (2013.01); *A61K 35/17* (2013.01); *C07K 14/5437* (2013.01); *C07K 14/7051* (2013.01); *C07K 14/70514* (2013.01); *C07K 14/70578* (2013.01); *C07K 14/7155* (2013.01); *A61K 38/00* (2013.01); *C07K 2319/03* (2013.01); *C07K 2319/30* (2013.01); *C07K 2319/33* (2013.01); *C07K 2319/74* (2013.01); *C07K 2319/75* (2013.01); *C12N 2510/00* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 5,359,046 A | 10/1994 | Capon et al. | |
| 5,686,281 A | 11/1997 | Roberts | |
| 6,410,319 B1 | 6/2002 | Raubitschek et al. | |
| 7,070,995 B2 | 7/2006 | Jensen | |
| 7,446,190 B2 | 11/2008 | Sadelain et al. | |
| 7,514,537 B2 | 4/2009 | Jensen et al. | |
| 8,324,353 B2 | 12/2012 | Jensen | |
| 8,497,118 B2 | 7/2013 | Jensen | |
| 8,822,647 B2 * | 9/2014 | Jensen | A61K 48/005 424/93.21 |
| 9,217,025 B2 | 12/2015 | Jensen | |
| 2002/0164794 A1 | 11/2002 | Wernet | |
| 2003/0077249 A1 | 4/2003 | Bebbington et al. | |
| 2003/0171546 A1 | 9/2003 | Jensen | |
| 2005/0113564 A1 | 5/2005 | Campana et al. | |
| 2006/0067920 A1 | 3/2006 | Jensen | |
| 2007/0009469 A1 | 1/2007 | Kleinman et al. | |
| 2009/0257994 A1 | 10/2009 | Jensen | |
| 2012/0148552 A1 * | 6/2012 | Jensen | A61K 48/005 424/93.71 |
| 2013/0287748 A1 * | 10/2013 | June | A61K 35/17 424/93.21 |
| 2016/0175398 A1 | 6/2016 | Jensen | |

FOREIGN PATENT DOCUMENTS

| | | |
|---|---|---|
| CA | 2445746 | 11/2002 |
| JP | 2006-528848 | 9/2004 |
| WO | WO 2000/023573 | 10/1999 |
| WO | WO 2002/088334 | 11/2002 |
| WO | WO 2007/059298 | 5/2007 |
| WO | WO 2008/095141 | 8/2008 |
| WO | WO2010025177 | * 3/2010 |
| WO | WO 2010/065818 | 6/2010 |
| WO | WO201207900 | * 6/2012 |

OTHER PUBLICATIONS

"Protein Expression," Chapter 16 in Current Protocols in Molecular Biology (2007), published by John Wiley & Sons, pp. 16.0.1-16.25.24; 329 pages.

Ahmed et al., "HER2-specific T cells target primary glioblastoma stem cells and induce regression of autologous experimental tumors," Clin. Cancer Res., 2010, 16(2): 474-85.

Altenschmidt et al., "Cytolysis of Tumor Cells Expressing in the NEU/ERBB-2, ERBB-3, and ERBB-4 Receptors by Genetically Targeted Naïve T Lymphocytes," Clinical Cancer Research, The American Association for Cancer Research, vol. 2, No. 6, Jun. 1996, 1001-1008.

Ashkenazi et al., "Immunoadhesins: An Alternative to Human Monoclonal Antibodies," 1995, Methods: a Companion to Methods in Enzymology, 8: 104-115.

(Continued)

*Primary Examiner* — Lei Yao
(74) *Attorney, Agent, or Firm* — Fish & Richardson P.C.

(57) ABSTRACT

Chimeric transmembrane immunoreceptors (CAR) which include an extracellular domain that includes IL-13 or a variant thereof that binds interleukin-13Rα2 (IL13Rα2), a transmembrane region, a costimulatory domain and an intracellular signaling domain are described.

16 Claims, 42 Drawing Sheets

(56) References Cited

OTHER PUBLICATIONS

Bailey et al., "Molecular Genetics and Control Systems," Biochemical Engineering Fundamentals, 2d Ed., 1986, 349-357.
Bonnerot et al., "Intracellular signaling and endosomal trafficking of immunoreceptors shared effectors underlying MHC class II-restricted antigen presentation," 1997, Immunology Letters, 47: 1-4.
Brown et al., "Recognition and killing of brain tumor stem-like initiating cells by CD8+ cytolytic T cells," Cancer Res., 2009, 69(23): 8886-93.
Brown et al., "Stem-like tumor-initiating cells isolated from IL13Ra2 expressing gliomas are targeted and killed by IL13-zetakine-redirected T Cells," Clin. Cancer Res., 2012, 18(8): 2199-209.
Brown et al., "Tumor-derived chemokine MCP-1/CCL2 is sufficient for mediating tumor tropism of adoptively transferred T cells," J. Immunol., 2007, 179(5): 3332-41.
Campbell et al., "Totipotency or Multipotentially of Cultured Cells: Applications and Progress," 1997, Theriology, 47(1): 63-72.
Cartellieri et al., "Chimeric antigen receptor-engineered T cells for immunotherapy of cancer," J. Biomed. Biotechnol., 2010: 956304.
Chang et al., "Abstracts for the 21$^{st}$ Annual Scientific Meeting of the International Society for Biological Therapy of Cancer," 2006, Journal of Immunotherapy, 29(6): 628.
Chang et al., "Transgene-enforced co-stimulation of CD4+ T cells leads to enhanced and sustained anti-tumor effector functioning," 2007, Cytotherapy, 9(8): 771-781.
Chow et al., "T cells redirected to EphA2 for the immunotherapy of glioblastoma," Mol. Ther., 2013, 21(3): 629-37.
Debinski and Thompson, "Retargeting interleukin 13 for radioimmunodetection and radioimmunotherapy of human high-grade gliomas," Clin. Cancer Res., 1999, 5(10 Suppl): 3143s-3147s.
Debinski et al., "Human glioma cells overexpress receptors for interleukin 13 and are extremely sensitive to a novel chimeric protein composed of interleukin 13 and pseudomonas exotonin," Clinical Cancer Research, 1995, 1: 1253-1258.
Debinski et al., "Novel anti-brain tumor cytotoxins specific for cancer cells," Nature Biotechnology, 1998, 16: 449-453.
Debinski et al., "Novel way to increase targeting specificity to a human glioblastoma-associated receptor for interleukin 13," Int. J. Cancer, 1998, 76: 547-551.
Debinski et al., "Receptor for interleukin 13 is a marker and therapeutic target for human high-grade gliomas," Clinical Cancer Research, 1999, 5: 985-990.
Debinski et al., "Receptor for interleukin 13 is abundantly and specifically over-expressed in patients with glioblastoma multiforme," Int. J. Oncology, 1999, 15: 481-486.
Debinski, "Expression of a restrictive receptor for interleukin 13 is associated with glial transformation," J. Neuro-Oncology, 2000, 48: 103-111.
Edelman et al., "The covalent structure of an entire GammaG immunoglobulin molecule," Proc. Natl. Acad. Sci. USA, 1969, 63(1): 78-85.
Ehtesham et al., "Recent Progress in Immunotherapy for Malignant Glioma: Treatment Strategies and Results From Clinical Trials," 2004, Cancer Control. 11(3): 192-207.
Finney, "Activation of Resting Human Primary T Cells with Chimeric Receptors: Costimulation from CD28, Inducible Costimulator, CD134, and CD137 in Series with Signals from the TCR, Chain," Journal of Immunology, 2004, 172: 104-113.
Finney, "Chimeric Receptors Providing Both Primary and Costimulatory Signaling in T Cells from a Single Gene Product," Journal of Immunology, 1998, 161: 2791-2797.
Glick et al., "Manipulation of Gene Expression in Prokaryotes," Molecular Biotechnology, 2d Ed., Ch. 6, 1998, 109-143.
Hong et al., "Successful treatment of melanoma brain metastases with adoptive cell therapy," Clin. Cancer Res., 2010, 16(19): 4892-8.

International Preliminary Report on Patentability in International Application No. PCT/US2015/051089, dated Mar. 21, 2017, 8 pages.
International Search Report and Written Opinion in International Application No. PCT/US2015/051089, dated Jan. 29, 2016, 14 pages.
Jensen et al., "CD20 is a molecular target for scFvFc:zeta receptor redirected T cells: implications for cellular immunotherapy of CD20 malignancy," Biol. Blood Marrow Transplant, 1998, 4: 75-83.
Jonnalagadda et al., "Chimeric antigen receptors (CARs) incorporating mutations in the IgG4 Fc spacer region to eliminate Fc receptor recognition results in improved CAR T cell persistence and anti-tumor efficacy," Journal for Immunotherapy of Cancer, 2013, 1(1): 18.
Joshi et al., "Interleukin-13 receptor a Chain: A novel tumor-associated transmembrane protein in primary explants of human malignant gliomas," Cancer Research, 2000, 60: 1168-1172.
Kahlon et al., "Redirecting T lymphocyte antigen specificity via engineered zetakine immonoreceptors: development of a prototype construct specific for the tumor-restricted IL-13alpha2 receptor," Molecular Therapy, May 2001, 3(5): S374.
Kahlon et al., "Specific recognition and killing of glioblastoma multiforme by interleukin 13-zetakine redirected cytolytic T cells," Cancer Res., 2004, 64(24): 9160-6.
Kahlon et al., "The IL-13 zetakine chimeric immunoreceptor: a novel approach to genetically engineer T cells for glioma immunotherapy," Neuro-Oncology, 3(4): 315-316, Oct. 2001.
Kong et al., "Suppression of Human Glioma Xenografts with Second-Generation IL13R-Specific Chimeric Antigen Receptor-Modified T cells," Clinical Cancer Research, 2012, 18(21): 5949-5960.
Lazovic et al., "Imaging Immune Response In Vivo: Cytolytic Action of Genetically Altered T Cells Directed to Glioblastoma Multiforme," 2008, Clin. Cancer Res., 14(2): 3832-3839.
Liu et al., "Interleukin-13 sensitivity and receptor phenotypes of human glial cell lines: Non-neoplastic glia and low-grade astrocytoma differ from malignant glioma," Cancer Immunol. Immunother., 2000, 49: 319-324.
Melero et al., "Amplification of tumor immunity by gene transfer of the co-stimulatory 4-1BB ligand: synergy with the CD28 co-stimulatory pathway," Eur. J. Immunol., 1998, 28: 1116-1121.
Minty et al., "Interleukin-13 is a new human lymphokine regulating inflammatory and immune responses," Nature, 1993, 362: 248-250.
Mintz et al., "Cancer genetics/epigenetics and the X chromosome: Possible new links for malignant glioma pathogenesis and immune-based therapies," Crit. Rev. Oncol., 2000, 11(1): 77-95.
Moeller et al., "A functional role for CD28 costimulation in tumor recognition by single-chain receptor-modified T cells," 2004, Cancer Gene Therapy, 11: 371-379.
Murata et al., "Structure of IL-13 receptor: analysis of subunit composition in cancer and immune cells," Biochemical and Biophysical Research Communications, 1997, 238: 90-94.
Niederman et al., "Antitumor activity of cytotoxic T lympocute engineered to target vascular endothelial growth factor receptors," Proceedings of the National Academy of Sciences of USA, National Academy of Science, May 2002, 99(19): 7009-7014.
Obiri et al., "The IL-13 receptor structure differs on various cell types and may share more than one component with IL-4 receptor," J. Immunol., 1997, 158:756-764.
Sampson et al., "EGFRvIII mCAR-modified T-cell therapy cures mice with established intracerebral glioma and generates host immunity against tumor-antigen loss," Clin. Cancer Res., 2014, 20(4): 972-84.
Stastny et al., "Medulloblastomas Expressing IL13Ra2 are Targets for IL13-zetakine+ Cytolytic T Cells," J. Pediatr. Hematol. Oncol., 2007, 29: 669-677.
Thaci et al., "Significance of interleukin-13 receptor alpha 2-targeted glioblastoma therapy," Neuro-Oncology, 2014, 16(10): 1304-1312.
Thompson et al., "Mutants of interleukin 13 with altered reactivity toward interleukin 13 receptors," J. Biol. Chem., 1999, 274: 29944-29950.

(56) References Cited

OTHER PUBLICATIONS

Wang et al., "Optimizing Adoptive Polyclonal T Cell Immunotherapy of Lymphomas, Using a Chimeric T Cell Receptor Possessing CD28 and CD137 Costimulatory Domains," 2007, Human Gene Therapy, 18: 712-725.

Xu et al., "Targeting and therapy of carcinoembryonic antigen-expressing tumors in transgenic mice with an antibody-interleukin 2 fusion protein," Cancer Research, 2000, 60: 4475-4484.

Yaghoubi et al., "Noninvasive detection of therapeutic cytolytic T cells with 18F-FHBG PET in a patient with glioma," Nat. Clin. Pract. Oncol., 2009, 6(1): 53-8.

Yamasaki et al., "Specific adoptive immunotherapy of malignant glioma with long-term cytotoxic T lymphocyte line expanded in T-cell growth factor," Experimental Study and Future Prospects, Neurosurg. Rev., 1984, 7: 37-54.

\* cited by examiner

FIGURE 1
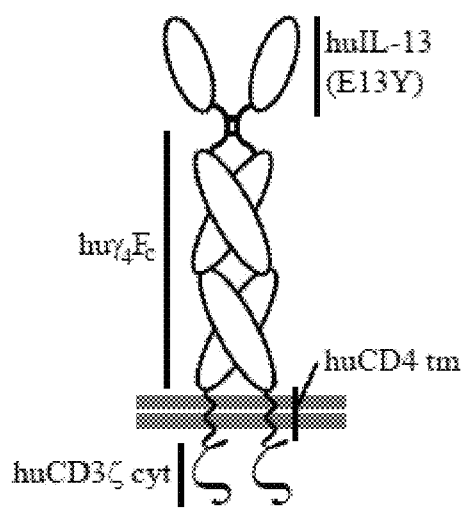
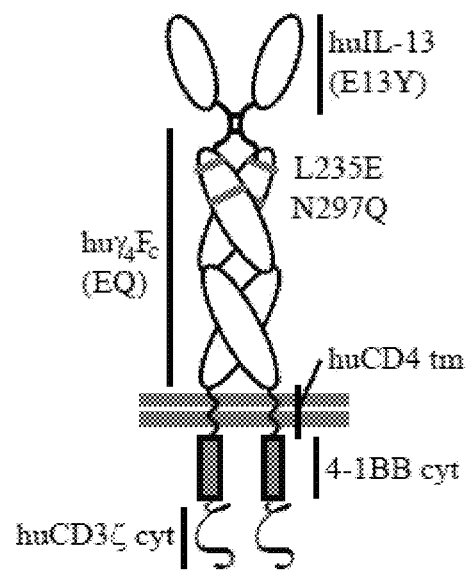

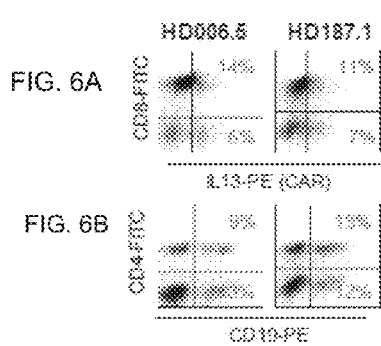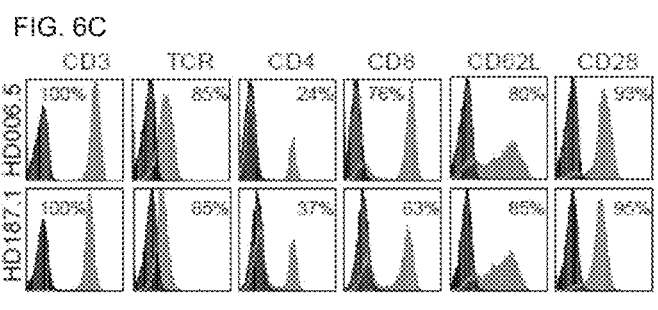

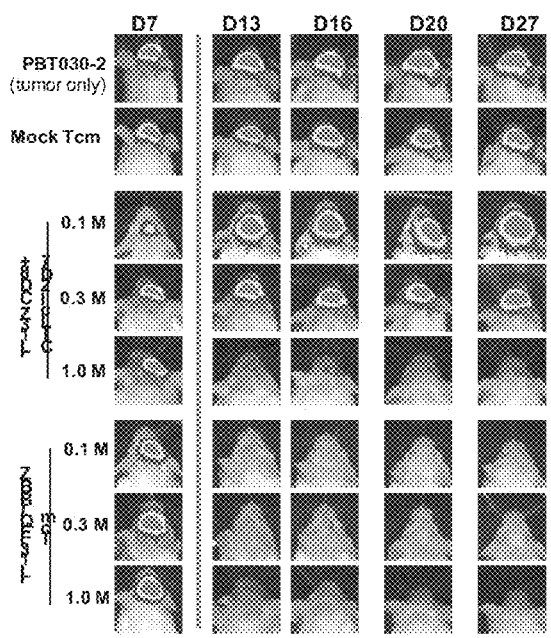
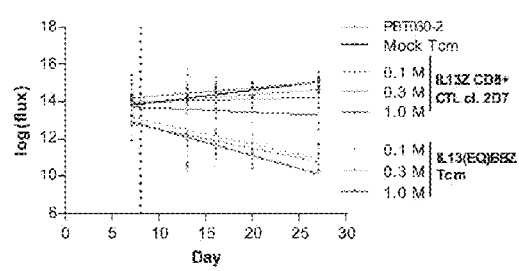
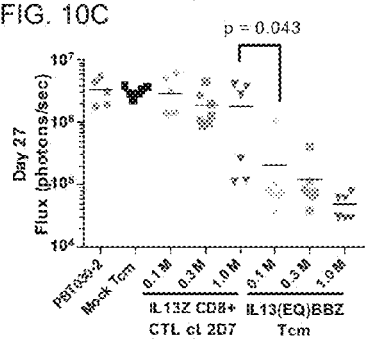
FIG. 10A
FIG. 10B
FIG. 10C

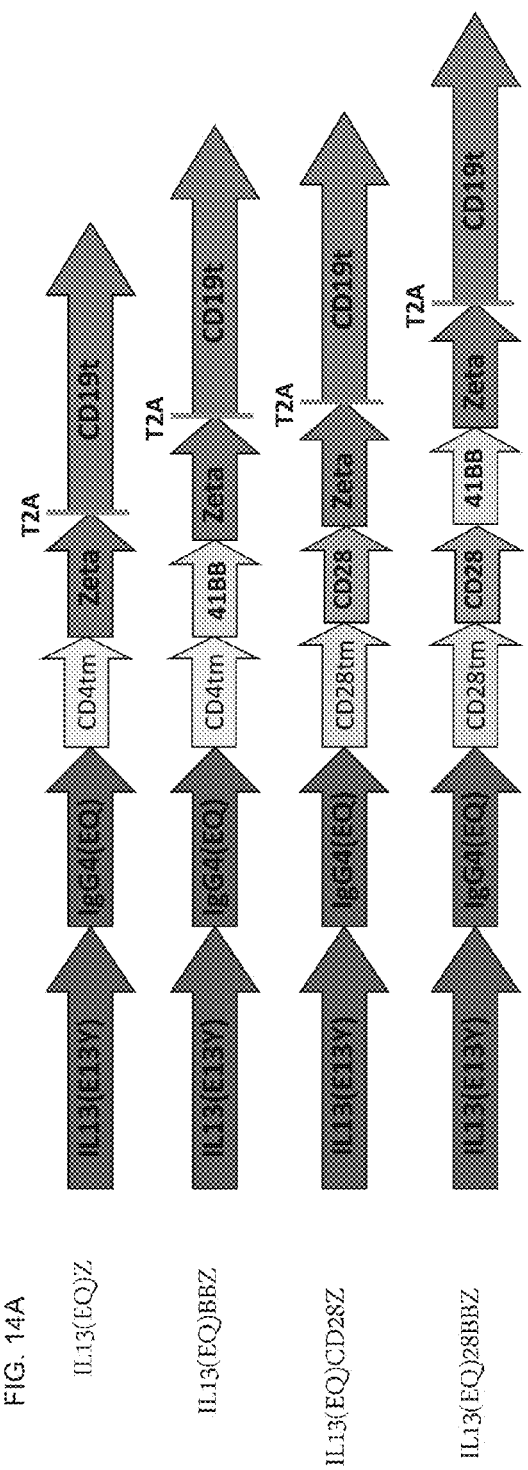
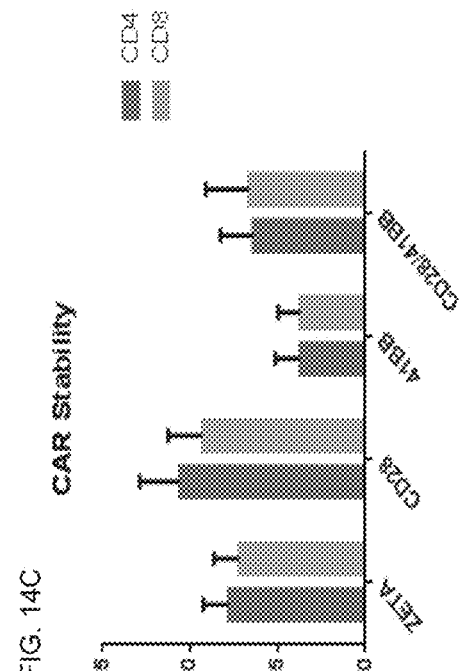
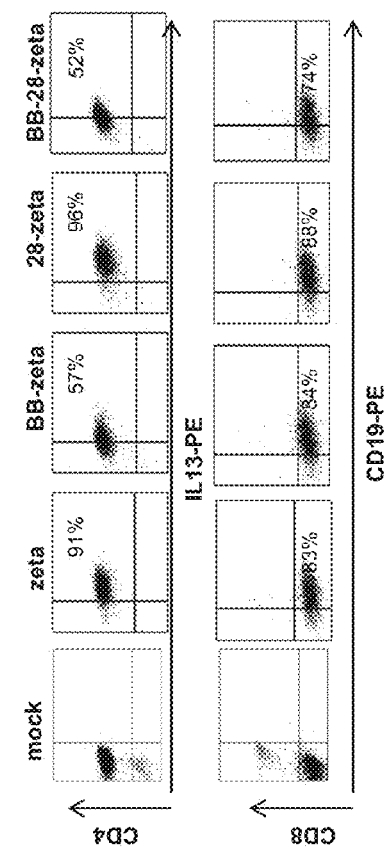
FIG. 14A
FIG. 14B
FIG. 14C

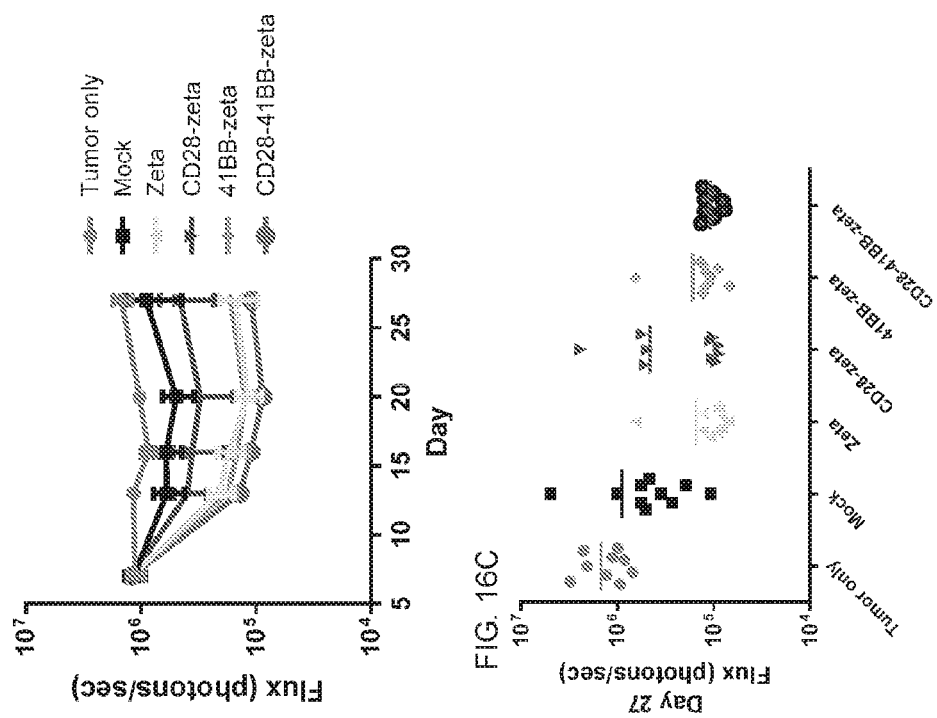
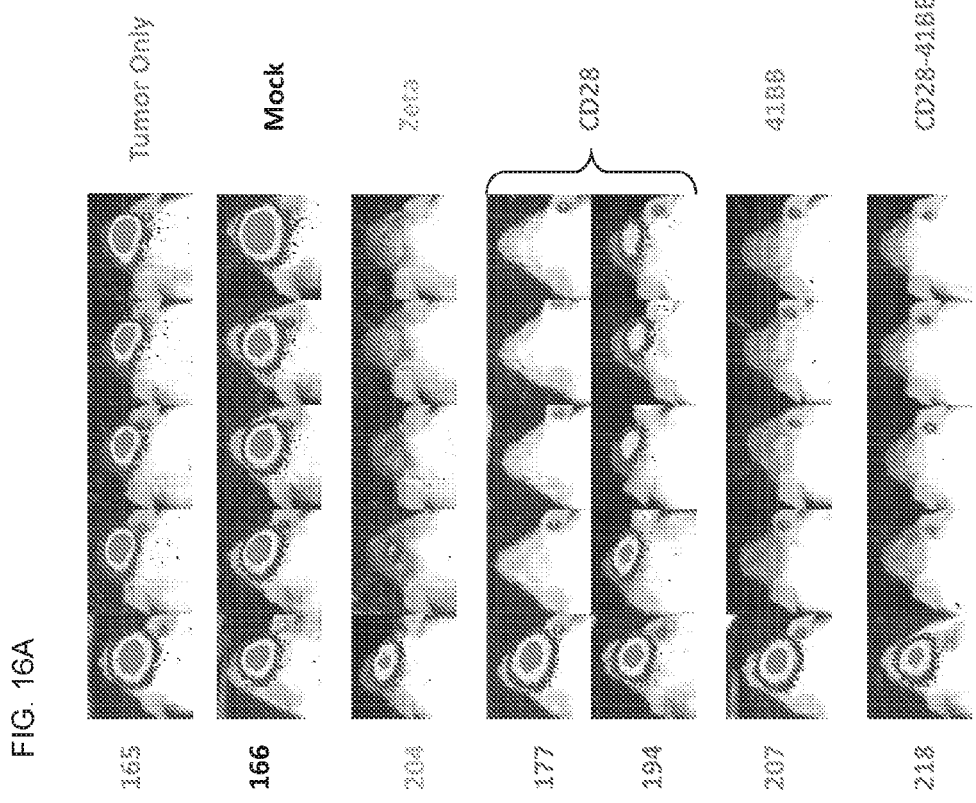
FIG. 16B
FIG. 16C
FIG. 16A

FIGURE 17 A

MLLLVTSLLLCELPHPAFLLIPGPVPPSTALRYLIEELVNITQNQKAPLCNGSMVWSINLTAGM

GMCSFRa signal peptide (22 aa)   IL13 (112 aa)

YCAALESLINVSGCSAIEKTQRMLSGFCPHKVSAGQFSSLHVRDTKIEVAQFVKDLLLHLKKLF

REGRFNESKYGPPCPPCPAPEFEGGPSVFLFPPKPKDTLMISRTPEVTCVVVDVSQEDPEVQF

IgG4(L235E, N297Q in bold) (229 aa)

NWYVDGVEVHNAKTKPREEQFQSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGKMALIVLGGVAGLL

CD4tm (22 aa)

LFIGLGIFFKRGRKKLLYIFKQPFMRPVQTTQEEDGCSCRFPEEEEGGCELGGGRVKFSRSADA

41BB (42 aa)                                                     Gly3   Zeta ( 112 aa)

PAYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPRLEGGGEGRGSLLTCGDV

T2A (24 aa)

EENPGPRMPPPRLLFFLLFLTPMEVRPEEPLVVKVEEGDNAVLQCLKGTSDGPTQQLTWSRE

SPLKPFLKLSLGLPGLGIHMRPLAIWLFIFNVSQQMGGFYLCQPGPPSEKAWQPGWTVNVE

GSGELFRWNVSDLGGLGCGLKNRSSEGPSSPSGKLMSPKLYVWAKDRPEIWEGEPPCVPPR

DSLNQSLSQDLTMAPGSTLWLSCGVPPDSVSRGPLSWTHVHPKGPKSLLSLELKDDRPARD

MWVMETGLLLPRATAQDAGKYYCHRGNLTMSFHLEITARPVLWHWLLRTGGWKVSAVTL

AYLIFCLCSLVGILHLQRALVLRRKR

FIGURE 18 A

Yellow highlighting indicates the IL-13 optimized codon region including the GMCSF signal sequence (IL13op).
 highlighting indicates the IgG4 optimized codon region (IgG4op[L235E, N297Q]).
 highlighting indicates the two anticipated amino acid changes within the IgG4 hinge region(L235E and N297Q).
 highlighting indicates the CD4 transmembrane optimized codon region.
 highlighting indicates the 41BB cytoplasmic signaling region (41BB cyto).
 highlighting indicates the 3 glycine linkers (g3).
Gray Highlighting indicates the CD3 zeta optimized codon region (zeta op).
 highlighting indicates the T2A sequence (T2A).
 highlighting Indicates the truncated CD19 sequence (CD19t).

```
                              1                                                  50
IL13(EQ)41BBZeta       (1)    GTTAGACCAGATCTGAGCCTGGGAGCTCTCTGGCTAACTAGGGAACCCAC
CD19Rop_epHIV7         (1)    GTTAGACCAGATCTGAGCCTGGGAGCTCTCTGGCTAACTAGGGAACCCAC
      Consensus        (1)    GTTAGACCAGATCTGAGCCTGGGAGCTCTCTGGCTAACTAGGGAACCCAC
                              51                                                 100
IL13(EQ)41BBZeta       (51)   TGCTTAAGCCTCAATAAAGCTTGCCTTGAGTGCTTCAAGTAGTGTGTGCC
CD19Rop_epHIV7         (51)   TGCTTAAGCCTCAATAAAGCTTGCCTTGAGTGCTTCAAGTAGTGTGTGCC
      Consensus        (51)   TGCTTAAGCCTCAATAAAGCTTGCCTTGAGTGCTTCAAGTAGTGTGTGCC
                              101                                                150
IL13(EQ)41BBZeta       (101)  CGTCTGTTGTGTGACTCTGGTAACTAGAGATCCCTCAGACCCTTTTAGTC
CD19Rop_epHIV7         (101)  CGTCTGTTGTGTGACTCTGGTAACTAGAGATCCCTCAGACCCTTTTAGTC
      Consensus        (101)  CGTCTGTTGTGTGACTCTGGTAACTAGAGATCCCTCAGACCCTTTTAGTC
                              151                                                200
IL13(EQ)41BBZeta       (151)  AGTGTGGAAAATCTCTAGCAGTGGCGCCCGAACAGGGACTTGAAAGCGAA
CD19Rop_epHIV7         (151)  AGTGTGGAAAATCTCTAGCAGTGGCGCCCGAACAGGGACTTGAAAGCGAA
      Consensus        (151)  AGTGTGGAAAATCTCTAGCAGTGGCGCCCGAACAGGGACTTGAAAGCGAA
                              201                                                250
IL13(EQ)41BBZeta       (201)  AGGGAAACCAGAGGAGCTCTCTCGACGCAGGACTCGGCTTGCTGAAGCGC
CD19Rop_epHIV7         (201)  AGGGAAACCAGAGGAGCTCTCTCGACGCAGGACTCGGCTTGCTGAAGCGC
      Consensus        (201)  AGGGAAACCAGAGGAGCTCTCTCGACGCAGGACTCGGCTTGCTGAAGCGC
                              251                                                300
IL13(EQ)41BBZeta       (251)  GCACGGCAAGAGGCGAGGGGCGGCGACTGGTGAGTACGCCAAAAATTTTG
CD19Rop_epHIV7         (251)  GCACGGCAAGAGGCGAGGGGCGGCGACTGGTGAGTACGCCAAAAATTTTG
      Consensus        (251)  GCACGGCAAGAGGCGAGGGGCGGCGACTGGTGAGTACGCCAAAAATTTTG
                              301                                                350
IL13(EQ)41BBZeta       (301)  ACTAGCGGAGGCTAGAAGGAGAGAGATGGGTGCGAGAGCGTCAGTATTAA
CD19Rop_epHIV7         (301)  ACTAGCGGAGGCTAGAAGGAGAGAGATGGGTGCGAGAGCGTCAGTATTAA
      Consensus        (301)  ACTAGCGGAGGCTAGAAGGAGAGAGATGGGTGCGAGAGCGTCAGTATTAA
                              351                                                400
IL13(EQ)41BBZeta       (351)  GCGGGGGAGAATTAGATCGATGGGAAAAAATTCGGTTAAGGCCAGGGGGA
CD19Rop_epHIV7         (351)  GCGGGGGAGAATTAGATCGATGGGAAAAAATTCGGTTAAGGCCAGGGGGA
      Consensus        (351)  GCGGGGGAGAATTAGATCGATGGGAAAAAATTCGGTTAAGGCCAGGGGGA
                              401                                                450
IL13(EQ)41BBZeta       (401)  AAGAAAAAATATAAATTAAAACATATAGTATGGGCAAGCAGGGAGCTAGA
CD19Rop_epHIV7         (401)  AAGAAAAAATATAAATTAAAACATATAGTATGGGCAAGCAGGGAGCTAGA
      Consensus        (401)  AAGAAAAAATATAAATTAAAACATATAGTATGGGCAAGCAGGGAGCTAGA
                              451                                                500
```

FIGURE 18B

```
IL13(EQ)41BBZeta   (451) ACGATTCGCAGTTAATCCTGGCCTGTTAGAAACATCAGAAGGCTGTAGAC
CD19Rop_epHIV7     (451) ACGATTCGCAGTTAATCCTGGCCTGTTAGAAACATCAGAAGGCTGTAGAC
       Consensus   (451) ACGATTCGCAGTTAATCCTGGCCTGTTAGAAACATCAGAAGGCTGTAGAC
                         501                                              550
IL13(EQ)41BBZeta   (501) AAATACTGGGACAGCTACAACCATCCCTTCAGACAGGATCAGAAGAACTT
CD19Rop_epHIV7     (501) AAATACTGGGACAGCTACAACCATCCCTTCAGACAGGATCAGAAGAACTT
       Consensus   (501) AAATACTGGGACAGCTACAACCATCCCTTCAGACAGGATCAGAAGAACTT
                         551                                              600
IL13(EQ)41BBZeta   (551) AGATCATTATATAATACAGTAGCAACCCTCTATTGTGTGCATCAAAGGAT
CD19Rop_epHIV7     (551) AGATCATTATATAATACAGTAGCAACCCTCTATTGTGTGCATCAAAGGAT
       Consensus   (551) AGATCATTATATAATACAGTAGCAACCCTCTATTGTGTGCATCAAAGGAT
                         601                                              650
IL13(EQ)41BBZeta   (601) AGAGATAAAAGACACCAAGGAAGCTTTAGACAAGATAGAGGAAGAGCAAA
CD19Rop_epHIV7     (601) AGAGATAAAAGACACCAAGGAAGCTTTAGACAAGATAGAGGAAGAGCAAA
       Consensus   (601) AGAGATAAAAGACACCAAGGAAGCTTTAGACAAGATAGAGGAAGAGCAAA
                         651                                              700
IL13(EQ)41BBZeta   (651) ACAAAAGTAAGAAAAAAGCACAGCAAGCAGCAGCTGACACAGGACACAGC
CD19Rop_epHIV7     (651) ACAAAAGTAAGAAAAAAGCACAGCAAGCAGCAGCTGACACAGGACACAGC
       Consensus   (651) ACAAAAGTAAGAAAAAAGCACAGCAAGCAGCAGCTGACACAGGACACAGC
                         701                                              750
IL13(EQ)41BBZeta   (701) AATCAGGTCAGCCAAAATTACCCTATAGTGCAGAACATCCAGGGGCAAAT
CD19Rop_epHIV7     (701) AATCAGGTCAGCCAAAATTACCCTATAGTGCAGAACATCCAGGGGCAAAT
       Consensus   (701) AATCAGGTCAGCCAAAATTACCCTATAGTGCAGAACATCCAGGGGCAAAT
                         751                                              800
IL13(EQ)41BBZeta   (751) GGTACATCAGGCCATATCACCTAGAACTTTAAATGCATGGGTAAAAGTAG
CD19Rop_epHIV7     (751) GGTACATCAGGCCATATCACCTAGAACTTTAAATGCATGGGTAAAAGTAG
       Consensus   (751) GGTACATCAGGCCATATCACCTAGAACTTTAAATGCATGGGTAAAAGTAG
                         801                                              850
IL13(EQ)41BBZeta   (801) TAGAAGAGAAGGCTTTCAGCCCAGAAGTGATACCCATGTTTTCAGCATTA
CD19Rop_epHIV7     (801) TAGAAGAGAAGGCTTTCAGCCCAGAAGTGATACCCATGTTTTCAGCATTA
       Consensus   (801) TAGAAGAGAAGGCTTTCAGCCCAGAAGTGATACCCATGTTTTCAGCATTA
                         851                                              900
IL13(EQ)41BBZeta   (851) TCAGAAGGAGCCACCCCACAAGATTTAAACACCATGCTAAACACAGTGGG
CD19Rop_epHIV7     (851) TCAGAAGGAGCCACCCCACAAGATTTAAACACCATGCTAAACACAGTGGG
       Consensus   (851) TCAGAAGGAGCCACCCCACAAGATTTAAACACCATGCTAAACACAGTGGG
                         901                                              950
IL13(EQ)41BBZeta   (901) GGGACATCAAGCAGCCATGCAAATGTTAAAAGAGACCATCAATGAGGAAG
CD19Rop_epHIV7     (901) GGGACATCAAGCAGCCATGCAAATGTTAAAAGAGACCATCAATGAGGAAG
       Consensus   (901) GGGACATCAAGCAGCCATGCAAATGTTAAAAGAGACCATCAATGAGGAAG
                         951                                             1000
IL13(EQ)41BBZeta   (951) CTGCAGGCAAAGAGAAGAGTGGTGCAGAGAGAAAAAAGAGCAGTGGGAAT
CD19Rop_epHIV7     (951) CTGCAGGCAAAGAGAAGAGTGGTGCAGAGAGAAAAAAGAGCAGTGGGAAT
       Consensus   (951) CTGCAGGCAAAGAGAAGAGTGGTGCAGAGAGAAAAAAGAGCAGTGGGAAT
                         1001                                            1050
IL13(EQ)41BBZeta  (1001) AGGAGCTTTGTTCCTTGGGTTCTTGGGAGCAGCAGGAAGCACTATGGGCG
CD19Rop_epHIV7    (1001) AGGAGCTTTGTTCCTTGGGTTCTTGGGAGCAGCAGGAAGCACTATGGGCG
       Consensus  (1001) AGGAGCTTTGTTCCTTGGGTTCTTGGGAGCAGCAGGAAGCACTATGGGCG
                         1051                                            1100
IL13(EQ)41BBZeta  (1051) CAGCGTCAATGACGCTGACGGTACAGGCCAGACAATTATTGTCTGGTATA
CD19Rop_epHIV7    (1051) CAGCGTCAATGACGCTGACGGTACAGGCCAGACAATTATTGTCTGGTATA
       Consensus  (1051) CAGCGTCAATGACGCTGACGGTACAGGCCAGACAATTATTGTCTGGTATA
                         1101                                            1150
IL13(EQ)41BBZeta  (1101) GTGCAGCAGCAGAACAATTTGCTGAGGGCTATTGAGGCGCAACAGCATCT
CD19Rop_epHIV7    (1101) GTGCAGCAGCAGAACAATTTGCTGAGGGCTATTGAGGCGCAACAGCATCT
       Consensus  (1101) GTGCAGCAGCAGAACAATTTGCTGAGGGCTATTGAGGCGCAACAGCATCT
```

FIGURE 18C

```
                            1151                                                  1200
IL13(EQ)41BBZeta   (1151)   GTTGCAACTCACAGTCTGGGGCATCAAGCAGCTCCAGGCAAGAATCCTGG
CD19Rop_epHIV7     (1151)   GTTGCAACTCACAGTCTGGGGCATCAAGCAGCTCCAGGCAAGAATCCTGG
       Consensus   (1151)   GTTGCAACTCACAGTCTGGGGCATCAAGCAGCTCCAGGCAAGAATCCTGG
                            1201                                                  1250
IL13(EQ)41BBZeta   (1201)   CTGTGGAAAGATACCTAAAGGATCAACAGCTCCTGGGGATTTGGGGTTGC
CD19Rop_epHIV7     (1201)   CTGTGGAAAGATACCTAAAGGATCAACAGCTCCTGGGGATTTGGGGTTGC
       Consensus   (1201)   CTGTGGAAAGATACCTAAAGGATCAACAGCTCCTGGGGATTTGGGGTTGC
                            1251                                                  1300
IL13(EQ)41BBZeta   (1251)   TCTGGAAAACTCATTTGCACCACTGCTGTGCCTTGGATCTACAAATGGCA
CD19Rop_epHIV7     (1251)   TCTGGAAAACTCATTTGCACCACTGCTGTGCCTTGGATCTACAAATGGCA
       Consensus   (1251)   TCTGGAAAACTCATTTGCACCACTGCTGTGCCTTGGATCTACAAATGGCA
                            1301                                                  1350
IL13(EQ)41BBZeta   (1301)   GTATTCATCCACAATTTTAAAAGAAAAGGGGGGATTGGGGGGTACAGTGC
CD19Rop_epHIV7     (1301)   GTATTCATCCACAATTTTAAAAGAAAAGGGGGGATTGGGGGGTACAGTGC
       Consensus   (1301)   GTATTCATCCACAATTTTAAAAGAAAAGGGGGGATTGGGGGGTACAGTGC
                            1351                                                  1400
IL13(EQ)41BBZeta   (1351)   AGGGGAAAGAATAGTAGACATAATAGCAACAGACATACAAACTAAAGAAT
CD19Rop_epHIV7     (1351)   AGGGGAAAGAATAGTAGACATAATAGCAACAGACATACAAACTAAAGAAT
       Consensus   (1351)   AGGGGAAAGAATAGTAGACATAATAGCAACAGACATACAAACTAAAGAAT
                            1401                                                  1450
IL13(EQ)41BBZeta   (1401)   TACAAAAACAAATTACAAAAATTCAAAATTTTCGGGTTTATTACAGGGAC
CD19Rop_epHIV7     (1401)   TACAAAAACAAATTACAAAAATTCAAAATTTTCGGGTTTATTACAGGGAC
       Consensus   (1401)   TACAAAAACAAATTACAAAAATTCAAAATTTTCGGGTTTATTACAGGGAC
                            1451                                                  1500
IL13(EQ)41BBZeta   (1451)   AGCAGAGATCCAGTTTGGGGATCAATTGCATGAAGAATCTGCTTAGGGTT
CD19Rop_epHIV7     (1451)   AGCAGAGATCCAGTTTGGGGATCAATTGCATGAAGAATCTGCTTAGGGTT
       Consensus   (1451)   AGCAGAGATCCAGTTTGGGGATCAATTGCATGAAGAATCTGCTTAGGGTT
                            1501                                                  1550
IL13(EQ)41BBZeta   (1501)   AGGCGTTTTGCGCTGCTTCGCGAGGATCTGCGATCGCTCCGGTGCCCGTC
CD19Rop_epHIV7     (1501)   AGGCGTTTTGCGCTGCTTCGCGAGGATCTGCGATCGCTCCGGTGCCCGTC
       Consensus   (1501)   AGGCGTTTTGCGCTGCTTCGCGAGGATCTGCGATCGCTCCGGTGCCCGTC
                            1551                                                  1600
IL13(EQ)41BBZeta   (1551)   AGTGGGCAGAGCGCACATCGCCCACAGTCCCCGAGAAGTTGGGGGGAGGG
CD19Rop_epHIV7     (1551)   AGTGGGCAGAGCGCACATCGCCCACAGTCCCCGAGAAGTTGGGGGGAGGG
       Consensus   (1551)   AGTGGGCAGAGCGCACATCGCCCACAGTCCCCGAGAAGTTGGGGGGAGGG
                            1601                                                  1650
IL13(EQ)41BBZeta   (1601)   GTCGGCAATTGAACCGGTGCCTAGAGAAGGTGGCGCGGGGTAAACTGGGA
CD19Rop_epHIV7     (1601)   GTCGGCAATTGAACCGGTGCCTAGAGAAGGTGGCGCGGGGTAAACTGGGA
       Consensus   (1601)   GTCGGCAATTGAACCGGTGCCTAGAGAAGGTGGCGCGGGGTAAACTGGGA
                            1651                                                  1700
IL13(EQ)41BBZeta   (1651)   AAGTGATGTCGTGTACTGGCTCCGCCTTTTTCCCGAGGGTGGGGGAGAAC
CD19Rop_epHIV7     (1651)   AAGTGATGTCGTGTACTGGCTCCGCCTTTTTCCCGAGGGTGGGGGAGAAC
       Consensus   (1651)   AAGTGATGTCGTGTACTGGCTCCGCCTTTTTCCCGAGGGTGGGGGAGAAC
                            1701                                                  1750
IL13(EQ)41BBZeta   (1701)   CGTATATAAGTGCAGTAGTCGCCGTGAACGTTCTTTTTCGCAACGGGTTT
CD19Rop_epHIV7     (1701)   CGTATATAAGTGCAGTAGTCGCCGTGAACGTTCTTTTTCGCAACGGGTTT
       Consensus   (1701)   CGTATATAAGTGCAGTAGTCGCCGTGAACGTTCTTTTTCGCAACGGGTTT
                            1751                                                  1800
IL13(EQ)41BBZeta   (1751)   GCCGCCAGAACACAGCTGAAGCTTCGAGGGGCTCGCATCTCTCCTTCACG
CD19Rop_epHIV7     (1751)   GCCGCCAGAACACAGCTGAAGCTTCGAGGGGCTCGCATCTCTCCTTCACG
       Consensus   (1751)   GCCGCCAGAACACAGCTGAAGCTTCGAGGGGCTCGCATCTCTCCTTCACG
                            1801                                                  1850
IL13(EQ)41BBZeta   (1801)   CGCCCGCCGCCCTACCTGAGGCCGCCATCCACGCCGGTTGAGTCGCGTTC
CD19Rop_epHIV7     (1801)   CGCCCGCCGCCCTACCTGAGGCCGCCATCCACGCCGGTTGAGTCGCGTTC
```

FIGURE 18D

```
Consensus         (1801) CGCCCGCCGCCCTACCTGAGGCCGCCATCCACGCCGGTTGAGTCGCGTTC
                         1851                                               1900
IL13(EQ)41BBZeta  (1851) TGCCGCCTCCCGCCTGTGGTGCCTCCTGAACTGCGTCCGCCGTCTAGGTA
CD19Rop_epHIV7    (1851) TGCCGCCTCCCGCCTGTGGTGCCTCCTGAACTGCGTCCGCCGTCTAGGTA
Consensus         (1851) TGCCGCCTCCCGCCTGTGGTGCCTCCTGAACTGCGTCCGCCGTCTAGGTA
                         1901                                               1950
IL13(EQ)41BBZeta  (1901) AGTTTAAAGCTCAGGTCGAGACCGGGCCTTTGTCCGGCGCTCCCTTGGAG
CD19Rop_epHIV7    (1901) AGTTTAAAGCTCAGGTCGAGACCGGGCCTTTGTCCGGCGCTCCCTTGGAG
Consensus         (1901) AGTTTAAAGCTCAGGTCGAGACCGGGCCTTTGTCCGGCGCTCCCTTGGAG
                         1951                                               2000
IL13(EQ)41BBZeta  (1951) CCTACCTAGACTCAGCCGGCTCTCCACGCTTTGCCTGACCCTGCTTGCTC
CD19Rop_epHIV7    (1951) CCTACCTAGACTCAGCCGGCTCTCCACGCTTTGCCTGACCCTGCTTGCTC
Consensus         (1951) CCTACCTAGACTCAGCCGGCTCTCCACGCTTTGCCTGACCCTGCTTGCTC
                         2001                                               2050
IL13(EQ)41BBZeta  (2001) AACTCTACGTCTTTGTTTCGTTTTCTGTTCTGCGCCGTTACAGATCCAAG
CD19Rop_epHIV7    (2001) AACTCTACGTCTTTGTTTCGTTTTCTGTTCTGCGCCGTTACAGATCCAAG
Consensus         (2001) AACTCTACGTCTTTGTTTCGTTTTCTGTTCTGCGCCGTTACAGATCCAAG
                         2051                                               2100
IL13(EQ)41BBZeta  (2051) CTGTGACCGGCGCCTACGGCTAGCGCCGCCACCATGCTGCTGCTGGTGAC
CD19Rop_epHIV7    (2051) CTGTGACCGGCGCCTACGGCTAGCGCCGCCACCATGCTGCTGCTGGTGAC
Consensus         (2051) CTGTGACCGGCGCCTACGGCTAGCGCCGCCACCATGCTGCTGCTGGTGAC
                         2101                                               2150
IL13(EQ)41BBZeta  (2101) CAGCCTGCTGCTGTGCGAGCTGCCCCACCCCGCCTTTCTGCTGATCCCTG
CD19Rop_epHIV7    (2101) CAGCCTGCTGCTGTGCGAGCTGCCCCACCCCGCCTTTCTGCTGATCCCCG
Consensus         (2101) CAGCCTGCTGCTGTGCGAGCTGCCCCACCCCGCCTTTCTGCTGATCCCC G
                         2151                                               2200
IL13(EQ)41BBZeta  (2151) GC--CCCG-TGCCCCCTAGCACCGCC---CTGCGCTACCTGATCGAGGAA
CD19Rop_epHIV7    (2151) ACATCCAGATGACCCAGACCACCTCCAGCCTGAGCGCCAGCCTGGGCGAC
Consensus         (2151) C  CC G TG CCC  A CACC CC   CTG GC  C     T G  GA
                         2201                                               2250
IL13(EQ)41BBZeta  (2195) CTGGTGA---------------------------ACATCACCCAGAACCAGAA
CD19Rop_epHIV7    (2201) CGGGTGACCATCAGCTGCCGGGCCAGCCAGGACATCAGCAAGTACCTGAA
Consensus         (2201) C GGTGA                    ACATCA C AG ACC GAA
                         2251                                               2300
IL13(EQ)41BBZeta  (2221) ---------------AGCCC--------CC----------CTGTGCAAC-----
CD19Rop_epHIV7    (2251) CTGGTATCAGCAGAAGCCCGACGGCACCGTCAAGCTGCTGATCTACCACA
Consensus         (2251)                AGCCC        CC           CTG  C AC
                         2301                                               2350
IL13(EQ)41BBZeta  (2237) ------GGCAGCAT---GGTGTG---------------------------
CD19Rop_epHIV7    (2301) CCAGCCGGCTGCACAGCGGCGTGCCCAGCCGGTTTAGCGGCAGCGGCTCC
Consensus         (2301)       GGC GCA   GG GTG
                         2351                                               2400
IL13(EQ)41BBZeta  (2251) ----------------GAGCATC----AACCTG------------------
CD19Rop_epHIV7    (2351) GGCACCGACTACAGCCTGACCATCTCCAACCTGGAACAGGAAGATATCGC
Consensus         (2351)                 GA CATC    AACCTG
                         2401                                               2450
IL13(EQ)41BBZeta  (2264) -ACC--------GCCGGCATGT------ACTG-----------TGCCGCC-
CD19Rop_epHIV7    (2401) CACCTACTTTTGCCAGCAGGGCAACACACTGCCCTACACCTTTGGCGGCG
Consensus         (2401)  ACC        GCC GCA G      ACTG            TG CG C
                         2451                                               2500
IL13(EQ)41BBZeta  (2288) ---------CTGGAAA-------GCCTGATCAACGTGAGCGGCT--------
CD19Rop_epHIV7    (2451) GAACAAAGCTGGAAATCACCGGCAGCACCTCCGGCAGCGGCAAGCCTGGC
Consensus         (2451)          CTGGAAA       GC  A C   CG  AGCGGC
                         2501                                               2550
IL13(EQ)41BBZeta  (2316) ----------GCAGCGCCATCG---------------AGAAAA---------
```

FIGURE 18E

```
CD19Rop_epHIV7   (2501)  AGCGGCGAGGGCAGCACCAAGGGCGAGGTGAAGCTGCAGGAAAGCGGCCC
      Consensus  (2501)          GCAGC CCA  G                 AG AAA
                         2551                                                  2600

IL13(EQ)41BBZeta (2334)  -------------CCCAGCG------------------------------
CD19Rop_epHIV7   (2551)  TGGCCTGGTGGCCCCCAGCCAGAGCCTGAGCGTGACCTGCACCGTGAGCG
      Consensus  (2551)              CCCAGC
                         2601                                                  2650

IL13(EQ)41BBZeta (2341)  ----GATGCTGTCCGGCTTCTGC-------------------CCCCACAAG
CD19Rop_epHIV7   (2601)  GCGTGAGCCTGCCCGACTACGGCGTGAGCTGGATCCGGCAGCCCCCCAGG
      Consensus  (2601)      GA   CTG CCG CT C GC                  CCCC CA G
                         2651                                                  2700

IL13(EQ)41BBZeta (2369)  -----------------------------GTGTCCGCCGGAC-----AGTT
CD19Rop_epHIV7   (2651)  AAGGGCCTGGAATGGCTGGGCGTGATCTGGGGCAGCGAGACCACCTACTA
      Consensus  (2651)                               G  G C GC   GAC      A T
                         2701                                                  2750

IL13(EQ)41BBZeta (2386)  CAGCAGCCTGC---ACGTGCGGG------------------ACACCAAGA
CD19Rop_epHIV7   (2701)  CAACAGCGCCCTGAAGAGCCGGCTGACCATCATCAAGGACAACAGCAAGA
      Consensus  (2701)  CA CAGC    C  A G GC GG                  ACA CAAGA
                         2751                                                  2800

IL13(EQ)41BBZeta (2415)  TCGAGGTGGCCCAGTTCGTGAAGGACCTGCTG---------------C
CD19Rop_epHIV7   (2751)  GCCAGGTGTTCCTGAAGATGAACAGCCTGCAGACCGACGACACCGCCATC
      Consensus  (2751)   C AGGTG  CC G    TGAA    CCTGC G                   C
                         2801                                                  2850

IL13(EQ)41BBZeta (2448)  TGCACCTG-----AAGAA---------------GCTGTTCCG-----GGA----
CD19Rop_epHIV7   (2801)  TACTACTGCGCCAAGCACTACTACTACGGCGGCAGCTACGCCATGGACTA
      Consensus  (2801)  T C CTG     AAG A              GC G T CG     GGA
                         2851                                                  2900

IL13(EQ)41BBZeta (2473)  ---GGGCCGGTTCAAC-------------------
CD19Rop_epHIV7   (2851)  CTGGGGCCAGGGCACCAGCGTGACCGTGAGCAGCGAGAGCAAGTACGGCC
      Consensus  (2851)      GGGCC G  CA C                    GAGAGCAAGTACGGCC
                         2901                                                  2950

IL13(EQ)41BBZeta (2502)
CD19Rop_epHIV7   (2901)  CTCCCTGCCCCCCTTGCCCTGCCCCCGAGTTCCTGGGCGGACCCAGCGTG
      Consensus  (2901)  CTCCCTGCCCCCCTTGCCCTGCCCC GAGTTC  GGGCGGACCCAGCGTG
                         2951                                                  3000

IL13(EQ)41BBZeta (2552)
CD19Rop_epHIV7   (2951)  TTCCTGTTCCCCCCCAAGCCCAAGGACACCCTGATGATCAGCCGGACCCC
      Consensus  (2951)  TTCCTGTTCCCCCCCAAGCCCAAGGACACCCTGATGATCAGCCGGACCCC
                         3001                                                  3050

IL13(EQ)41BBZeta (2602)
CD19Rop_epHIV7   (3001)  CGAGGTGACCTGCGTGGTGGTGGACGTGAGCCAGGAAGATCCCGAGGTCC
      Consensus  (3001)   GAGGTGACCTGCGTGGTGGTGGACGTGAGCCAGGAAGATCC GAGGTCC
                         3051                                                  3100

IL13(EQ)41BBZeta (2652)
CD19Rop_epHIV7   (3051)  AGTTCAATTGGTACGTGGACGGCGTGGAGGTGCACAACGCCAAGACCAAG
      Consensus  (3051)  AGTTCAATTGGTACGTGGACGGCGTGGAGGTGCACAACGCCAAGACCAAG
                         3101                                                  3150

IL13(EQ)41BBZeta (2702)
CD19Rop_epHIV7   (3101)  CCCAGGGAAGAGCAGTTCAACAGCACCTACCGGGTGGTGTCCGTGCTGAC
      Consensus  (3101)  CCCAGGGAAGAGCAGTTC A AGCACCTACCGGGTGGTGTCCGTGCTGAC
                         3151                                                  3200

IL13(EQ)41BBZeta (2752)
CD19Rop_epHIV7   (3151)  CGTGCTGCACCAGGACTGGCTGAACGGCAAGAATACAAGTGCAAGGTGT
      Consensus  (3151)  CGTGCTGCACCAGGACTGGCTGAACGGCAAGAATACAAGTGCAAGGTGT
                         3201                                                  3250
```

FIGURE 18F

```
IL13(EQ)41BBZeta   (2802)
CD19Rop_epHIV7     (3201) CCAACAAGGGCCTGCCCAGCAGCATCGAGAAAACCATCAGCAAGGCCAAG
      Consensus    (3201) CCAACAAGGGCCTGCCCAGCAGCATCGAGAAAACCATCAGCAAGGCCAAG
                          3251                                           3300
IL13(EQ)41BBZeta   (2852)
CD19Rop_epHIV7     (3251) GGCCAGCCTCGGGAGCCCCAGGTGTACACCCTGCCCCCTTCCCAGGAAGA
      Consensus    (3251) GGCCAGCCTCGGGAGCCCCAGGTGTACACCCTGCCCCCTTCCCAGGAAGA
                          3301                                           3350
IL13(EQ)41BBZeta   (2902)
CD19Rop_epHIV7     (3301) GATGACCAAGAATCAGGTGTCCCTGACCTGCCTGGTGAAGGGCTTCTACC
      Consensus    (3301) GATGACCAAGAATCAGGTGTCCCTGACCTGCCTGGTGAAGGGCTTCTACC
                          3351                                           3400
IL13(EQ)41BBZeta   (2952)
CD19Rop_epHIV7     (3351) CCAGCGACATCGCCGTGGAGTGGGAGAGCAACGGCCAGCCCGAGAACAAC
      Consensus    (3351) CCAGCGACATCGCCGTGGAGTGGGAGAGCAACGGCCAGCCCGAGAACAAC
                          3401                                           3450
IL13(EQ)41BBZeta   (3002) TACAAGACCACCCCCCCTGTGCTGGACAGCGACGGCAGCTTCTTCCTGTA
CD19Rop_epHIV7     (3401) TACAAGACCACCCCCCCTGTGCTGGACAGCGACGGCAGCTTCTTCCTGTA
      Consensus    (3401) TACAAGACCACCCCCCCTGTGCTGGACAGCGACGGCAGCTTCTTCCTGTA
                          3451                                           3500
IL13(EQ)41BBZeta   (3052) CAGCAGGCTGACCGTGGACAAGAGCCGGTGGCAGGAAGGCAACGTCTTTA
CD19Rop_epHIV7     (3451) CAGCAGGCTGACCGTGGACAAGAGCCGGTGGCAGGAAGGCAACGTCTTTA
      Consensus    (3451) CAGCAGGCTGACCGTGGACAAGAGCCGGTGGCAGGAAGGCAACGTCTTTA
                          3501                                           3550
IL13(EQ)41BBZeta   (3102) GCTGCAGCGTGATGCACGAGGCCCTGCACAACCACTACACCCAGAAGAGC
CD19Rop_epHIV7     (3501) GCTGCAGCGTGATGCACGAGGCCCTGCACAACCACTACACCCAGAAGAGC
      Consensus    (3501) GCTGCAGCGTGATGCACGAGGCCCTGCACAACCACTACACCCAGAAGAGC
                          3551                                           3600
IL13(EQ)41BBZeta   (3152) CTGTCCCTGAGCCTGGGCAAG
CD19Rop_epHIV7     (3551) CTGTCCCTGAGCCTGGGCAAGATGGCCCTGATCGTGCTGGGCGGCGTGGC
      Consensus    (3551) CTGTCCCTGAGCCTGGGCAAGATGGCCCTGATCGTGCTGGGCGGCGTGGC
                          3601                                           3650
IL13(EQ)41BBZeta   (3202)
CD19Rop_epHIV7     (3601) CGGGCTGCTGCTGTTCATCGGCCTGGGCATCTTTTTC--------------
      Consensus    (3601) CGGGCTGCTGCTGTTCATCGGCCTGGGCATCTTTTTC
                          3651                                           3700
IL13(EQ)41BBZeta   (3252) -------------------------------C------------------
CD19Rop_epHIV7     (3638) -------------------------------C------------------
      Consensus    (3651)                                C
                          3701                                           3750
IL13(EQ)41BBZeta   (3302) --------------------------------------------------
CD19Rop_epHIV7     (3639) --------------------------------------------------
      Consensus    (3701)
                          3751                                           3800
IL13(EQ)41BBZeta   (3352)                         CGGGTGAAGTTCAGCCGGTCCGCCGACG
CD19Rop_epHIV7     (3639) ------------------------GGGTGAAGTTCAGCCGGTCCGCCGACG
      Consensus    (3751)                         GGGTGAAGTTCAGCCGGTCCGCCGACG
                          3801                                           3850
IL13(EQ)41BBZeta   (3402) CCCCTGCCTACCAGCAGGGCCAGAACCAGCTGTACAACGAGCTGAACCTG
CD19Rop_epHIV7     (3666) CCCCTGCCTACCAGCAGGGCCAGAACCAGCTGTACAACGAGCTGAACCTG
      Consensus    (3801) CCCCTGCCTACCAGCAGGGCCAGAACCAGCTGTACAACGAGCTGAACCTG
                          3851                                           3900
IL13(EQ)41BBZeta   (3452) GGCAGGCGGGAGGAATACGACGTGCTGGACAAGCGGAGAGGCCGGGACCC
CD19Rop_epHIV7     (3716) GGCAGGCGGGAGGAATACGACGTGCTGGACAAGCGGAGAGGCCGGGACCC
      Consensus    (3851) GGCAGGCGGGAGGAATACGACGTGCTGGACAAGCGGAGAGGCCGGGACCC
```

FIGURE 18G

```
                              3901                                          3950
IL13(EQ)41BBZeta  (3502)  TGAGATGGGCGGCAAGCCTCGGCGGAAGAACCCCCAGGAAGGCCTGTATA
CD19Rop_epHIV7    (3766)  TGAGATGGGCGGCAAGCCCAGGCGGAAGAACCCTCAGGAAGGCCTGTATA
      Consensus   (3901)  TGAGATGGGCGGCAAGCC  GGCGGAAGAACCC CAGGAAGGCCTGTATA
                              3951                                          4000
IL13(EQ)41BBZeta  (3552)  ACGAACTGCAGAAAGACAAGATGGCCGAGGCCTACAGCGAGATCGGCATG
CD19Rop_epHIV7    (3816)  ACGAACTGCAGAAAGACAAGATGGCCGAGGCCTACAGCGAGATCGGCATG
      Consensus   (3951)  ACGAACTGCAGAAAGACAAGATGGCCGAGGCCTACAGCGAGATCGGCATG
                              4001                                          4050
IL13(EQ)41BBZeta  (3602)  AAGGGCGAGCGGAGGCGGGGCAAGGGCCACGACGGCCTGTATCAGGGCCT
CD19Rop_epHIV7    (3866)  AAGGGCGAGCGGCGGAGGGGCAAGGGCCACGACGGCCTGTACCAGGGCCT
      Consensus   (4001)  AAGGGCGAGCGG GG GGGGCAAGGGCCACGACGGCCTGTA CAGGGCCT
                              4051                                          4100
IL13(EQ)41BBZeta  (3652)  GTCCACCGCCACCAAGGATACCTACGACGCCCTGCACATGCAGGCCCTGC
CD19Rop_epHIV7    (3916)  GAGCACCGCCACCAAGGATACCTACGACGCCCTGCACATGCAGGCCCTGC
      Consensus   (4051)  G  CACCGCCACCAAGGATACCTACGACGCCCTGCACATGCAGGCCCTGC
                              4101                                          4150
IL13(EQ)41BBZeta  (3702)  CCCCAAGG
CD19Rop_epHIV7    (3966)  CCCC----------------------------------------------
      Consensus   (4101)  CCCC
                              4151                                          4200
IL13(EQ)41BBZeta  (3752)  --------------------------------------------------
CD19Rop_epHIV7    (3970)  --------------------------------------------------
      Consensus   (4151)
                              4201                                          4250
IL13(EQ)41BBZeta  (3802)  --------------------------------------------------
CD19Rop_epHIV7    (3970)  --------------------------------------------------
      Consensus   (4201)
                              4251                                          4300
IL13(EQ)41BBZeta  (3852)  --------------------------------------------------
CD19Rop_epHIV7    (3970)  --------------------------------------------------
      Consensus   (4251)
                              4301                                          4350
IL13(EQ)41BBZeta  (3902)  --------------------------------------------------
CD19Rop_epHIV7    (3970)  --------------------------------------------------
      Consensus   (4301)
                              4351                                          4400
IL13(EQ)41BBZeta  (3952)  --------------------------------------------------
CD19Rop_epHIV7    (3970)  --------------------------------------------------
      Consensus   (4351)
                              4401                                          4450
IL13(EQ)41BBZeta  (4002)  --------------------------------------------------
CD19Rop_epHIV7    (3970)  --------------------------------------------------
      Consensus   (4401)
                              4451                                          4500
IL13(EQ)41BBZeta  (4052)  --------------------------------------------------
CD19Rop_epHIV7    (3970)  --------------------------------------------------
      Consensus   (4451)
                              4501                                          4550
IL13(EQ)41BBZeta  (4102)  --------------------------------------------------
CD19Rop_epHIV7    (3970)  --------------------------------------------------
      Consensus   (4501)
                              4551                                          4600
IL13(EQ)41BBZeta  (4152)  --------------------------------------------------
CD19Rop_epHIV7    (3970)  --------------------------------------------------
```

FIGURE 18H

```
      Consensus  (4551)
                        4601                                               4650
IL13(EQ)41BBZeta (4202)
   CD19Rop_epHIV7 (3970) --------------------------------------------------
      Consensus  (4601)
                        4651                                               4700
IL13(EQ)41BBZeta (4252)
   CD19Rop_epHIV7 (3970) --------------------------------------------------
      Consensus  (4651)
                        4701                                               4750
IL13(EQ)41BBZeta (4302)
   CD19Rop_epHIV7 (3970) ----------------------------C------AGG------------
      Consensus  (4701)                              C      AGG
                        4751                                               4800
IL13(EQ)41BBZeta (4352)
   CD19Rop_epHIV7 (3974) -------------------------------T------------------
      Consensus  (4751)
                        4801                                               4850
IL13(EQ)41BBZeta (4402)
   CD19Rop_epHIV7 (3975) --------------------------------------------------
      Consensus  (4801)
                        4851                                               4900
IL13(EQ)41BBZeta (4452)
   CD19Rop_epHIV7 (3975) --------------------------------------------------
      Consensus  (4851)
                        4901                                               4950
IL13(EQ)41BBZeta (4502)
   CD19Rop_epHIV7 (3975) --------------------------------------------------
      Consensus  (4901)
                        4951                                               5000
IL13(EQ)41BBZeta (4552)
   CD19Rop_epHIV7 (3975) --------------------------------------------------
      Consensus  (4951)
                        5001                                               5050
IL13(EQ)41BBZeta (4602)
   CD19Rop_epHIV7 (3975) --------------------------------------------------
      Consensus  (5001)
                        5051                                               5100
IL13(EQ)41BBZeta (4652)
   CD19Rop_epHIV7 (3975) --------------------------------------------------
      Consensus  (5051)
                        5101                                               5150
IL13(EQ)41BBZeta (4702)
   CD19Rop_epHIV7 (3975) --------------------------------------------------
      Consensus  (5101)
                        5151                                               5200
IL13(EQ)41BBZeta (4752)    TCTAGACCCGGGCTGCAGGAATTCGATATCAAGCTTATCGATAATCAA
   CD19Rop_epHIV7 (3975) ------GACCCGGGCTGCAGGAATTCGATATCAAGCTTATCGATAATCAA
      Consensus  (5151)        GACCCGGGCTGCAGGAATTCGATATCAAGCTTATCGATAATCAA
                        5201                                               5250
IL13(EQ)41BBZeta (4802) CCTCTGGATTACAAAATTTGTGAAAGATTGACTGGTATTCTTAACTATGT
   CD19Rop_epHIV7 (4019) CCTCTGGATTACAAAATTTGTGAAAGATTGACTGGTATTCTTAACTATGT
      Consensus  (5201) CCTCTGGATTACAAAATTTGTGAAAGATTGACTGGTATTCTTAACTATGT
                        5251                                               5300
IL13(EQ)41BBZeta (4852) TGCTCCTTTTACGCTATGTGGATACGCTGCTTTAATGCCTTTGTATCATG
```

FIGURE 18I

```
CD19Rop_epHIV7  (4069) TGCTCCTTTTACGCTATGTGGATACGCTGCTTTAATGCCTTTGTATCATG
     Consensus  (5251) TGCTCCTTTTACGCTATGTGGATACGCTGCTTTAATGCCTTTGTATCATG
                       5301                                              5350
IL13(EQ)41BBZeta (4902) CTATTGCTTCCCGTATGGCTTTCATTTTCTCCTCCTTGTATAAATCCTGG
CD19Rop_epHIV7  (4119) CTATTGCTTCCCGTATGGCTTTCATTTTCTCCTCCTTGTATAAATCCTGG
     Consensus  (5301) CTATTGCTTCCCGTATGGCTTTCATTTTCTCCTCCTTGTATAAATCCTGG
                       5351                                              5400
IL13(EQ)41BBZeta (4952) TTGCTGTCTCTTTATGAGGAGTTGTGGCCCGTTGTCAGGCAACGTGGCGT
CD19Rop_epHIV7  (4169) TTGCTGTCTCTTTATGAGGAGTTGTGGCCCGTTGTCAGGCAACGTGGCGT
     Consensus  (5351) TTGCTGTCTCTTTATGAGGAGTTGTGGCCCGTTGTCAGGCAACGTGGCGT
                       5401                                              5450
IL13(EQ)41BBZeta (5002) GGTGTGCACTGTGTTTGCTGACGCAACCCCCACTGGTTGGGGCATTGCCA
CD19Rop_epHIV7  (4219) GGTGTGCACTGTGTTTGCTGACGCAACCCCCACTGGTTGGGGCATTGCCA
     Consensus  (5401) GGTGTGCACTGTGTTTGCTGACGCAACCCCCACTGGTTGGGGCATTGCCA
                       5451                                              5500
IL13(EQ)41BBZeta (5052) CCACCTGTCAGCTCCTTTCCGGGACTTTCGCTTTCCCCCTCCCTATTGCC
CD19Rop_epHIV7  (4269) CCACCTGTCAGCTCCTTTCCGGGACTTTCGCTTTCCCCCTCCCTATTGCC
     Consensus  (5451) CCACCTGTCAGCTCCTTTCCGGGACTTTCGCTTTCCCCCTCCCTATTGCC
                       5501                                              5550
IL13(EQ)41BBZeta (5102) ACGGCGGAACTCATCGCCGCCTGCCTTGCCCGCTGCTGGACAGGGGCTCG
CD19Rop_epHIV7  (4319) ACGGCGGAACTCATCGCCGCCTGCCTTGCCCGCTGCTGGACAGGGGCTCG
     Consensus  (5501) ACGGCGGAACTCATCGCCGCCTGCCTTGCCCGCTGCTGGACAGGGGCTCG
                       5551                                              5600
IL13(EQ)41BBZeta (5152) GCTGTTGGGCACTGACAATTCCGTGGTGTTGTCGGGGAAATCATCGTCCT
CD19Rop_epHIV7  (4369) GCTGTTGGGCACTGACAATTCCGTGGTGTTGTCGGGGAAATCATCGTCCT
     Consensus  (5551) GCTGTTGGGCACTGACAATTCCGTGGTGTTGTCGGGGAAATCATCGTCCT
                       5601                                              5650
IL13(EQ)41BBZeta (5202) TTCCTTGGCTGCTCGCCTGTGTTGCCACCTGGATTCTGCGCGGGACGTCC
CD19Rop_epHIV7  (4419) TTCCTTGGCTGCTCGCCTGTGTTGCCACCTGGATTCTGCGCGGGACGTCC
     Consensus  (5601) TTCCTTGGCTGCTCGCCTGTGTTGCCACCTGGATTCTGCGCGGGACGTCC
                       5651                                              5700
IL13(EQ)41BBZeta (5252) TTCTGCTACGTCCCTTCGGCCCTCAATCCAGCGGACCTTCCTTCCCGCGG
CD19Rop_epHIV7  (4469) TTCTGCTACGTCCCTTCGGCCCTCAATCCAGCGGACCTTCCTTCCCGCGG
     Consensus  (5651) TTCTGCTACGTCCCTTCGGCCCTCAATCCAGCGGACCTTCCTTCCCGCGG
                       5701                                              5750
IL13(EQ)41BBZeta (5302) CCTGCTGCCGGCTCTGCGGCCTCTTCCGCGTCTTCGCCTTCGCCCTCAGA
CD19Rop_epHIV7  (4519) CCTGCTGCCGGCTCTGCGGCCTCTTCCGCGTCTTCGCCTTCGCCCTCAGA
     Consensus  (5701) CCTGCTGCCGGCTCTGCGGCCTCTTCCGCGTCTTCGCCTTCGCCCTCAGA
                       5751                                              5800
IL13(EQ)41BBZeta (5352) CGAGTCGGATCTCCCTTTGGGCCGCCTCCCCGCATCGATACCGTCGACTA
CD19Rop_epHIV7  (4569) CGAGTCGGATCTCCCTTTGGGCCGCCTCCCCGCATCGATACCGTCGACTA
     Consensus  (5751) CGAGTCGGATCTCCCTTTGGGCCGCCTCCCCGCATCGATACCGTCGACTA
                       5801                                              5850
IL13(EQ)41BBZeta (5402) GCCGTACCTTTAAGACCAATGACTTACAAGGCAGCTGTAGATCTTAGCCA
CD19Rop_epHIV7  (4619) GCCGTACCTTTAAGACCAATGACTTACAAGGCAGCTGTAGATCTTAGCCA
     Consensus  (5801) GCCGTACCTTTAAGACCAATGACTTACAAGGCAGCTGTAGATCTTAGCCA
                       5851                                              5900
IL13(EQ)41BBZeta (5452) CTTTTTAAAAGAAAAGGGGGGACTGGAAGGGCTAATTCACTCCCAAAGAA
CD19Rop_epHIV7  (4669) CTTTTTAAAAGAAAAGGGGGGACTGGAAGGGCTAATTCACTCCCAAAGAA
     Consensus  (5851) CTTTTTAAAAGAAAAGGGGGGACTGGAAGGGCTAATTCACTCCCAAAGAA
                       5901                                              5950
IL13(EQ)41BBZeta (5502) GACAAGATCTGCTTTTTGCCTGTACTGGGTCTCTCTGGTTAGACCAGATC
CD19Rop_epHIV7  (4719) GACAAGATCTGCTTTTTGCCTGTACTGGGTCTCTCTGGTTAGACCAGATC
     Consensus  (5901) GACAAGATCTGCTTTTTGCCTGTACTGGGTCTCTCTGGTTAGACCAGATC
                       5951                                              6000
```

FIGURE 18J

```
IL13(EQ)41BBZeta  (5552)  TGAGCCTGGGAGCTCTCTGGCTAACTAGGGAACCCACTGCTTAAGCCTCA
CD19Rop_epHIV7    (4769)  TGAGCCTGGGAGCTCTCTGGCTAACTAGGGAACCCACTGCTTAAGCCTCA
     Consensus    (5951)  TGAGCCTGGGAGCTCTCTGGCTAACTAGGGAACCCACTGCTTAAGCCTCA
                          6001                                            6050
IL13(EQ)41BBZeta  (5602)  ATAAAGCTTGCCTTGAGTGCTTCAAGTAGTGTGTGCCCGTCTGTTGTGTG
CD19Rop_epHIV7    (4819)  ATAAAGCTTGCCTTGAGTGCTTCAAGTAGTGTGTGCCCGTCTGTTGTGTG
     Consensus    (6001)  ATAAAGCTTGCCTTGAGTGCTTCAAGTAGTGTGTGCCCGTCTGTTGTGTG
                          6051                                            6100
IL13(EQ)41BBZeta  (5652)  ACTCTGGTAACTAGAGATCCCTCAGACCCTTTTAGTCAGTGTGGAAAATC
CD19Rop_epHIV7    (4869)  ACTCTGGTAACTAGAGATCCCTCAGACCCTTTTAGTCAGTGTGGAAAATC
     Consensus    (6051)  ACTCTGGTAACTAGAGATCCCTCAGACCCTTTTAGTCAGTGTGGAAAATC
                          6101                                            6150
IL13(EQ)41BBZeta  (5702)  TCTAGCAGAATTCGATATCAAGCTTATCGATACCGTCGACCTCGAGGGGG
CD19Rop_epHIV7    (4919)  TCTAGCAGAATTCGATATCAAGCTTATCGATACCGTCGACCTCGAGGGGG
     Consensus    (6101)  TCTAGCAGAATTCGATATCAAGCTTATCGATACCGTCGACCTCGAGGGGG
                          6151                                            6200
IL13(EQ)41BBZeta  (5752)  GGCCCGGTACCCAATTCGCCCTATAGTGAGTCGTATTACAATTCACTGGC
CD19Rop_epHIV7    (4969)  GGCCCGGTACCCAATTCGCCCTATAGTGAGTCGTATTACAATTCACTGGC
     Consensus    (6151)  GGCCCGGTACCCAATTCGCCCTATAGTGAGTCGTATTACAATTCACTGGC
                          6201                                            6250
IL13(EQ)41BBZeta  (5802)  CGTCGTTTTACAACGTCGTGACTGGGAAAACCCTGGCGTTACCCAACTTA
CD19Rop_epHIV7    (5019)  CGTCGTTTTACAACGTCGTGACTGGGAAAACCCTGGCGTTACCCAACTTA
     Consensus    (6201)  CGTCGTTTTACAACGTCGTGACTGGGAAAACCCTGGCGTTACCCAACTTA
                          6251                                            6300
IL13(EQ)41BBZeta  (5852)  ATCGCCTTGCAGCACATCCCCCTTTCGCCAGCTGGCGTAATAGCGAAGAG
CD19Rop_epHIV7    (5069)  ATCGCCTTGCAGCACATCCCCCTTTCGCCAGCTGGCGTAATAGCGAAGAG
     Consensus    (6251)  ATCGCCTTGCAGCACATCCCCCTTTCGCCAGCTGGCGTAATAGCGAAGAG
                          6301                                            6350
IL13(EQ)41BBZeta  (5902)  GCCCGCACCGATCGCCCTTCCCAACAGTTGCGCAGCCTGAATGGCGAATG
CD19Rop_epHIV7    (5119)  GCCCGCACCGATCGCCCTTCCCAACAGTTGCGCAGCCTGAATGGCGAATG
     Consensus    (6301)  GCCCGCACCGATCGCCCTTCCCAACAGTTGCGCAGCCTGAATGGCGAATG
                          6351                                            6400
IL13(EQ)41BBZeta  (5952)  GAAATTGTAAGCGTTAATATTTTGTTAAAATTCGCGTTAAATTTTTGTTA
CD19Rop_epHIV7    (5169)  GAAATTGTAAGCGTTAATATTTTGTTAAAATTCGCGTTAAATTTTTGTTA
     Consensus    (6351)  GAAATTGTAAGCGTTAATATTTTGTTAAAATTCGCGTTAAATTTTTGTTA
                          6401                                            6450
IL13(EQ)41BBZeta  (6002)  AATCAGCTCATTTTTTAACCAATAGGCCGAAATCGGCAAAATCCCTTATA
CD19Rop_epHIV7    (5219)  AATCAGCTCATTTTTTAACCAATAGGCCGAAATCGGCAAAATCCCTTATA
     Consensus    (6401)  AATCAGCTCATTTTTTAACCAATAGGCCGAAATCGGCAAAATCCCTTATA
                          6451                                            6500
IL13(EQ)41BBZeta  (6052)  AATCAAAAGAATAGACCGAGATAGGGTTGAGTGTTGTTCCAGTTTGGAAC
CD19Rop_epHIV7    (5269)  AATCAAAAGAATAGACCGAGATAGGGTTGAGTGTTGTTCCAGTTTGGAAC
     Consensus    (6451)  AATCAAAAGAATAGACCGAGATAGGGTTGAGTGTTGTTCCAGTTTGGAAC
                          6501                                            6550
IL13(EQ)41BBZeta  (6102)  AAGAGTCCACTATTAAAGAACGTGGACTCCAACGTCAAAGGGCGAAAAAC
CD19Rop_epHIV7    (5319)  AAGAGTCCACTATTAAAGAACGTGGACTCCAACGTCAAAGGGCGAAAAAC
     Consensus    (6501)  AAGAGTCCACTATTAAAGAACGTGGACTCCAACGTCAAAGGGCGAAAAAC
                          6551                                            6600
IL13(EQ)41BBZeta  (6152)  CGTCTATCAGGGCGATGGCCCACTACGTGAACCATCACCCTAATCAAGTT
CD19Rop_epHIV7    (5369)  CGTCTATCAGGGCGATGGCCCACTACGTGAACCATCACCCTAATCAAGTT
     Consensus    (6551)  CGTCTATCAGGGCGATGGCCCACTACGTGAACCATCACCCTAATCAAGTT
                          6601                                            6650
IL13(EQ)41BBZeta  (6202)  TTTGGGGTCGAGGTGCCGTAAAGCACTAAATCGGAACCCTAAAGGGAGC
CD19Rop_epHIV7    (5419)  TTTGGGGTCGAGGTGCCGTAAAGCACTAAATCGGAACCCTAAAGGGAGC
     Consensus    (6601)  TTTGGGGTCGAGGTGCCGTAAAGCACTAAATCGGAACCCTAAAGGGAGC
```

FIGURE 18K

```
                            6651                                                   6700
IL13(EQ)41BBZeta   (6252)   CCCCGATTTAGAGCTTGACGGGGAAAGCCGGCGAACGTGGCGAGAAAGGA
CD19Rop_epHIV7     (5469)   CCCCGATTTAGAGCTTGACGGGGAAAGCCGGCGAACGTGGCGAGAAAGGA
      Consensus    (6651)   CCCCGATTTAGAGCTTGACGGGGAAAGCCGGCGAACGTGGCGAGAAAGGA
                            6701                                                   6750
IL13(EQ)41BBZeta   (6302)   AGGGAAGAAAGCGAAAGGAGCGGGCGCTAGGGCGCTGGCAAGTGTAGCGG
CD19Rop_epHIV7     (5519)   AGGGAAGAAAGCGAAAGGAGCGGGCGCTAGGGCGCTGGCAAGTGTAGCGG
      Consensus    (6701)   AGGGAAGAAAGCGAAAGGAGCGGGCGCTAGGGCGCTGGCAAGTGTAGCGG
                            6751                                                   6800
IL13(EQ)41BBZeta   (6352)   TCACGCTGCGCGTAACCACCACACCCGCCGCGCTTAATGCGCCGCTACAG
CD19Rop_epHIV7     (5569)   TCACGCTGCGCGTAACCACCACACCCGCCGCGCTTAATGCGCCGCTACAG
      Consensus    (6751)   TCACGCTGCGCGTAACCACCACACCCGCCGCGCTTAATGCGCCGCTACAG
                            6801                                                   6850
IL13(EQ)41BBZeta   (6402)   GGCGCGTCAGGTGGCACTTTTCGGGGAAATGTGCGCGGAACCCCTATTTG
CD19Rop_epHIV7     (5619)   GGCGCGTCAGGTGGCACTTTTCGGGGAAATGTGCGCGGAACCCCTATTTG
      Consensus    (6801)   GGCGCGTCAGGTGGCACTTTTCGGGGAAATGTGCGCGGAACCCCTATTTG
                            6851                                                   6900
IL13(EQ)41BBZeta   (6452)   TTTATTTTTCTAAATACATTCAAATATGTATCCGCTCATGAGACAATAAC
CD19Rop_epHIV7     (5669)   TTTATTTTTCTAAATACATTCAAATATGTATCCGCTCATGAGACAATAAC
      Consensus    (6851)   TTTATTTTTCTAAATACATTCAAATATGTATCCGCTCATGAGACAATAAC
                            6901                                                   6950
IL13(EQ)41BBZeta   (6502)   CCTGATAAATGCTTCAATAATATTGAAAAAGGAAGAGTATGAGTATTCAA
CD19Rop_epHIV7     (5719)   CCTGATAAATGCTTCAATAATATTGAAAAAGGAAGAGTATGAGTATTCAA
      Consensus    (6901)   CCTGATAAATGCTTCAATAATATTGAAAAAGGAAGAGTATGAGTATTCAA
                            6951                                                   7000
IL13(EQ)41BBZeta   (6552)   CATTTCCGTGTCGCCCTTATTCCCTTTTTTGCGGCATTTTGCCTTCCTGT
CD19Rop_epHIV7     (5769)   CATTTCCGTGTCGCCCTTATTCCCTTTTTTGCGGCATTTTGCCTTCCTGT
      Consensus    (6951)   CATTTCCGTGTCGCCCTTATTCCCTTTTTTGCGGCATTTTGCCTTCCTGT
                            7001                                                   7050
IL13(EQ)41BBZeta   (6602)   TTTTGCTCACCCAGAAACGCTGGTGAAAGTAAAAGATGCTGAAGATCAGT
CD19Rop_epHIV7     (5819)   TTTTGCTCACCCAGAAACGCTGGTGAAAGTAAAAGATGCTGAAGATCAGT
      Consensus    (7001)   TTTTGCTCACCCAGAAACGCTGGTGAAAGTAAAAGATGCTGAAGATCAGT
                            7051                                                   7100
IL13(EQ)41BBZeta   (6652)   TGGGTGCACGAGTGGGTTACATCGAACTGGATCTCAACAGCGGTAAGATC
CD19Rop_epHIV7     (5869)   TGGGTGCACGAGTGGGTTACATCGAACTGGATCTCAACAGCGGTAAGATC
      Consensus    (7051)   TGGGTGCACGAGTGGGTTACATCGAACTGGATCTCAACAGCGGTAAGATC
                            7101                                                   7150
IL13(EQ)41BBZeta   (6702)   CTTGAGAGTTTTCGCCCCGAAGAACGTTTTCCAATGATGAGCACTTTTAA
CD19Rop_epHIV7     (5919)   CTTGAGAGTTTTCGCCCCGAAGAACGTTTTCCAATGATGAGCACTTTTAA
      Consensus    (7101)   CTTGAGAGTTTTCGCCCCGAAGAACGTTTTCCAATGATGAGCACTTTTAA
                            7151                                                   7200
IL13(EQ)41BBZeta   (6752)   AGTTCTGCTATGTGGCGCGGTATTATCCCGTATTGACGCCGGGCAAGAGC
CD19Rop_epHIV7     (5969)   AGTTCTGCTATGTGGCGCGGTATTATCCCGTATTGACGCCGGGCAAGAGC
      Consensus    (7151)   AGTTCTGCTATGTGGCGCGGTATTATCCCGTATTGACGCCGGGCAAGAGC
                            7201                                                   7250
IL13(EQ)41BBZeta   (6802)   AACTCGGTCGCCGCATACACTATTCTCAGAATGACTTGGTTGAGTACTCA
CD19Rop_epHIV7     (6019)   AACTCGGTCGCCGCATACACTATTCTCAGAATGACTTGGTTGAGTACTCA
      Consensus    (7201)   AACTCGGTCGCCGCATACACTATTCTCAGAATGACTTGGTTGAGTACTCA
                            7251                                                   7300
IL13(EQ)41BBZeta   (6852)   CCAGTCACAGAAAAGCATCTTACGGATGGCATGACAGTAAGAGAATTATG
CD19Rop_epHIV7     (6069)   CCAGTCACAGAAAAGCATCTTACGGATGGCATGACAGTAAGAGAATTATG
      Consensus    (7251)   CCAGTCACAGAAAAGCATCTTACGGATGGCATGACAGTAAGAGAATTATG
                            7301                                                   7350
IL13(EQ)41BBZeta   (6902)   CAGTGCTGCCATAACCATGAGTGATAACACTGCGGCCAACTTACTTCTGA
CD19Rop_epHIV7     (6119)   CAGTGCTGCCATAACCATGAGTGATAACACTGCGGCCAACTTACTTCTGA
```

FIGURE 18L

```
      Consensus  (7301)  CAGTGCTGCCATAACCATGAGTGATAACACTGCGGCCAACTTACTTCTGA
                         7351                                             7400
IL13(EQ)41BBZeta  (6952)  CAACGATCGGAGGACCGAAGGAGCTAACCGCTTTTTTGCACAACATGGGG
   CD19Rop_epHIV7 (6169)  CAACGATCGGAGGACCGAAGGAGCTAACCGCTTTTTTGCACAACATGGGG
      Consensus  (7351)  CAACGATCGGAGGACCGAAGGAGCTAACCGCTTTTTTGCACAACATGGGG
                         7401                                             7450
IL13(EQ)41BBZeta  (7002)  GATCATGTAACTCGCCTTGATCGTTGGGAACCGGAGCTGAATGAAGCCAT
   CD19Rop_epHIV7 (6219)  GATCATGTAACTCGCCTTGATCGTTGGGAACCGGAGCTGAATGAAGCCAT
      Consensus  (7401)  GATCATGTAACTCGCCTTGATCGTTGGGAACCGGAGCTGAATGAAGCCAT
                         7451                                             7500
IL13(EQ)41BBZeta  (7052)  ACCAAACGACGAGCGTGACACCACGATGCCTGTAGCAATGGCAACAACGT
   CD19Rop_epHIV7 (6269)  ACCAAACGACGAGCGTGACACCACGATGCCTGTAGCAATGGCAACAACGT
      Consensus  (7451)  ACCAAACGACGAGCGTGACACCACGATGCCTGTAGCAATGGCAACAACGT
                         7501                                             7550
IL13(EQ)41BBZeta  (7102)  TGCGCAAACTATTAACTGGCGAACTACTTACTCTAGCTTCCCGGCAACAA
   CD19Rop_epHIV7 (6319)  TGCGCAAACTATTAACTGGCGAACTACTTACTCTAGCTTCCCGGCAACAA
      Consensus  (7501)  TGCGCAAACTATTAACTGGCGAACTACTTACTCTAGCTTCCCGGCAACAA
                         7551                                             7600
IL13(EQ)41BBZeta  (7152)  TTAATAGACTGGATGGAGGCGGATAAAGTTGCAGGACCACTTCTGCGCTC
   CD19Rop_epHIV7 (6369)  TTAATAGACTGGATGGAGGCGGATAAAGTTGCAGGACCACTTCTGCGCTC
      Consensus  (7551)  TTAATAGACTGGATGGAGGCGGATAAAGTTGCAGGACCACTTCTGCGCTC
                         7601                                             7650
IL13(EQ)41BBZeta  (7202)  GGCCCTTCCGGCTGGCTGGTTTATTGCTGATAAATCTGGAGCCGGTGAGC
   CD19Rop_epHIV7 (6419)  GGCCCTTCCGGCTGGCTGGTTTATTGCTGATAAATCTGGAGCCGGTGAGC
      Consensus  (7601)  GGCCCTTCCGGCTGGCTGGTTTATTGCTGATAAATCTGGAGCCGGTGAGC
                         7651                                             7700
IL13(EQ)41BBZeta  (7252)  GTGGGTCTCGCGGTATCATTGCAGCACTGGGGCCAGATGGTAAGCCCTCC
   CD19Rop_epHIV7 (6469)  GTGGGTCTCGCGGTATCATTGCAGCACTGGGGCCAGATGGTAAGCCCTCC
      Consensus  (7651)  GTGGGTCTCGCGGTATCATTGCAGCACTGGGGCCAGATGGTAAGCCCTCC
                         7701                                             7750
IL13(EQ)41BBZeta  (7302)  CGTATCGTAGTTATCTACACGACGGGGAGTCAGGCAACTATGGATGAACG
   CD19Rop_epHIV7 (6519)  CGTATCGTAGTTATCTACACGACGGGGAGTCAGGCAACTATGGATGAACG
      Consensus  (7701)  CGTATCGTAGTTATCTACACGACGGGGAGTCAGGCAACTATGGATGAACG
                         7751                                             7800
IL13(EQ)41BBZeta  (7352)  AAATAGACAGATCGCTGAGATAGGTGCCTCACTGATTAAGCATTGGTAAC
   CD19Rop_epHIV7 (6569)  AAATAGACAGATCGCTGAGATAGGTGCCTCACTGATTAAGCATTGGTAAC
      Consensus  (7751)  AAATAGACAGATCGCTGAGATAGGTGCCTCACTGATTAAGCATTGGTAAC
                         7801                                             7850
IL13(EQ)41BBZeta  (7402)  TGTCAGACCAAGTTTACTCATATATACTTTAGATTGATTTAAAACTTCAT
   CD19Rop_epHIV7 (6619)  TGTCAGACCAAGTTTACTCATATATACTTTAGATTGATTTAAAACTTCAT
      Consensus  (7801)  TGTCAGACCAAGTTTACTCATATATACTTTAGATTGATTTAAAACTTCAT
                         7851                                             7900
IL13(EQ)41BBZeta  (7452)  TTTTAATTTAAAAGGATCTAGGTGAAGATCCTTTTTGATAATCTCATGAC
   CD19Rop_epHIV7 (6669)  TTTTAATTTAAAAGGATCTAGGTGAAGATCCTTTTTGATAATCTCATGAC
      Consensus  (7851)  TTTTAATTTAAAAGGATCTAGGTGAAGATCCTTTTTGATAATCTCATGAC
                         7901                                             7950
IL13(EQ)41BBZeta  (7502)  CAAAATCCCTTAACGTGAGTTTTCGTTCCACTGAGCGTCAGACCCCGTAG
   CD19Rop_epHIV7 (6719)  CAAAATCCCTTAACGTGAGTTTTCGTTCCACTGAGCGTCAGACCCCGTAG
      Consensus  (7901)  CAAAATCCCTTAACGTGAGTTTTCGTTCCACTGAGCGTCAGACCCCGTAG
                         7951                                             8000
IL13(EQ)41BBZeta  (7552)  AAAAGATCAAAGGATCTTCTTGAGATCCTTTTTTTCTGCGCGTAATCTGC
   CD19Rop_epHIV7 (6769)  AAAAGATCAAAGGATCTTCTTGAGATCCTTTTTTTCTGCGCGTAATCTGC
      Consensus  (7951)  AAAAGATCAAAGGATCTTCTTGAGATCCTTTTTTTCTGCGCGTAATCTGC
                         8001                                             8050
IL13(EQ)41BBZeta  (7602)  TGCTTGCAAACAAAAAAACCACCGCTACCAGCGGTGGTTTGTTTGCCGGA
```

FIGURE 18M

```
CD19Rop_epHIV7   (6819)  TGCTTGCAAACAAAAAAACCACCGCTACCAGCGGTGGTTTGTTTGCCGGA
    Consensus    (8001)  TGCTTGCAAACAAAAAAACCACCGCTACCAGCGGTGGTTTGTTTGCCGGA
                         8051                                              8100
IL13(EQ)41BBZeta (7652)  TCAAGAGCTACCAACTCTTTTTCCGAAGGTAACTGGCTTCAGCAGAGCGC
CD19Rop_epHIV7   (6869)  TCAAGAGCTACCAACTCTTTTTCCGAAGGTAACTGGCTTCAGCAGAGCGC
    Consensus    (8051)  TCAAGAGCTACCAACTCTTTTTCCGAAGGTAACTGGCTTCAGCAGAGCGC
                         8101                                              8150
IL13(EQ)41BBZeta (7702)  AGATACCAAATACTGTTCTTCTAGTGTAGCCGTAGTTAGGCCACCACTTC
CD19Rop_epHIV7   (6919)  AGATACCAAATACTGTTCTTCTAGTGTAGCCGTAGTTAGGCCACCACTTC
    Consensus    (8101)  AGATACCAAATACTGTTCTTCTAGTGTAGCCGTAGTTAGGCCACCACTTC
                         8151                                              8200
IL13(EQ)41BBZeta (7752)  AAGAACTCTGTAGCACCGCCTACATACCTCGCTCTGCTAATCCTGTTACC
CD19Rop_epHIV7   (6969)  AAGAACTCTGTAGCACCGCCTACATACCTCGCTCTGCTAATCCTGTTACC
    Consensus    (8151)  AAGAACTCTGTAGCACCGCCTACATACCTCGCTCTGCTAATCCTGTTACC
                         8201                                              8250
IL13(EQ)41BBZeta (7802)  AGTGGCTGCTGCCAGTGGCGATAAGTCGTGTCTTACCGGGTTGGACTCAA
CD19Rop_epHIV7   (7019)  AGTGGCTGCTGCCAGTGGCGATAAGTCGTGTCTTACCGGGTTGGACTCAA
    Consensus    (8201)  AGTGGCTGCTGCCAGTGGCGATAAGTCGTGTCTTACCGGGTTGGACTCAA
                         8251                                              8300
IL13(EQ)41BBZeta (7852)  GACGATAGTTACCGGATAAGGCGCAGCGGTCGGGCTGAACGGGGGGTTCG
CD19Rop_epHIV7   (7069)  GACGATAGTTACCGGATAAGGCGCAGCGGTCGGGCTGAACGGGGGGTTCG
    Consensus    (8251)  GACGATAGTTACCGGATAAGGCGCAGCGGTCGGGCTGAACGGGGGGTTCG
                         8301                                              8350
IL13(EQ)41BBZeta (7902)  TGCACACAGCCCAGCTTGGAGCGAACGACCTACACCGAACTGAGATACCT
CD19Rop_epHIV7   (7119)  TGCACACAGCCCAGCTTGGAGCGAACGACCTACACCGAACTGAGATACCT
    Consensus    (8301)  TGCACACAGCCCAGCTTGGAGCGAACGACCTACACCGAACTGAGATACCT
                         8351                                              8400
IL13(EQ)41BBZeta (7952)  ACAGCGTGAGCTATGAGAAAGCGCCACGCTTCCCGAAGGGAGAAAGGCGG
CD19Rop_epHIV7   (7169)  ACAGCGTGAGCTATGAGAAAGCGCCACGCTTCCCGAAGGGAGAAAGGCGG
    Consensus    (8351)  ACAGCGTGAGCTATGAGAAAGCGCCACGCTTCCCGAAGGGAGAAAGGCGG
                         8401                                              8450
IL13(EQ)41BBZeta (8002)  ACAGGTATCCGGTAAGCGGCAGGGTCGGAACAGGAGAGCGCACGAGGGAG
CD19Rop_epHIV7   (7219)  ACAGGTATCCGGTAAGCGGCAGGGTCGGAACAGGAGAGCGCACGAGGGAG
    Consensus    (8401)  ACAGGTATCCGGTAAGCGGCAGGGTCGGAACAGGAGAGCGCACGAGGGAG
                         8451                                              8500
IL13(EQ)41BBZeta (8052)  CTTCCAGGGGGAAACGCCTGGTATCTTTATAGTCCTGTCGGGTTTCGCCA
CD19Rop_epHIV7   (7269)  CTTCCAGGGGGAAACGCCTGGTATCTTTATAGTCCTGTCGGGTTTCGCCA
    Consensus    (8451)  CTTCCAGGGGGAAACGCCTGGTATCTTTATAGTCCTGTCGGGTTTCGCCA
                         8501                                              8550
IL13(EQ)41BBZeta (8102)  CCTCTGACTTGAGCGTCGATTTTTGTGATGCTCGTCAGGGGGCGGAGCC
CD19Rop_epHIV7   (7319)  CCTCTGACTTGAGCGTCGATTTTTGTGATGCTCGTCAGGGGGCGGAGCC
    Consensus    (8501)  CCTCTGACTTGAGCGTCGATTTTTGTGATGCTCGTCAGGGGGCGGAGCC
                         8551                                              8600
IL13(EQ)41BBZeta (8152)  TATGGAAAAACGCCAGCAACGCGGCCTTTTTACGGTTCCTGGCCTTTTGC
CD19Rop_epHIV7   (7369)  TATGGAAAAACGCCAGCAACGCGGCCTTTTTACGGTTCCTGGCCTTTTGC
    Consensus    (8551)  TATGGAAAAACGCCAGCAACGCGGCCTTTTTACGGTTCCTGGCCTTTTGC
                         8601                                              8650
IL13(EQ)41BBZeta (8202)  TGGCCTTTTGCTCACATGTTCTTTCCTGCGTTATCCCCTGATTCTGTGGA
CD19Rop_epHIV7   (7419)  TGGCCTTTTGCTCACATGTTCTTTCCTGCGTTATCCCCTGATTCTGTGGA
    Consensus    (8601)  TGGCCTTTTGCTCACATGTTCTTTCCTGCGTTATCCCCTGATTCTGTGGA
                         8651                                              8700
IL13(EQ)41BBZeta (8252)  TAACCGTATTACCGCCTTTGAGTGAGCTGATACCGCTCGCCGCAGCCGAA
CD19Rop_epHIV7   (7469)  TAACCGTATTACCGCCTTTGAGTGAGCTGATACCGCTCGCCGCAGCCGAA
    Consensus    (8651)  TAACCGTATTACCGCCTTTGAGTGAGCTGATACCGCTCGCCGCAGCCGAA
                         8701                                              8750
```

FIGURE 18N

```
IL13(EQ)41BBZeta  (8302)  CGACCGAGCGCAGCGAGTCAGTGAGCGAGGAAGCGGAAGAGCGCCCAATA
CD19Rop_epHIV7    (7519)  CGACCGAGCGCAGCGAGTCAGTGAGCGAGGAAGCGGAAGAGCGCCCAATA
     Consensus    (8701)  CGACCGAGCGCAGCGAGTCAGTGAGCGAGGAAGCGGAAGAGCGCCCAATA
                          8751                                           8800
IL13(EQ)41BBZeta  (8352)  CGCAAACCGCCTCTCCCCGCGCGTTGGCCGATTCATTAATGCAGCTGGCA
CD19Rop_epHIV7    (7569)  CGCAAACCGCCTCTCCCCGCGCGTTGGCCGATTCATTAATGCAGCTGGCA
     Consensus    (8751)  CGCAAACCGCCTCTCCCCGCGCGTTGGCCGATTCATTAATGCAGCTGGCA
                          8801                                           8850
IL13(EQ)41BBZeta  (8402)  CGACAGGTTTCCCGACTGGAAAGCGGGCAGTGAGCGCAACGCAATTAATG
CD19Rop_epHIV7    (7619)  CGACAGGTTTCCCGACTGGAAAGCGGGCAGTGAGCGCAACGCAATTAATG
     Consensus    (8801)  CGACAGGTTTCCCGACTGGAAAGCGGGCAGTGAGCGCAACGCAATTAATG
                          8851                                           8900
IL13(EQ)41BBZeta  (8452)  TGAGTTAGCTCACTCATTAGGCACCCCAGGCTTTACACTTTATGCTTCCG
CD19Rop_epHIV7    (7669)  TGAGTTAGCTCACTCATTAGGCACCCCAGGCTTTACACTTTATGCTTCCG
     Consensus    (8851)  TGAGTTAGCTCACTCATTAGGCACCCCAGGCTTTACACTTTATGCTTCCG
                          8901                                           8950
IL13(EQ)41BBZeta  (8502)  GCTCGTATGTTGTGTGGAATTGTGAGCGGATAACAATTTCACACAGGAAA
CD19Rop_epHIV7    (7719)  GCTCGTATGTTGTGTGGAATTGTGAGCGGATAACAATTTCACACAGGAAA
     Consensus    (8901)  GCTCGTATGTTGTGTGGAATTGTGAGCGGATAACAATTTCACACAGGAAA
                          8951                                           9000
IL13(EQ)41BBZeta  (8552)  CAGCTATGACCATGATTACGCCAAGCTCGAAATTAACCCTCACTAAAGGG
CD19Rop_epHIV7    (7769)  CAGCTATGACCATGATTACGCCAAGCTCGAAATTAACCCTCACTAAAGGG
     Consensus    (8951)  CAGCTATGACCATGATTACGCCAAGCTCGAAATTAACCCTCACTAAAGGG
                          9001                                           9050
IL13(EQ)41BBZeta  (8602)  AACAAAAGCTGGAGCTCCACCGCGGTGGCGGCCTCGAGGTCGAGATCCGG
CD19Rop_epHIV7    (7819)  AACAAAAGCTGGAGCTCCACCGCGGTGGCGGCCTCGAGGTCGAGATCCGG
     Consensus    (9001)  AACAAAAGCTGGAGCTCCACCGCGGTGGCGGCCTCGAGGTCGAGATCCGG
                          9051                                           9100
IL13(EQ)41BBZeta  (8652)  TCGACCAGCAACCATAGTCCCGCCCCTAACTCCGCCCATCCCGCCCCTAA
CD19Rop_epHIV7    (7869)  TCGACCAGCAACCATAGTCCCGCCCCTAACTCCGCCCATCCCGCCCCTAA
     Consensus    (9051)  TCGACCAGCAACCATAGTCCCGCCCCTAACTCCGCCCATCCCGCCCCTAA
                          9101                                           9150
IL13(EQ)41BBZeta  (8702)  CTCCGCCCAGTTCCGCCCATTCTCCGCCCCATGGCTGACTAATTTTTTTT
CD19Rop_epHIV7    (7919)  CTCCGCCCAGTTCCGCCCATTCTCCGCCCCATGGCTGACTAATTTTTTTT
     Consensus    (9101)  CTCCGCCCAGTTCCGCCCATTCTCCGCCCCATGGCTGACTAATTTTTTTT
                          9151                                           9200
IL13(EQ)41BBZeta  (8752)  ATTTATGCAGAGGCCGAGGCCGCCTCGGCCTCTGAGCTATTCCAGAAGTA
CD19Rop_epHIV7    (7969)  ATTTATGCAGAGGCCGAGGCCGCCTCGGCCTCTGAGCTATTCCAGAAGTA
     Consensus    (9151)  ATTTATGCAGAGGCCGAGGCCGCCTCGGCCTCTGAGCTATTCCAGAAGTA
                          9201                                           9250
IL13(EQ)41BBZeta  (8802)  GTGAGGAGGCTTTTTTGGAGGCCTAGGCTTTTGCAAAAAGCTTCGACGGT
CD19Rop_epHIV7    (8019)  GTGAGGAGGCTTTTTTGGAGGCCTAGGCTTTTGCAAAAAGCTTCGACGGT
     Consensus    (9201)  GTGAGGAGGCTTTTTTGGAGGCCTAGGCTTTTGCAAAAAGCTTCGACGGT
                          9251                                           9300
IL13(EQ)41BBZeta  (8852)  ATCGATTGGCTCATGTCCAACATTACCGCCATGTTGACATTGATTATTGA
CD19Rop_epHIV7    (8069)  ATCGATTGGCTCATGTCCAACATTACCGCCATGTTGACATTGATTATTGA
     Consensus    (9251)  ATCGATTGGCTCATGTCCAACATTACCGCCATGTTGACATTGATTATTGA
                          9301                                           9350
IL13(EQ)41BBZeta  (8902)  CTAGTTATTAATAGTAATCAATTACGGGGTCATTAGTTCATAGCCCATAT
CD19Rop_epHIV7    (8119)  CTAGTTATTAATAGTAATCAATTACGGGGTCATTAGTTCATAGCCCATAT
     Consensus    (9301)  CTAGTTATTAATAGTAATCAATTACGGGGTCATTAGTTCATAGCCCATAT
                          9351                                           9400
IL13(EQ)41BBZeta  (8952)  ATGGAGTTCCGCGTTACATAACTTACGGTAAATGGCCCGCCTGGCTGACC
CD19Rop_epHIV7    (8169)  ATGGAGTTCCGCGTTACATAACTTACGGTAAATGGCCCGCCTGGCTGACC
     Consensus    (9351)  ATGGAGTTCCGCGTTACATAACTTACGGTAAATGGCCCGCCTGGCTGACC
```

FIGURE 18O

```
                            9401                                              9450
IL13(EQ)41BBZeta    (9002) GCCCAACGACCCCCGCCCATTGACGTCAATAATGACGTATGTTCCCATAG
    CD19Rop_epHIV7  (8219) GCCCAACGACCCCCGCCCATTGACGTCAATAATGACGTATGTTCCCATAG
         Consensus  (9401) GCCCAACGACCCCCGCCCATTGACGTCAATAATGACGTATGTTCCCATAG
                            9451                                              9500
IL13(EQ)41BBZeta    (9052) TAACGCCAATAGGGACTTTCCATTGACGTCAATGGGTGGAGTATTTACGG
    CD19Rop_epHIV7  (8269) TAACGCCAATAGGGACTTTCCATTGACGTCAATGGGTGGAGTATTTACGG
         Consensus  (9451) TAACGCCAATAGGGACTTTCCATTGACGTCAATGGGTGGAGTATTTACGG
                            9501                                              9550
IL13(EQ)41BBZeta    (9102) TAAACTGCCCACTTGGCAGTACATCAAGTGTATCATATGCCAAGTACGCC
    CD19Rop_epHIV7  (8319) TAAACTGCCCACTTGGCAGTACATCAAGTGTATCATATGCCAAGTACGCC
         Consensus  (9501) TAAACTGCCCACTTGGCAGTACATCAAGTGTATCATATGCCAAGTACGCC
                            9551                                              9600
IL13(EQ)41BBZeta    (9152) CCCTATTGACGTCAATGACGGTAAATGGCCCGCCTGGCATTATGCCCAGT
    CD19Rop_epHIV7  (8369) CCCTATTGACGTCAATGACGGTAAATGGCCCGCCTGGCATTATGCCCAGT
         Consensus  (9551) CCCTATTGACGTCAATGACGGTAAATGGCCCGCCTGGCATTATGCCCAGT
                            9601                                              9650
IL13(EQ)41BBZeta    (9202) ACATGACCTTATGGGACTTTCCTACTTGGCAGTACATCTACGTATTAGTC
    CD19Rop_epHIV7  (8419) ACATGACCTTATGGGACTTTCCTACTTGGCAGTACATCTACGTATTAGTC
         Consensus  (9601) ACATGACCTTATGGGACTTTCCTACTTGGCAGTACATCTACGTATTAGTC
                            9651                                              9700
IL13(EQ)41BBZeta    (9252) ATCGCTATTACCATGGTGATGCGGTTTTGGCAGTACATCAATGGGCGTGG
    CD19Rop_epHIV7  (8469) ATCGCTATTACCATGGTGATGCGGTTTTGGCAGTACATCAATGGGCGTGG
         Consensus  (9651) ATCGCTATTACCATGGTGATGCGGTTTTGGCAGTACATCAATGGGCGTGG
                            9701                                              9750
IL13(EQ)41BBZeta    (9302) ATAGCGGTTTGACTCACGGGGATTTCCAAGTCTCCACCCCATTGACGTCA
    CD19Rop_epHIV7  (8519) ATAGCGGTTTGACTCACGGGGATTTCCAAGTCTCCACCCCATTGACGTCA
         Consensus  (9701) ATAGCGGTTTGACTCACGGGGATTTCCAAGTCTCCACCCCATTGACGTCA
                            9751                                              9800
IL13(EQ)41BBZeta    (9352) ATGGGAGTTTGTTTTGGCACCAAAATCAACGGGACTTTCCAAAATGTCGT
    CD19Rop_epHIV7  (8569) ATGGGAGTTTGTTTTGGCACCAAAATCAACGGGACTTTCCAAAATGTCGT
         Consensus  (9751) ATGGGAGTTTGTTTTGGCACCAAAATCAACGGGACTTTCCAAAATGTCGT
                            9801                                              9850
IL13(EQ)41BBZeta    (9402) AACAACTCCGCCCCATTGACGCAAATGGGCGGTAGGCGTGTACGGAATTC
    CD19Rop_epHIV7  (8619) AACAACTCCGCCCCATTGACGCAAATGGGCGGTAGGCGTGTACGGAATTC
         Consensus  (9801) AACAACTCCGCCCCATTGACGCAAATGGGCGGTAGGCGTGTACGGAATTC
                            9851                                              9900
IL13(EQ)41BBZeta    (9452) GGAGTGGCGAGCCCTCAGATCCTGCATATAAGCAGCTGCTTTTTGCCTGT
    CD19Rop_epHIV7  (8669) GGAGTGGCGAGCCCTCAGATCCTGCATATAAGCAGCTGCTTTTTGCCTGT
         Consensus  (9851) GGAGTGGCGAGCCCTCAGATCCTGCATATAAGCAGCTGCTTTTTGCCTGT
                            9901      9914
IL13(EQ)41BBZeta    (9502) ACTGGGTCTCTCTG
    CD19Rop_epHIV7  (8719) ACTGGGTCTCTCTG
         Consensus  (9901) ACTGGGTCTCTCTG
```

FIGURE 19

IL13(EmY)-CD8h3-CD8tm2-41BB-Zeta

MLLLVTSLLLCELPHPAFLLIPGPVPPSTALRLIEELVNITQNQKAPLCNGSMVWSINLTAGM

GMCSFRa signal peptide    IL13(EmY)

YCAALESLINVSGCSAIEKTQRMLSGFCPHKVSAGQFSSLHVRDTKIEVAQFVKDLLLHLKKLF

REGRFNAKPTTTPAPRPPTPAPTIASQPLSLRPEACRPAAGGAVHTRGLDFACDIYIWAPLAG

CD8hinge (48 aa)        CD8tm(2)

TCGVLLLSLVITLYKRGRKKLLYIFKQPFMRPVQTTQEEDGCSCRFPEEEEGGCELGGGRVKFS 4-1BB cyto         CD3ζ

RSADAPAYQQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

GMCSFRa signal peptide
IL13(EmY)
CD8hinge
CD8 transmembrane (2)
4-1BB cyto
(Gly)3
Zeta

FIGURE 20

IL13(EmY)-CD8h3-CD28tm-CD28gg-41BB-Zeta

<u>MLLLVTSLLLCELPHPAFLLIPG</u>PVPPSTALR<u></u>LIEELVNITQNQKAPLCNGSMVWSINLTAGM GMCSFRa signal peptide       IL13(EmY)

YCAALESLINVSGCSAIEKTQRMLSGFCPHKVSAGQFSSLHVRDTKIEVAQFVKDLLLHLKKLF

REGRFN<u>AKPTTTPAPRPPTPAPTIASQPLSLRPEACRPAAGGAVHTRGLDFACD</u><u>FWVLVVVG</u>

CD8 hinge (48 aa)                                         CD28tm

<u>GVLACYSLLVTVAFIIFWV</u><u>RSKRSRGGHSDYMNMTPRRPGPTRKHYQPYAPPRDFAAYRSG</u>

CD28gg

<u>GGKRGRKKLLYIFKQPFMRPVQTTQEEDGCSCRFPEEEEGGC</u>ELGGG<u>RVKFSRSADAPAYQ</u>

4-1BB cyto                                               CD3ζ

<u>QGQNQLYNELNLGRREEYDVLDKRRGRDPEMGGKPRRKNPQEGLYNELQKDKMAEAYSEI</u>

<u>GMKGERRRGKGHDGLYQGLSTATKDTYDALHMQALPPR</u>

GMCSFRa signal peptide
IL13(EmY)
CD8hinge
CD28 transmembrane
CD28gg
4-1BB cyto
(Gly)3
Zeta

FIGURE 21

IL13(EmY)-IgG4(HL-CH3)-CD4tm-41BB-Zeta

<u>MLLLVTSLLLCELPHPAFLLIPGPVPPSTALR</u><u>LIEELVNITQNQKAPLCNGSMVWSINLTAGM</u>
GMCSFRa signal peptide         IL13(EmY)

<u>YCAALESLINVSGCSAIEKTQRMLSGFCPHKVSAGQFSSLHVRDTKIEVAQFVKDLLLHLKKLF</u>

<u>REGRFNESKYGPPCP</u><u>CPGGGSSGGGSGGQPREPQVYTLPPSQEEMTKNQVSLTCLVKGFY</u>
    IgG4Hinge      Linker        IgG4-CH3

<u>PSDIAVEWESNGQPENNYKTTPPVLDSDGSFFLYSRLTVDKSRWQEGNVFSCSVMHEALHN</u>

<u>HYTQKSLSLSLGKMALIVLGGVAGLLLFIGLGIFF</u><u>KRGRKKLLYIFKQPFMRPVQTTQEEDGCS</u>
         CD4 tm                      4-1BB cyto <u>CRFPEEEEGGCELGGG</u><u>RVKFSRSADAPAYQQGQNQLYNELNLGRREEYDVLDKRRGRDPE</u>
                  CD3ζ

<u>MGGKPRRKNPQEGLYNELQKDKMAEAYSEIGMKGERRRGKGHDGLYQGLSTATKDTYDA</u>

<u>LHMQALPPR</u>

GMCSFRa signal peptide
IL13(EmY)
IgG4Hinge
Linker
IgG4-Fc-CH3
CD4 transmembrane
4-1BB cyto
(Gly)3
Zeta

FIGURE 22

IL13(EmY)-IgG4(L235E,N297Q)-CD8tm-41BB-Zeta

<u>MLLLVTSLLLCELPHPAFLLIPGPVPPSTALR</u><u>LIEELVNITQNQKAPLCNGSMVWSINLTAGM</u>
GMCSFRa signal peptide      IL13(EmY)

<u>YCAALESLINVSGCSAIEKTQRMLSGFCPHKVSAGQFSSLHVRDTKIEVAQFVKDLLLHLKKLF</u>

<u>REGRFNESKYGPPCP</u><u>CPAPEFEGGPSVFLFPPKPKDTLMISRTPEVTCVVVDVSQEDPEVQF</u>
    IGgG4-Fc(SmP)

<u>NWYVDGVEVHNAKTKPREEQFQSTYRVVSVLTVLHQDWLNGKEYKCKVSNKGLPSSIEKTIS</u>

<u>KAKGQPREPQVYTLPPSQEEMTKNQVSLTCLVKGFYPSDIAVEWESNGQPENNYKTTPPVL</u>

<u>DSDGSFFLYSRLTVDKSRWQEGNVFSCSVMHEALHNHYTQKSLSLSLGKIYIWAPLAGTCGV</u>
                                                                                                                                  CD8 tm

<u>LLLSLVIT</u><u>KRGRKKLLYIFKQPFMRPVQTTQEEDGCSCRFPEEEEGGCEL</u>GGGRVKFSRSADAP
    4-1BB cyto                                                                                     CD3ζ

AYQQGQNQLYNELNLGRREEYDVLDKRRGRDPEMGGKPRRKNPQEGLYNELQKDKMAEA

YSEIGMKGERRRGKGHDGLYQGLSTATKDTYDALHMQALPPR

GMCSFRa signal peptide
IL13(EmY)
IgG4-Fc(SmP)
CD8 transmembrane
4-1BB cyto
(Gly)3
Zeta

FIGURE 23

IL13(EmY)-Linker-CD28tm-CD28gg-41BB-Zeta

<u>MLLLVTSLLLCELPHPAFLLIP</u>GPVPPSTALR░LIEELVNITQNQKAPLCNGSMVWSINLTAGM
GMCSFRa signal peptide     IL13(EmY)

YCAALESLINVSGCSAIEKTQRMLSGFCPHKVSAGQFSSLHVRDTKIEVAQFVKDLLLHLKKLF

REGRFN<u>GGGSSGGGSG</u>MFWVLVVVGGVLACYSLLVTVAFIIFWV<u>RSKRSRGGHSDYMNM</u>
     Linker     CD28(M) tm     CD28gg <u>TPRRPGPTRKHYQPYAPPRDFAAYRS</u>GGG<u>KRGRKKLLYIFKQPFMRPVQTTQEEDGCSCRFP</u>
     4-1BB cyto <u>EEEEGGCEL</u>GGG<u>RVKFSRSADAPAYQQGQNQLYNELNLGRREEYDVLDKRRGRDPEMGGK</u>
     CD3ζ

<u>PRRKNPQEGLYNELQKDKMAEAYSEIGMKGERRRGKGHDGLYQGLSTATKDTYDALHMQ</u>

<u>ALPPR</u>

GMCSFRa signal peptide
IL13(EmY)
Linker
CD28(M) transmembrane
CD28gg
4-1BB cyto
(Gly)3
Zeta

FIGURE 24

IL13(EmY)-HL-CD28m-CD28gg-41BB-Zeta

<u>MLLLVTSLLLCELPHPAFLLIPG</u>PVPPSTALR:LIEELVNITQNQKAPLCNGSMVWSINLTAGM
GMCSFRa signal peptide           IL13(EmY)

YCAALESLINVSGCSAIEKTQRMLSGFCPHKVSAGQFSSLHVRDTKIEVAQFVKDLLLHLKKLF

REGRFN<u>ESKYGPPCP:CPGGGSSGGGSG</u><u>MFWVLVVVGGVLACYSLLVTVAFIIFWV</u>RSKRS
      IgG4Hinge        Linker           CD28(M) tm
CD28gg RGGHSDYMNMTPRRPGPTRKHYQPYAPPRDFAAYRS<u>GGG</u>KRGRKKLLYIFKQPFMRPVQT
                                              4-1BB cyto TQEEDGCSCRFPEEEEGGCEL<u>GGG</u>RVKFSRSADAPAYQQGQNQLYNELNLGRREEYDVLDK
                           CD3ζ

RRGRDPEMGGKPRRKNPQEGLYNELQKDKMAEAYSEIGMKGERRRGKGHDGLYQGLSTA

TKDTYDALHMQALPPR

GMCSFRa signal peptide
IL13(EmY)
IgG4Hinge
Linker
CD28(M) transmembrane
CD28gg
4-1BB cyto
(Gly)3
Zeta

Figure 25

IL13(EmY)-IgG4(HL-CH3)-CD28tm-CD28gg-41BB-Zeta

<u>MLLLVTSLLLCELPHPAFLLIPGPVPPSTALR</u><u>LIEELVNITQNQKAPLCNGSMVWSINLTAGM</u>
  GMCSFRa signal peptide     IL13(EmY)

<u>YCAALESLINVSGCSAIEKTQRMLSGFCPHKVSAGQFSSLHVRDTKIEVAQFVKDLLLHLKKLF</u>

<u>REGRFN</u><u>ESKYGPPCP</u><u>CPGGGSSGGGS</u><u>GGQPREPQVYTLPPSQEEMTKNQVSLTCLVKGFY</u>
         IgG4Hinge       Linker        IgG4 CH3

<u>PSDIAVEWESNGQPENNYKTTPPVLDSDGSFFLYSRLTVDKSRWQEGNVFSCSVMHEALHN</u>

<u>HYTQKSLSLSLGK</u><u>MFWVLVVVGGVLACYSLLVTVAFIIFWV</u><u>RSKRSRGGHSDYMNMTPRRP</u>
              CD28(M) tm                        CD28gg

<u>GPTRKHYQPYAPPRDFAAYRS</u><u>GGGKRGRKKLLYIFKQPFMRPVQTTQEEDGCSCRFPEEEEG</u>
                                4-1BB cyto <u>GCELGGGRVKFSRSADAPAYQQGQNQLYNELNLGRREEYDVLDKRRGRDPEMGGKPRRK</u>
      CD3ζ

<u>NPQEGLYNELQKDKMAEAYSEIGMKGERRRGKGHDGLYQGLSTATKDTYDALHMQALPP</u>

<u>R</u>

GMCSFRa signal peptide
IL13(EmY)
IgG4Hinge
Linker
IgG4 CH3
CD28 transmembrane
CD28gg
4-1BB cyto
(Gly)3
Zeta

FIGURE 26

IL13(EmY)-IgG4(L235E,N297Q)-CD28tm-CD28gg-41BB-Zeta

<u>MLLLVTSLLLCELPHPAFLLIPGPVPPSTALR</u>░<u>LIEELVNITQNQKAPLCNGSMVWSINLTAGM</u>
GMCSFRa signal peptide      IL13(EmY)

<u>YCAALESLINVSGCSAIEKTQRMLSGFCPHKVSAGQFSSLHVRDTKIEVAQFVKDLLLHLKKLF</u>

<u>REGRFNESKYGPPCP</u>░<u>CPAPEFEGGPSVFLFPPKPKDTLMISRTPEVTCVVVDVSQEDPEVQF</u>
           IgG4-Fc(L235E,N297Q)

<u>NWYVDGVEVHNAKTKPREEQFQSTYRVVSVLTVLHQDWLNGKEYKCKVSNKGLPSSIEKTIS</u>

<u>KAKGQPREPQVYTLPPSQEEMTKNQVSLTCLVKGFYPSDIAVEWESNGQPENNYKTTPPVL</u>

<u>DSDGSFFLYSRLTVDKSRWQEGNVFSCSVMHEALHNHYTQKSLSLSLGKMFWVLVVVGGV</u>
                                                                                  CD28(M) tm
<u>LACYSLLVTVAFIIFWV</u><u>RSKRSRGGHSDYMNMTPRRPGPTRKHYQPYAPPRDFAAYRS</u>GGG
                           CD28gg

<u>KRGRKKLLYIFKQPFMRPVQTTQEEDGCSCRFPEEEEGGCEL</u>GGG<u>RVKFSRSADAPAYQQG</u>
      4-1BB cyto                                                          CD3ζ

<u>QNQLYNELNLGRREEYDVLDKRRGRDPEMGGKPRRKNPQEGLYNELQKDKMAEAYSEIG</u>

<u>MKGERRRGKGHDGLYQGLSTATKDTYDALHMQALPPR</u>

GMCSFRa signal peptide
IL13(EmY)
IgG4-Fc(L235E,N297Q)
CD28 (M) transmembrane
CD28gg
(Gly)3
4-1BB cyto
(Gly)3
Zeta

FIGURE 27

IL13(EmY)-CD8h3-CD8tm-41BB-Zeta

<u>MLLLVTSLLLCELPHPAFLLIP</u>GPVPPSTALR▓LIEELVNITQNQKAPLCNGSMVWSINLTAGM

GMCSFRa signal peptide      IL13(EmY)

YCAALESLINVSGCSAIEKTQRMLSGFCPHKVSAGQFSSLHVRDTKIEVAQFVKDLLLHLKKLF

REGRFN<u>AKPTTTPAPRPPTPAPTIASQPLSLRPEACRPAAGGAVHTRGLDFAC</u>DIYIWAPLAG

CD8hinge (48 aa)                            CD8tm

TCGVLLLSLVIT<u>GGG</u>KRGRKKLLYIFKQPFMRPVQTTQEEDGCSCRFPEEEEGGCEL<u>GGG</u>RVK 4-1BB cyto                               CD3ζ

FSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

GMCSFRa signal peptide
IL13(EmY)
CD8hinge
CD8 transmembrane
(Gly)3
4-1BB cyto
(Gly)3
Zeta

COSTIMULATORY CHIMERIC ANTIGEN RECEPTOR T CELLS TARGETING IL13Rα2

CLAIM OF PRIORITY

This application claims priority under 35 U.S.C. § 365(c) to International Patent Application PCT/US2015/051089, filed on Sep. 18, 2015, which claims priority under 35 U.S.C. § 119(e) to provisional U.S. Patent Application 62/053,068, filed on Sep. 19, 2014, the entire contents of each which are hereby incorporated by reference.

BACKGROUND

Tumor-specific T cell based immunotherapies, including therapies employing engineered T cells, have been investigated for anti-tumor treatment. In some cases the T cells used in such therapies do not remain active in vivo for a long enough period. In some cases, the tumor-specificity of the T cells is relatively low. Therefore, there is a need in the art for tumor-specific cancer therapies with longer term anti-tumor functioning.

Malignant gliomas (MG), which include anaplastic astrocytoma (AA-grade III) and glioblastoma (GBM-grade IV), have an incidence rate of approximately 20,000 new cases diagnosed annually in the United States. According to the American Brain Tumor Association total prevalence of individuals living with a malignant brain tumor, based on United States 2010 census data, is roughly 140,000 persons. Although MG is a rare disease, it is highly aggressive and heterogeneous with respect to its malignant behavior and nearly uniformly lethal. Current standard-of-care therapies for high-grade MG yield only short term benefits, and these brain tumors are virtually incurable. Indeed, even with modern surgical and radiotherapeutic techniques, which often exacerbate the already severe morbidities imposed by location in the central nervous system (CNS), the 5-year survival rates are quite low. Furthermore, for the majority of patients who relapse with disease, there are few therapeutic options. Thus, there is a significant need for more effective therapies, particularly for those patients that have recurred/progressed following frontline therapies, and participation of this patient population in clinical trials is warranted.

Adoptive T cell therapy (ACT) utilizing chimeric antigen receptor (CAR) engineered T cells may provide a safe and effective way to reduce recurrence rates of MG, since CAR T cells can be engineered to specifically recognize antigenically-distinct tumor populations (Cartellieri et al. 2010 *J Biomed Biotechnol* 2010:956304; Ahmed et al. 2010 *Clin Cancer Res* 16:474; Sampson et al. 2014 *Clin Cancer Res* 20:972; Brown et al. 2013 *Clin Cancer Res* 2012 18:2199; Chow et al. 2013 *Mol Ther* 21:629), and T cells can migrate through the brain parenchyma to target and kill infiltrative malignant cells (Hong et al. 2010 *Clin Cancer Res* 16:4892; Brown et al. 2007 *J Immunol* 179:3332; Hong et al. 2010 *Clin Cancer Res* 16:4892; Yaghoubi 2009 *Nat Clin PRact Oncol* 6:53). Preclinical studies have demonstrated that IL13Rα2-targeting CAR+ T cells exhibit potent major histocompatibility complex (MHC)-independent, IL13Rα2-specific cytolytic activity against both stem-like and differentiated glioma cells, and induce regression of established glioma xenografts in vivo (Kahlon et al. 2004 *Cancer Res* 64:9160; Brown et al. 2012 *Clin Cancer Res* 18:2199).

SUMMARY

Described herein are chimeric transmembrane immunoreceptors (chimeric antigen receptors or "CARs") which comprise an extracellular domain, a transmembrane region and an intracellular signaling domain. The extracellular domain is made up of an IL-13 ligand that binds interleukin-13Rα2 (IL13Rα2) and, optionally, a spacer, comprising, for example a portion human Fc domain. The transmembrane portion includes a CD4 transmembrane domain, a CD8 transmembrane domain, a CD28 transmembrane domain, a CD3 transmembrane domain or a 4IBB transmembrane domain. The intracellular signaling domain includes the signaling domain from the zeta chain of the human CD3 complex (CD3ζ) and one or more costimulatory domains, e.g., a 4-1BB costimulatory domain. The extracellular domain enables the CAR, when expressed on the surface of a T cell, to direct T cell activity to those cells expressing IL13Rα2, a receptor expressed on the surface of tumor cells, including glioma. Importantly, the IL13Rα2 binding portion of the CAR includes an amino acid modification, such as an E13Y mutation, that increases binding specificity. The inclusion of a costimulatory domain, such as the 4-1BB (CD137) costimulatory domain in series with CD3ζ in the intracellular region enables the T cell to receive co-stimulatory signals. T cells, for example, patient-specific, autologous T cells can be engineered to express the CARs described herein and the engineered cells can be expanded and used in ACT. Various T cell subsets can be used. In addition, the CAR can be expressed in other immune cells such as NK cells. Where a patient is treated with an immune cell expressing a CAR described herein the cell can be an autologous or allogenic T cell. In some cases the cells used are CD4+ and CD8+ central memory T cells ($T_{CM}$), which are CD45RO+CD62L+, and the use of such cells can improve long-term persistence of the cells after adoptive transfer compared to the use of other types of patient-specific T cells.

Described herein is a nucleic acid molecule encoding a chimeric antigen receptor (CAR)r, wherein the chimeric antigen receptor comprises: human IL-13 or a variant thereof having 1-10 (e.g., 1 or 2) amino acid modifications; a transmembrane domain selected from: a CD4 transmembrane domain or variant thereof having 1-10 (e.g., 1 or 2) amino acid modifications, a CD8 transmembrane domain or variant thereof having 1-10 (e.g., 1 or 2) amino acid modifications, a CD28 transmembrane domain or a variant thereof having 1-10 (e.g., 1 or 2) amino acid modifications, and a CD3ζ transmembrane domain or a variant thereof having 1-10 (e.g., 1 or 2) amino acid modifications; a costimulatory domain; and CD3 signaling domain of a variant thereof having 1-10 (e.g., 1 or 2) amino acid modifications.

In various embodiments the costimulatory domain is selected from the group consisting of: a CD28 costimulatory domain or a variant thereof having 1-10 (e.g., 1 or 2) amino acid modifications, a 4-IBB costimulatory domain or a variant thereof having 1-10 (e.g., 1 or 2) amino acid modifications and an OX40 costimulatory domain or a variant thereof having 1-10 (e.g., 1 or 2) amino acid modifications. In certain embodiments, a 4IBB costimulatory domain or a variant thereof having 1-10 (e.g., 1 or 2) amino acid modifications in present.

Additional embodiment the CAR comprises: a variant of a human IL13 having 1-10 amino acid modification that increase binding specificity for IL13Rα2 versus IL13Rα1; the human IL-13 or variant thereof is an IL-13 variant comprising the amino acid sequence of SEQ ID NO:3 with 1 to 5 amino acid modifications, provided that the amino acid at position 11 of SEQ ID NO:3 other than E; two different costimulatory domains selected from the group consisting of: a CD28 costimulatory domain or a variant thereof having 1-10 (e.g., 1 or 2) amino acid modifications, a 4IBB costimulatory domain or a variant thereof having 1-10 (e.g., 1 or 2) amino acid modifications and an OX40 costimulatory domain or a variant thereof having 1-10 (e.g., 1 or 2) amino acid modifications; two different costimulatory domains selected from the group consisting of: a CD28 costimulatory domain or a variant thereof having 1-2 amino acid modifications, a 4IBB costimulatory domain or a variant thereof having 1-2 amino acid modifications and an OX40 costimulatory domain or a variant thereof having 1-2 amino acid modifications; human IL-13 or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3ζ transmembrane domain or a variant thereof having 1-2 amino acid modifications; a costimulatory domain; and CD3ζ signaling domain of a variant thereof having 1-2 amino acid modifications; a spacer region located between the IL-13 or variant thereof and the transmembrane domain (e.g., the spacer region comprises an amino acid sequence selected from the group consisting of SEQ ID NO: 4, 14-20, 50 and 52); the spacer comprises an IgG hinge region; the spacer region comprises 10-150 amino acids; the 4-1BB signaling domain comprises the amino acid sequence of SEQ ID NO:6; the CD3ζ signaling domain comprises the amino acid sequence of SEQ ID NO:7; and a linker of 3 to 15 amino acids that is located between the costimulatory domain and the CD3 ζ signaling domain or variant thereof. In certain embodiments where there are two costimulatory domains, one is an 4-IBB costimulatory domain and the other a costimulatory domain selected from: CD28 and CD28gg In some embodiments: nucleic acid molecule expresses a polypeptide comprising an amino acid sequence selected from SEQ ID NOs: 10, 31-48 and 52; the chimeric antigen receptor comprises a IL-13/IgG4/CD4t/41-BB region comprising the amino acid of SEQ ID NO:11 and a CD3 signaling domain comprising the amino acid sequence of SEQ ID NO:7; and the chimeric antigen receptor comprises the amino acid sequence of SEQ ID NOs: 10, 31-48 and 52.

Also disclosed is a population of human T cells transduced by a vector comprising an expression cassette encoding a chimeric antigen receptor, wherein chimeric antigen receptor comprises: human IL-13 or a variant thereof having 1-10 amino acid modifications; a transmembrane domain selected from: a CD4 transmembrane domain or variant thereof having 1-10 amino acid modifications, a CD8 transmembrane domain or variant thereof having 1-10 amino acid modifications, a CD28 transmembrane domain or a variant thereof having 1-10 amino acid modifications, and a CD3ζ transmembrane domain or a variant thereof having 1-10 amino acid modifications; a costimulatory domain; and CD3ζ signaling domain of a variant thereof having 1-10 amino acid modifications. In various embodiments: the population of human T cells comprise a vector expressing a chimeric antigen receptor comprising an amino acid sequence selected from SEQ ID NOs: 10, 31-48 and 52; the population of human T cells are comprises of central memory T cells (Tcm cells) (e.g., at least 20%, 30%, 40%, 50% 60%, 70%, 80% of the cells are Tcm cells; at least 15%, 20%, 25%, 30%, 35% of the Tcm cells are CD4+ and at least 15%, 20%, 25%, 30%, 35% of the Tcm cells are CD8+ cells).

Also described is a method of treating cancer in a patient comprising administering a population of autologous or allogeneic human T cells (e.g., autologous or allogenic T cells comprising Tcm cells, e.g., at least 20%, 30%, 40%, 50% 60%, 70%, 80% of the cells are Tcm cells; at least 15%, 20%, 25%, 30%, 35% of the Tcm cells are CD4+ and at least 15%, 20%, 25%, 30%, 35% of the Tcm cells are CD8+ cells) transduced by a vector comprising an expression cassette encoding a chimeric antigen receptor, wherein chimeric antigen receptor comprises an amino acid sequence selected from SEQ ID NOs: 10, 31-48 and 52. In various embodiments: the population of human T cells comprise central memory T cells; the cancer is glioblastoma; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 10, 31-48 and 52.

Also described is: a nucleic acid molecule encoding an polypeptide comprising an amino acid sequence that is at least 95% identical to an amino acid sequence selected from SEQ ID NO:10 and SEQ ID NOs: 10, 31-48 and 52; a nucleic acid molecule encoding an polypeptide comprising an amino acid sequence that is identical to an amino acid sequence selected from SEQ ID NO: 10, 31-48 and 52 except for the presence of no more than 5 amino acid substitutions, deletions or insertions; a nucleic acid molecule encoding an polypeptide comprising an amino acid sequence that is identical to an amino acid sequence selected from SEQ ID NO:10 and SEQ ID NOs: 10, 31-48 and 52 except for the presence of no more than 5 amino acid substitutions; and a nucleic acid molecule encoding an polypeptide comprising an amino acid sequence that is identical to an amino acid sequence selected from SEQ ID NO:10 and SEQ ID NOs: 10, 31-48 and 52 except for the presence of no more than 2 amino acid substitutions.

Certain CAR described herein, for example, the IL13(EQ) BBζ CAR and the IL13(EQ)CD28-BBζ CAR, have certain beneficial characteristics compared to certain other IL13-targeted CAR. For example, they have improved selectivity for IL13Rα, elicit lower Th2 cytokine production, particularly lower IL13 production.

T cells expressing a CAR targeting IL13Rα2 can be useful in treatment of cancers such as glioblastoma, as well as other cancer that expresses IL13Rα2 which include but are not limited to medulloblastoma, breast cancer, head and neck cancer, kidney cancer, ovarian cancer and Kaposi's sarcoma. Thus, this disclosure includes methods for treating cancer using T cells expressing a CAR described herein.

This disclosure also nucleic acid molecules that encode any of the CARs described herein (e.g., vectors that include a nucleic acid sequence encoding one of the CARs) and isolated T lymphocytes that express any of the CARs described herein.

The CAR described herein can include a spacer region located between the IL13 domain and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
| --- | --- | --- |
| a3 | 3 aa | AAA |
| linker | 10 aa | GGGSSGGGSG (SEQ ID NO: 14) |
| IgG4 hinge (S→P) (S228P) | 12 aa | ESKYGPPCPPCP (SEQ ID NO: 15) |
| IgG4 hinge | 12 aa | ESKYGPPCPSCP (SEQ ID NO: 52) |
| IgG4 hinge + linker | 22 aa | ESKYGPPCPPCPGGGSSGGGSG (SEQ ID NO: 16) |
| CD28 hinge | 39 aa | IEVMYPPPYLDNEKSNGTIIHVKGKHLCPSPLFPGPSKP (SEQ ID NO: 17) |
| CD8 hinge-48 aa | 48 aa | AKPTTTPAPRPPTPAPTIASQPLSLRPEACRPAAGGAVHTRGLDFACD (SEQ ID NO: 18) |
| CD8 hinge-45 aa | 45 aa | TTTPAPRPPTPAPTIASQPLSLRPEACRPAAGGAVHTRGLDFACD (SEQ ID NO: 19) |
| IgG4(HL-CH3) | 129 aa | ESKYGPPCPPCPGGGSSGGGSGGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 20) |
| IgG4(L235E, N297Q) | 229 aa | ESKYGPPCPSCPAPEFEGGPSVFLFPPKPKDTLMISRTPEVTCVVVDVSQEDPEVQFNWYVDGVEVHQAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 4) |
| IgG4(S228P, L235E, N297Q) | 229 aa | ESKYGPPCPPCPAPEFEGGPSVFLFPPKPKDTLMISRTPEVTCVVVDVSQEDPEVQFNWYVDGVEVHQAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 51) |
| IgG4(CH3) | 107 aa | GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 50) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In certain embodiments, the spacer is derived from an IgG1, IgG2, IgG3, or IgG4 that includes one or more amino acid residues substituted with an amino acid residue different from that present in an unmodified spacer. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof. In this numbering scheme, described in greater detail below, the first amino acid in the IgG4(L235E, N297Q) spacer in Table 1 is 219 and the first amino acid in the IgG4(HL-CH3) spacer in Table 1 is 219 as is the first amino acid in the IgG hinge sequence and the IgG4 hinge linker (HL) sequence in Table 1.

In some embodiments, the modified spacer is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof.

In certain embodiments, the modified spacer is derived from IgG4 region that includes one or more amino acid residues substituted with an amino acid residue different from that present in an unmodified region. The one or more substituted amino acid residues are selected from, but not limited to, one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified spacer is derived from an IgG4 region that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified spacer is substituted with the above identified amino acids at the indicated position.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 *Proc Natl Acad Sci USA* 63:78-85).

A variety of transmembrane domains can be used in CAR directed against IL13Rα2. Table 2 includes examples of suitable transmembrane domains. Where a spacer domain is present, the transmembrane domain is located carboxy terminal to the spacer domain.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 21) |
| CD28 | NM_006139 | 27 aa | FWVLVVVGGVLACYSLLVTVAFIIF WV (SEQ ID NO: 22) |
| CD28(M) | NM_006139 | 28 aa | MFWVLVVVGGVLACYSLLVTVAFII FWV (SEQ ID NO: 22) |
| CD4 | M35160 | 22 aa | MALIVLGGVAGLLLFIGLGIFF (SEQ ID NO: 5) |
| CD8tm | NM_001768 | 21 aa | IYIWAPLAGTCGVLLLSLVIT (SEQ ID NO: 23) |
| CD8tm2 | NM_001768 | 23 aa | IYIWAPLAGTCGVLLLSLVITLY (SEQ ID NO: 24) |
| CD8tm3 | NM_001768 | 24 aa | IYIWAPLAGTCGVLLLSLVITLYC (SEQ ID NO: 25) |
| 41BB | NM_001561 | 27 aa | IISFFLALTSTALLFLLFFLTLRF SVV (SEQ ID NO: 26) |

Many of the CAR described herein include one or more (e.g., two) costimulatory domains. The costimulatory domain(s) are located between the transmembrane domain and the CD3ζ signaling domain. Table 3 includes examples of suitable costimulatory domains together with the sequence of the CD3ζ signaling domain.

TABLE 3

Examples of Costimulatory Domains

| Name | Accession | Length | Sequence |
|---|---|---|---|
| CD3ζ | J04132.1 | 113 aa | RVKFSRSADAPAYQQGQNQLYNELNL GRREEYDVLDKRRGRDPEMGGKPRRK NPQEGLYNELQKDKMAEAYSEIGMKG ERRRGKGHDGLYQGLSTATKDTYDAL HMQALPPR |
| CD28 | NM_006139 | 42 aa | RSKRSRLLHSDYMNMTPRRPGPTRKH QYPYAPPRDFAAYRS (SEQ ID NO: 27) |
| CD28gg* | NM_006139 | 42 aa | RSKRSRGGHSDYMNMTPRRPGPTRKH YQPYAPPRDFAAYRS (SEQ ID NO: 28) |
| 41BB | NM_001561 | 42 aa | KRGRKKLLYIFKQPFMRPVQTTQEED GCSCRFPEEEEGGCEL (SEQ ID NO: 29) |
| OX40 | | 42 aa | ALYLLRRDQRLPPDAHKPPGGGSFRT PIQEEQADAHSTLAKI (SEQ ID NO: 30) |

DESCRIPTION OF DRAWINGS

FIG. 1 is a schematic depiction of IL13(E13Y)-zetakine CAR (Left) composed of the IL13Rα2-specific human IL-13 variant (huIL-13(E13Y)), human IgG4 Fc spacer (huγ4Fc), human CD4 transmembrane (huCD4 tm), and human CD3ζ chain cytoplasmic (huCD3ζ cyt) portions as indicated. Also depicted is a IL13(EQ)BBζ CAR which is the same as the IL13(E13Y)-zetakine with the exception of the two point mutations, L235E and N297Q indicated in red, that are located in the CH2 domain of the IgG4 spacer, and the addition of a costimulatory 4-1BB cytoplasmic domain (4-1BB cyt).

FIGS. 6A-C depicts the results of flow cytometric analysis of surface transgene and T cell marker expression. IL13(EQ)BBζ/CD19t+ $T_{CM}$ HD006.5 and HD187.1 were co-stained with anti-IL13-PE and anti-CD8-FITC to detect CD8+ CAR+ and CD4+ (i.e., CD8 negative) CAR+ cells (A), or anti-CD19-PE and anti-CD4-FITC to detect CD4+ CD19t+ and CD8+ (i.e., CD4 negative) CAR+ cells (B). IL13(EQ)BBζ/CD19t+ $T_{CM}$ HD006.5 and HD187.1 stained with fluorochromeconjugatedanti-CD3, TCR, CD4, CD8, CD62L and CD28 (grey histograms) or isotype controls (black histograms) (C). In all cases the percentages based on viable lymphocytes (DAPI negative) stained above isotype.

FIGS. 10A-C depict the results of studies comparing ant-tumor efficacy of IL13(EQ)BBζ $T_{CM}$ and IL13-zetakine CTL clones. EGFP-ffLuc+ PBT030-2 TSs (1×10$^5$) were stereotactically implanted into the right forebrain of NSG mice. On day 8, mice received either 1.3×10$^6$ mock $T_{CM}$ (no CAR; n=6), 1.0, 0.3 or 0.1×10$^6$ CAR+ IL13(EQ)BBζ $T_{CM}$ (78% CAR+; n=6-7), 1.0, 0.3 or 0.1×10$^6$ IL13-zetakine CD8+ CTL cl. 2D7 (clonal CAR+; n=6-7), or no treatment (n=5). Xenogen imaging of representative mice from each group showing relative tumor burden (A). Linear regression lines of natural log of ffLuc flux (photons/sec) shows that IL13(EQ)BBζ $T_{CM}$ achieve superior tumor regression as compared to first-generation IL13-zetakine CTL cl. 2D7, mock $T_{CM}$ and tumor only (B). Average flux per group at day 27 post tumor injection demonstrating that the 0.1×10$^6$ IL13(EQ)BBζ $T_{CM}$ dose outperforms the ten-fold higher 1.0×10$^6$ dose of IL13-zetakine CD8+ CTL cl. 2D7 (p=0.043; Welch two sample t-test) (C).

FIGS. 14A-C depict the results of a series of studies evaluating costimulatory domains of IL13Rα2-specific CAR. Schematic of IL13Rα2-specific CAR constructs comparing various intracellular endo/signaling domains, including the first generation CD3z CAR lacking costimulation, versus second generation CARs incorporating either 4-1BB or CD28, versus a third generation CAR containing both CD28 and 41BB. All CAR cassettes also contain the T2A ribosomal skip and truncated CD19 (CD19t) sequences as a marker for transduced cells (A). CD4 and CD8 TCM were lentivirally transduced and CAR-expressing T cells were immunomagnetically enriched via anti-CD19. CD19 and IL13 (i.e., CAR) expression levels as measured by flow cytometry (B). Stability of each CAR construct was determined by dividing the CAR (IL13) mean flourescence intensty (MFI) by that of the transduction marker (CD19t) (C). The 4-1BB containing CARs demonstrated the lowest expression levels as compared to the CD19t transduction marker.

FIGS. 16A-C depict the results of a series of studies of the in vivo efficacy of IL13Rα2-specific CARs. NSG mice received an intracranial injection of ffLuc+ PBT030-2 tumor cells on day 0, and were randomized into 6 groups (n=9-10 mice per group) for i.c. treatment with either PBS (Tumor Only), mock-transduced T cells or T cells expressing the indicated IL13Rα2-specific CAR on day 8. Quantitative bioluminescence imaging was then carried out to monitor tumor growth over time. Bioluminescence images for representative mice in each group (A). Mean+S.E. of total flux levels of luciferase activity over time in each group (B). Flux levels for each mouse at Day 27. All groups treated with IL13Rα2-specific CAR T cells, except those treated with T cells expressing the CD28-CAR, show statistically-significant reduction in tumor volume compared to mice treated with mock-transduced T cells (C)

FIGS. 17A-B depict the amino acid sequence of IL13 (EQ)BBζ/CD19t+ (SEQ ID NO:10).

FIGS. 18A-O depict a sequence comparison of IL13(EQ) 41BBζ[IL13 {EQ}41BBζ T2A-CD19t_epHIV7; pF02630] (SEQ ID NO:12) and CD19Rop_epHIV7 (pJ01683) (SEQ ID NO:13).

FIG. 19 depicts the amino acid sequence of IL13(EmY)-CD8h3-CD8tm2-41BB Zeta (SEQ ID NO:31 with GMSCFRa signal peptide; SEQ ID NO:39 without GMSCFRa signal peptide).

FIG. 20 depicts the amino acid sequence of IL13(EmY)-CD8h3-CD28tm-CD28gg-41BB-Zeta (SEQ ID NO:32 with GMSCFRa signal peptide; SEQ ID NO:40 without GMSCFRa signal peptide).

FIG. 21 depicts the amino acid sequence of IL13(EmY)-IgG4(HL-CH3)-CD4tm-41BB-Zeta (SEQ ID NO:33 with GMSCFRa signal peptide; SEQ ID NO:41 without GMSCFRa signal peptide).

FIG. 22 depicts the amino acid sequence of IL13(EmY)-IgG4(L235E,N297Q)-CD8tm-41BB-Zeta (SEQ ID NO:34 with GMSCFRa signal peptide; SEQ ID NO:42 without GMSCFRa signal peptide).

FIG. 23 depicts the amino acid sequence of IL13(EmY)-Linker-CD28tm-CD28gg-41BB-Zeta (SEQ ID NO:35 with GMSCFRa signal peptide; SEQ ID NO:43 without GMSCFRa signal peptide).

FIG. 24 depicts the amino acid sequence of IL13(EmY)-HL-CD28m-CD28gg-41BB-Zeta (SEQ ID NO:36 with GMSCFRa signal peptide; SEQ ID NO:44 without GMSCFRa signal peptide).

FIG. 25 depicts the amino acid sequence of IL13(EmY)-IgG4(HL-CH3)-CD28tm-CD28gg-41BB-Zeta (SEQ ID NO:37 with GMSCFRa signal peptide; SEQ ID NO:45 without GMSCFRa signal peptide).

FIG. 26 depicts the amino acid sequence of IL13(EmY) IgG4(L235E,N297Q)-CD28tm-CD28gg-41BB-Zeta (SEQ ID NO:38 with GMSCFRa signal peptide; SEQ ID NO:46 without GMSCFRa signal peptide).

FIG. 27 depicts the amino acid sequence of IL13(EmY)-CD8h3-CD8tm-41BB Zeta (SEQ ID NO:47 with GMSCFRa signal peptide; SEQ ID NO:48 without GMSCFRa signal peptide).

DETAILED DESCRIPTION

Figure 2A:
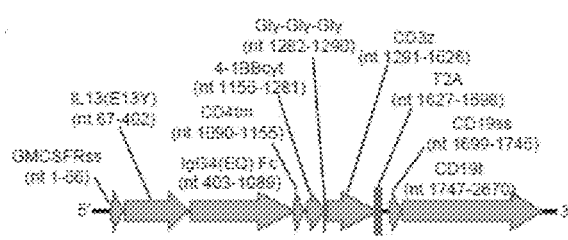
FIGS. 2A-C depict certain vectors an open reading frames. A is a diagram of the cDNA open reading frame of the 2670 nucleotide IL13(EQ)BBZ-T2ACD19t construct, where the IL13Rα2-specific ligand IL13(E13Y), IgG4(EQ) Fc hinge, CD4 transmembrane, 4-1BB cytoplasmic signaling, three-glycine linker, and CD3ζ cytoplasmic signaling domains of the IL13(EQ)BBZ CAR, as well as the T2A ribosome skip and truncated CD19 sequences are indicated. The human GM-CSF receptor alpha and CD19 signal sequences that drive surface expression of the IL13(EQ)BBζ CAR and CD19t are also indicated. B is a diagram of the sequences flanked by long terminal repeats (indicated by 'R') that will integrate into the host genome. C is a map of the IL13(EQ)BBZ-T2A-CD19t_epHIV7 plasmid.

Described below is the structure, construction and characterization of various IL13Rα2-specific chimeric antigen receptors. A chimeric antigen (CAR) is a recombinant biomolecule that contains, at a minimum, an extracellular recognition domain, a transmembrane region, and an intracellular signaling domain. The term "antigen," therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more costimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

One IL13Rα2-specific CAR described herein is referred to as IL13(EQ)BBζ. This CAR includes a variety of important features including: a IL13α2 ligand having an amino acid change that improves specificity of biding to IL13α2; the domain of CD137 (4-1BB) in series with CD3ζ to provide beneficial costimulation; and an IgG4 Fc region that is mutated at two sites within the CH2 region (L235E; N297Q) in a manner that reduces binding by Fc receptors (FcRs). Other CAR described herein contain a second costimulatory domain.

In some cases the CAR described herein, including the IL13(EQ)BBζ CAR can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD19t provides a marker for immunological targeting of the transduced cells in vivo using clinically available antibodies and/or immunotoxin reagents to selectively delete the therapeutic cells, and thereby functioning as a suicide switch.

Gliomas, express IL13 receptors, and in particular, high-affinity IL13 receptors. However, unlike the IL13 receptor, glioma cells overexpress a unique IL13Rα2 chain capable of binding IL13 independently of the requirement for IL4Rβ or γc44. Like its homolog IL4, IL13 has pleotropic immunoregulatory activity outside the CNS. Both IL13 and IL4 stimulate IgE production by B lymphocytes and suppress pro-inflammatory cytokine production by macrophages.

Detailed studies using autoradiography with radiolabeled IL13 have demonstrated abundant IL13 binding on nearly all malignant glioma tissues studied. This binding is highly homogeneous within tumor sections and in single cell analysis. However, molecular probe analysis specific for IL13Rα2 mRNA did not detect expression of the glioma-specific receptor by normal brain elements and autoradiography with radiolabeled IL13 also could not detect specific IL13 binding in the normal CNS. These studies suggest that the shared IL13Rα1/IL4β/γc receptor is not expressed detectably in the normal CNS. Therefore, IL13Rα2 is a very specific cell-surface target for glioma and is a suitable target for a CAR designed for treatment of a glioma.

Binding of IL13-based therapeutic molecules to the broadly expressed IL13Rα1/IL4β/γc receptor complex, however, has the potential of mediating undesired toxicities to normal tissues outside the CNS, and thus limits the systemic administration of these agents. An amino acid substitution in the IL13 alpha helix A at amino acid 13 of tyrosine for the native glutamic acid selectively reduces the affinity of IL13 to the IL13Rα1/IL4β/γc receptor. Binding of this mutant (termed IL13(E13Y)) to IL13Rα2, however, was increased relative to wild-type IL13. Thus, this minimally altered IL13 analog simultaneously increases IL13's specificity and affinity for glioma cells. Therefore, CAR described herein include an IL13 containing a mutation (E to Y or E to some other amino acid such as K or R or L or V) at amino acid 13 (according to the numbering of Debinski et al. 1999 Clin Cancer Res 5:3143s). IL13 having the natural sequence also may be used, however, and can be useful, particularly in situations where the modified T cells are to be locally administered, such as by injection directly into a tumor mass.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets, can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a SIN lentiviral vector that directs the expression of an IL13Rα2-specific CAR (e.g., IL13(EQ)BBζ) as well as a truncated human CD19 (CD19t), a non-immunogenic surface marker for both in vivo detection and potential ex vivo selection. The activated/genetically modified central memory T cells can be expanded in vitro with IL-2/IL-15 and then cryopreserved.

Example 1: Construction and Structure of an IL13Rα2-Specific CAR

The structure of a useful IL13Rα2-specific CAR is described below. The codon optimized CAR sequence contains a membrane-tethered IL-13 ligand mutated at a single site (E13Y) to reduce potential binding to IL13Rα1, an IgG4 Fc spacer containing two mutations (L235E; N297Q) that greatly reduce Fc receptor-mediated recognition models, a CD4 transmembrane domain, a costimulatory 4-1BB cytoplasmic signaling domain, and a CD3ζ cytoplasmic signaling domain. A T2A ribosome skip sequence separates this IL13(EQ)BBζ CAR sequence from CD19t, an inert, non-immunogenic cell surface detection/selection marker. This T2A linkage results in the coordinate expression of both IL13(EQ)BBζ and CD19t from a single transcript. FIG. 1A is a schematic drawing of the 2670 nucleotide open reading frame encoding the IL13(EQ)BBZ-T2ACD19t construct. In this drawing, the IL13Rα2-specific ligand IL13(E13Y), IgG4(EQ) Fc, CD4 transmembrane, 4-1BB cytoplasmic signaling, three-glycine linker, and CD3ζ cytoplasmic signaling domains of the IL13(EQ)BBZ CAR, as well as the T2A ribosome skip and truncated CD19 sequences are all indicated. The human GM-CSF receptor alpha and CD19 signal sequences that drive surface expression of the IL13 (EQ)BBZ CAR and CD19t are also indicated. Thus, the IL13(EQ)BBZ-T2ACD19t construct includes a IL13Rα2-specific, hinge-optimized, costimulatory chimeric immunoreceptor sequence (designated IL13(EQ)BBZ), a ribosome-skip T2A sequence, and a CD19t sequence.

The IL13(EQ)BBZ sequence was generated by fusion of the human GM-CSF receptor alpha leader peptide with IL13(E13Y) ligand 5 L235E/N297Q-modified IgG4 Fc hinge (where the double mutation interferes with FcR recognition), CD4 transmembrane, 4-1BB cytoplasmic signaling domain, and CD3ζ cytoplasmic signaling domain sequences. This sequence was synthesized de novo after codon optimization. The T2A sequence was obtained from digestion of a T2A-containing plasmid. The CD19t sequence was obtained from that spanning the leader peptide sequence to the transmembrane components (i.e., basepairs 1-972) of a CD19-containing plasmid. All three fragments, 1) IL13 (EQ)BBZ, 2) T2A, and 3) CD19t, were cloned into the multiple cloning site of the epHIV7 lentiviral vector. When transfected into appropriate cells, the vector integrates the sequence depicted schematically in FIG. 1B into the host cells genome. FIG. 1C provides a schematic drawing of the 9515 basepair IL13(EQ)BBZ-T2A-CD19t_epHIV7 plasmid itself.

Figure 2B:
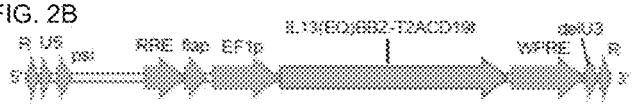
Figure 2C:
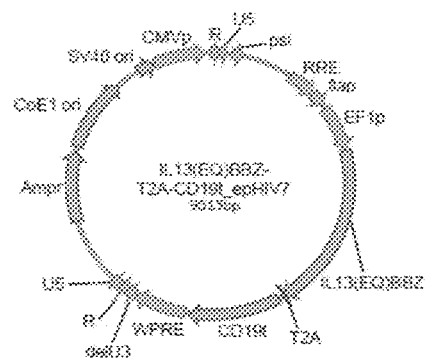

As shown schematically in FIG. 2, IL13(EQ)BBZ CAR differs in several important respects from a previously described IL13Rα2-specific CAR referred to as IL13 (E13Y)-zetakine (Brown et al. 2012 *Clinical Cancer Research* 18:2199). The IL13(E13Y)-zetakine is composed of the IL13Rα2-specific human IL-13 mutein (huIL-13 (E13Y)), human IgG4 Fc spacer (huγ4Fc), human CD4 transmembrane (huCD4 tm), and human CD3ζ chain cytoplasmic (huCD3ζ cyt) portions as indicated. In contrast, the IL13(EQ)BBζ) has two point mutations, L235E and N297Q that are located in the CH2 domain of the IgG4 spacer, and a costimulatory 4-1BB cytoplasmic domain (4-1BB cyt).

Example 2: Construction and Structure of epHIV7 Used for Expression of an IL13Rα2-Specific CAR The pHIV7 plasmid is the parent plasmid from which the clinical vector IL13(EQ)BBZ-T2A-CD19t_epHIV7 was derived in the T cell Therapeutics Research Laboratory (TCTRL) at City of Hope (COH). The epHIV7 vector used for expression of the CAR was produced from pHIV7 vector. Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository. The woodchuck post-transcriptional regulatory element (WPRE) sequence was previously described.

Figure 3:
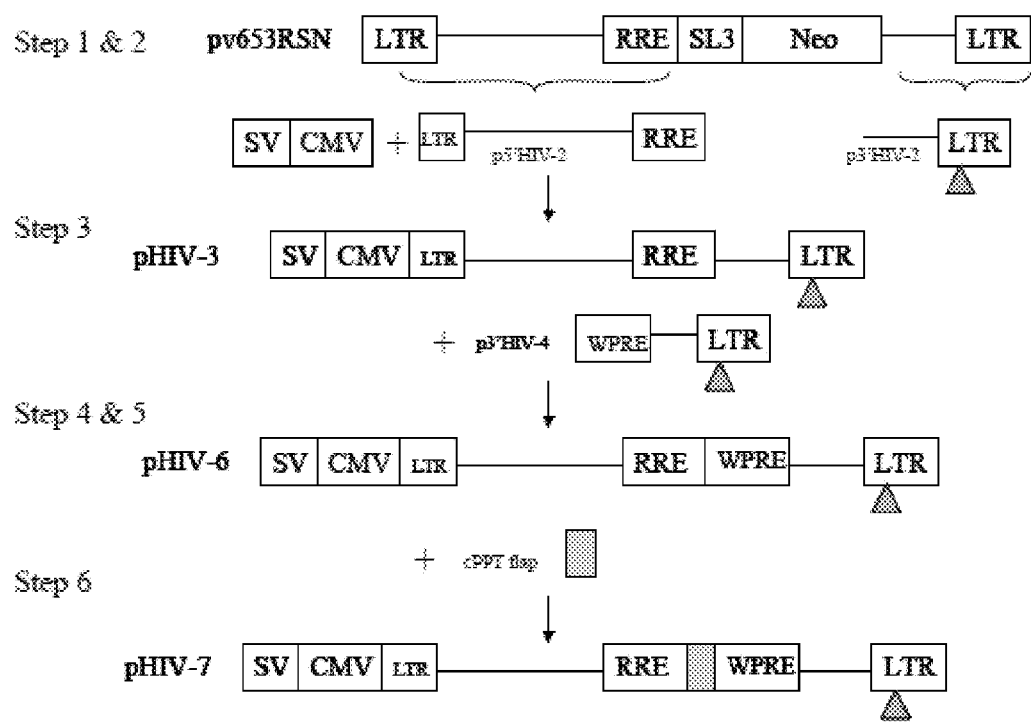
FIG. 3 depicts the construction of pHIV7.

Construction of pHIV7 is schematically depicted in FIG. 3. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi ψ, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector), are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

Figure 4:
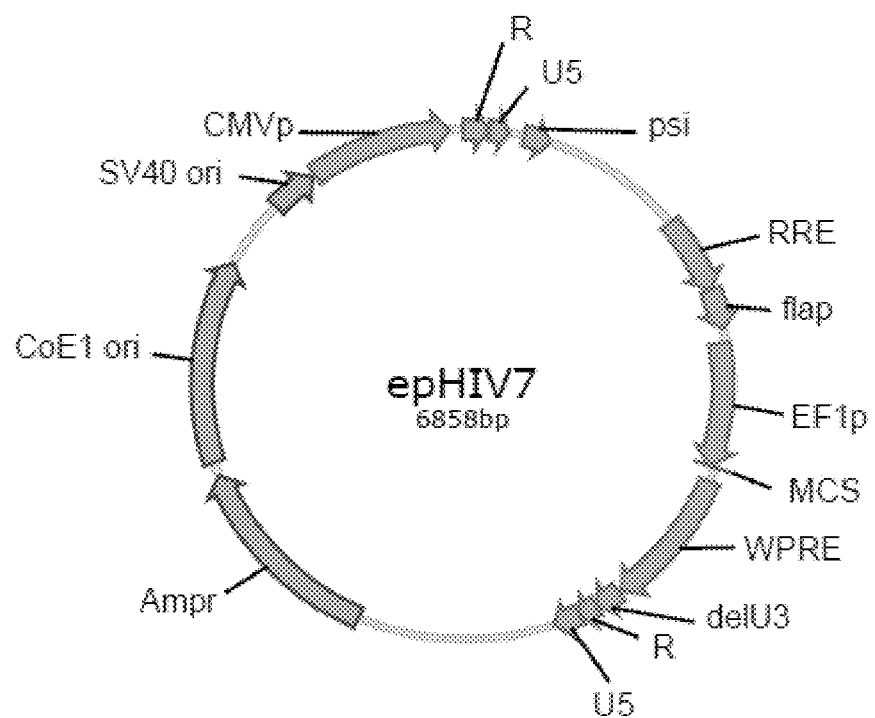
FIG. 4 depicts the elements of pHIV7.
Figure 5:
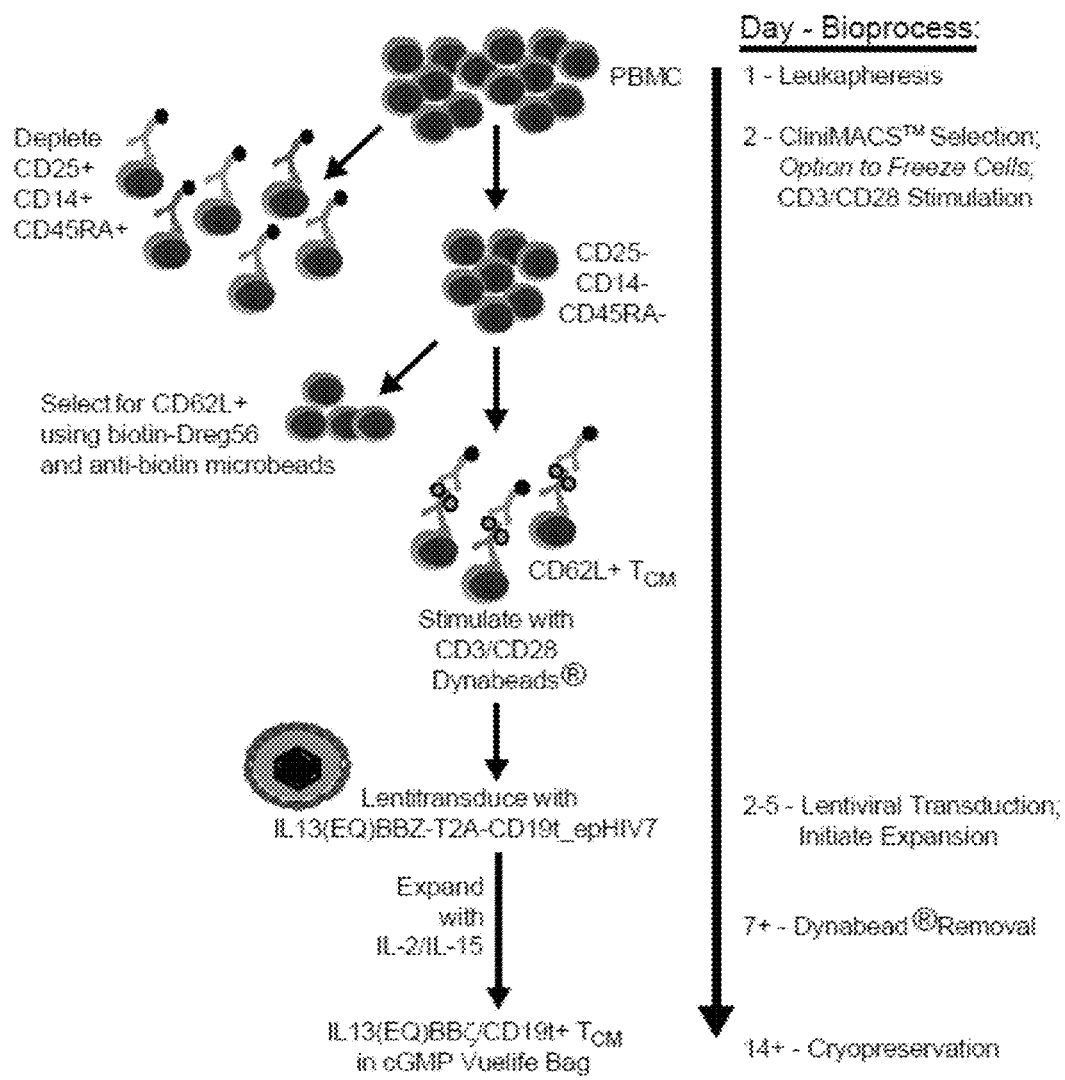
FIG. 5 depicts a production scheme for IL13(EQ)BBζ/CD19t+ $T_{CM}$.

The CMV promoter was replaced by the EF1α-HTLV promoter (EF1p), and the new plasmid was named epHIV7 (FIG. 4). The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the IL13(EQ)BBZ-T2ACD19t_epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes (56). Table 4 summarizes the various regulator elements present in IL13(EQ)BBZ-T2ACD19t_epHIV7.

TABLE 4

Functional elements of IL13(EQ)41BBZ-T2A-CD19t_epHIV7

| Regulatory Elements and Genes | Location (Nucleotide Numbers) | Comments |
| --- | --- | --- |
| U5 | 87-171 | 5' Unique sequence |
| psi | 233-345 | Packaging signal |
| RRE | 957-1289 | Rev-responsive element |
| flap | 1290-1466 | Contains polypurine track sequence and central termination sequence to facilitate nuclear import of pre-integration complex |
| EF1p Promoter | 1524-2067 | EF1-alpha Eukaryotic Promoter |

TABLE 4-continued

Functional elements of IL13(EQ)41BBZ-T2A-CD19t_epHIV7

| Regulatory Elements and Genes | Location (Nucleotide Numbers) | Comments |
| --- | --- | --- |
| | | sequence driving expression of CD19Rop |
| IL13-IgG4 (EQ)-41BB-Zeta-T2A-CD19t | 2084-4753 | Therapeutic insert |
| WPRE | 4790-5390 | Woodchuck hepatitis virus derived regulatory element to enhance viral RNA transportation |
| delU3 | 5405-5509 | 3' U3 with deletion to generate SIN vector |
| R | 5510-5590 | Repeat sequence within LTR |
| U5 | 5591-5704 | 3' U5 sequence in LTR |
| $Amp^R$ | 6540-7398 | Ampicillin-resistance gene |
| CoE1 ori | 7461-8342 | Replication origin of plasmid |
| SV40 ori | 8639-8838 | Replication origin of SV40 |
| CMV promoter | 8852-9451 | CMV promoter to generate viral genome RNA |
| R | 9507-86 | Repeat sequence within LTR |

Example 3: Production of Vectors for Transduction of Patient T Cells

For each plasmid (IL13(EQ)BBZ-T2A-CD19t_epHIV7; pCgp; pCMV-G; and pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells were expanded from the 293T working cell (WCB), which has been tested to confirm sterility and the absence of viral contamination. A vial of 293T cells from the 293T WCB was thawed. Cells were grown and expanded until sufficient numbers of cells existed to plate an appropriate number of 10 layer cell factories (CFs) for vector production and cell train maintenance. A single train of cells can be used for production.

The lentiviral vector was produced in sub-batches of up to 10 CFs. Two sub-batches can be produced in the same week leading to the production of approximately 20 L of lentiviral supernatant/week. The material produced from all sub-batches were pooled during the downstream processing phase, in order to produce one lot of product. 293T cells were plated in CFs in 293T medium (DMEM with 10% FBS). Factories were placed in a 37° C. incubator and horizontally leveled in order to get an even distribution of the cells on all the layers of the CF. Two days later, cells were transfected with the four lentiviral plasmids described above using the CaPO4 method, which involves a mixture of Tris:EDTA, 2M CaCl2, 2×HBS, and the four DNA plasmids. Day 3 after transfection, the supernatant containing secreted lentiviral vectors was collected, purified and concentrated. After the supernatant was removed from the CFs, End-of-Production Cells were collected from each CF. Cells were trypsinized from each factory and collected by centrifugation. Cells were resuspended in freezing medium and cryopreserved. These cells were later used for replication-competent lentivirus (RCL) testing.

To purify and formulate vectors crude supernatant was clarified by membrane filtration to remove the cell debris. The host cell DNA and residual plasmid DNA were degraded by endonuclease digestion (Benzonase®). The viral supernatant was clarified of cellular debris using a 0.45 µm filter. The clarified supernatant was collected into a pre-weighed container into which the Benzonase® is added (final concentration 50 U/mL). The endonuclease digestion for residual plasmid DNA and host genomic DNA as performed at 37° C. for 6 h. The initial tangential flow ultrafiltration (TFF) concentration of the endonuclease-treated supernatant was used to remove residual low molecular weight components from the crude supernatant, while concentrating the virus ~20 fold. The clarified endonuclease-treated viral supernatant was circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant was initiated during the concentration process to sustain the cartridge performance. An 80% permeate replacement rate was established, using 4% lactose in PBS as the diafiltration buffer. The viral supernatant was brought to the target volume, representing a 20-fold concentration of the crude supernatant, and the diafiltration was continued for 4 additional exchange volumes, with the permeate replacement rate at 100%.

Further concentration of the viral product was accomplished by using a high speed centrifugation technique. Each sub-batch of the lentivirus was pelleted using a Sorvall RC-26 plus centrifuge at 6000 RPM (6,088 RCF) at 6° C. for 16-20 h. The viral pellet from each sub-batch was then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material was then placed at −80° C., while samples from each sub-batch were tested for sterility. Following confirmation of sample sterility, the sub-batches were rapidly thawed at 37° C. with frequent agitation. The material was then pooled and manually aliquoted in the Class II Type A/B3 biosafety cabinet in the viral vector suite. A fill configuration of 1 mL of the concentrated lentivirus in sterile USP class 6, externally threaded O-ring cryovials was used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it was tested for residual host DNA contaminants, and the transfer of residual host and plasmid DNA. Among other tests, vector identity was evaluated by RT-PCR to ensure that the correct vector is present. All release criteria were met for the vector intended for use in this study.

Example 4: Preparation of T Cells Suitable for Use in ACT

T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anti-cancer therapy.

An outline of the manufacturing strategy for $T_{CM}$ is depicted in FIG. 8 (Manufacturing schema for IL13(EQ) BBζ/CD19t+ $T_{CM}$). Specifically, apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the CliniMACS™ separation device. Following depletion, negative fraction cells are enriched for CD62L+ $T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with IL13(EQ)BBZ-T2A-CD19t_epHIV7lentiviral vector at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CS5, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

Two qualification runs on cells procured from healthy donors were performed using the manufacturing platform described above. Each preclinical qualification run product was assigned a human donor (HD) number—HD006.5 and HD187.1. Importantly, as shown in Table 5, these qualification runs expanded >80 fold within 28 days and the expanded cells expressed the IL13(EQ)BBγ/CD19t transgenes.

TABLE 5

Summary of Expression Data from Pre-clinical Qualification Run Product

| Cell Product | CAR | CD19 | CD4+ | CD8+ | Fold Expansion |
|---|---|---|---|---|---|
| HD006.5 | 20% | 22% | 24% | 76% | 84-fold (28 days) |
| Hd187.1 | 18% | 25% | 37% | 63% | 259-fold (28 days) |

Example 5: Flow Cytometric Analysis of Surface Transgene and T Cell Marker Expression in IL13(EQ)BBγ/CD19t+ $T_{CM}$ The two preclinical qualification run products described in Example 4 were used in pre-clinical studies to as described below. FIGS. 6A-C depict the results of flow cytometric analysis of surface transgene and T cell marker expression. IL13(EQ)BBγ/CD19t+ $T_{CM}$ HD006.5 and HD187.1 were co-stained with anti-IL13-PE and anti-CD8-FITC to detect CD8+ CAR+ and CD4+ (i.e., CD8 negative) CAR+ cells (FIG. 6A), or anti-CD19-PE and anti-CD4-FITC to detect CD4+CD19t+ and CD8+ (i.e., CD4 negative) CAR+ cells (FIG. 6B). IL13(EQ)BBγ/CD19t+ $T_{CM}$ HD006.5 and HD187.1 were stained with fluorochrome-conjugated anti-CD3, TCR, CD4, CD8, CD62L and CD28 (grey histograms) or isotype controls (black histograms) (FIG. 6C). In each of FIGS. 6A-C, the percentages indicated are based on viable lymphocytes (DAPI negative) stained above isotype.

Example 6: Effector Activity of IL13(EQ)BBγ/CD19t+ $T_{CM}$

Figure 7A:
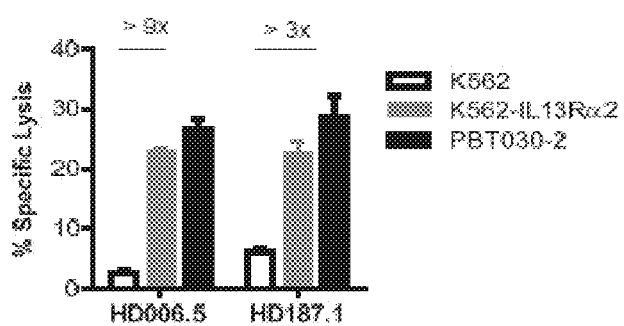
FIGS. 7A-B depict the in vitro functional characterization of IL13Rα2-specific effector function of IL13(EQ)BBZ+ $T_{CM}$. IL13(EQ)BBZ/CD19t+ $T_{CM}$ HD006.5 and HD187.1 were used as effectors in a 6-hour $^{51}$Cr release assay using a 10:1 E:T ratio based on CD19t expression. The IL13Rα2-positive tumor targets were K562 engineered to express IL13Rα2 (K562-IL13Rα2) and primary glioma line PBT030-2, and the IL13Rα2-negative tumor target control was K562 parental line (A). IL13(EQ)BBZ/CD19t+ $T_{CM}$ HD006.5 and HD187.1 were evaluated for antigen-dependent cytokine production following overnight co-culture at a 10:1 E:T ratio with IL13Rα2-positive and negative targets. Cytokine levels were measured using the Bio-Plex Pro Human Cytokine TH1/TH2 Assay kit and INF-γ are reported (B).
Figure 7B:
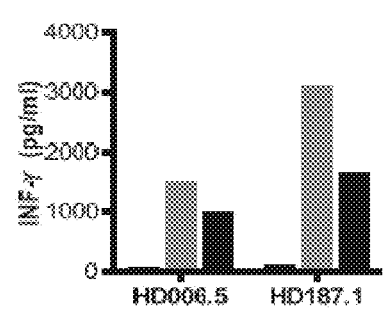

The effector activity of IL13(EQ)BBζCD19t+ $T_{CM}$ was assessed and the results of this analysis are depicted in FIGS. 7A-B. Briefly, IL13(EQ)BBγ/CD19t+ $T_{CM}$ HD006.5 and HD187.1 were used as effectors in a 6-hour 51Cr-release assay using a 10E:1T ratio based on CD19t expression. The IL13Rα2-positive tumor targets were K562 engineered to express IL13Rα2 (K562-IL13Rα2) and primary glioma line PBT030-2, and the IL13Rα2-negative tumor target control was the K562 parental line (FIG. 7A). IL13(EQ)BBγ/CD19t+HD006.5 and HD187.1 were evaluated for antigen-dependent cytokine production following overnight co-culture at a 10E:1T ratio with the same IL13Rα2-positive and negative targets as described in above. Cytokine levels were measured using the Bio-Plex Pro Human Cytokine TH1/TH2 Assay kit and INF-γ levels are depicted (FIG. 7B).

Example 7: In Vivo Anti-Tumor Activity of IL13(EQ)BBγ/CD19t+ $T_{CM}$

Figure 8A:
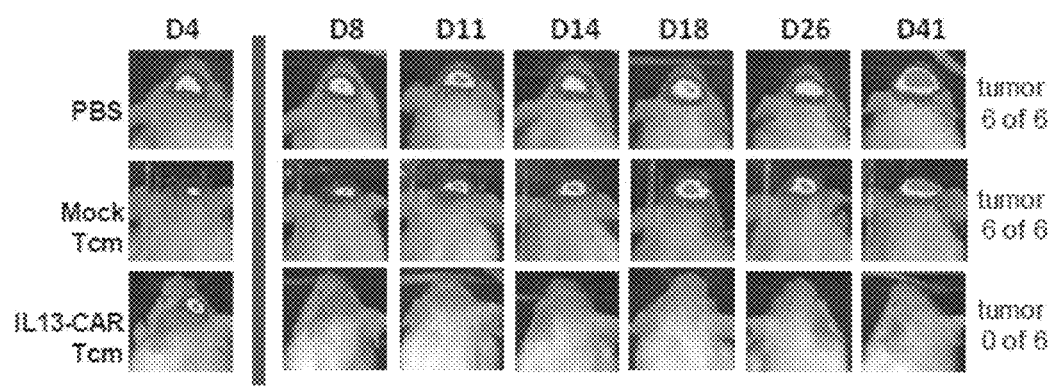
FIGS. 8A-C depict the result of studies demonstrating the regression of established glioma tumor xenografts after adoptive transfer of IL13(EQ)BBζ/CD19t+ $T_{CM}$. EGFP-ffLuc+ PBT030-2 tumor cells (1×10$^5$) were stereotactically implanted into the right forebrain of NSG mice. On day 5, mice received either 2×10$^6$ IL13(EQ)BBζ/CD19t+ $T_{CM}$ (1.1×10$^6$ CAR+; n=6), 2×10$^6$ mock $T_{CM}$ (no CAR; n=6) or PBS (n=6). Representative mice from each group showing relative tumor burden using Xenogen Living Image (A). Quantification of ffLuc flux (photons/sec) shows that IL13 (EQ)BBζ/CD19t+ $T_{CM}$ induce tumor regression as compared to mock-transduced $T_{CM}$ and PBS (#p<0.02, *p<0.001, repeated measures ANOVA) (B). Kaplan Meier survival curve (n=6 per group) demonstrating significantly improved survival (p=0.0008; log-rank test) for mice treated with IL13(EQ)BBζ/CD19t+ $T_{CM}$ (C).
Figure 8B:
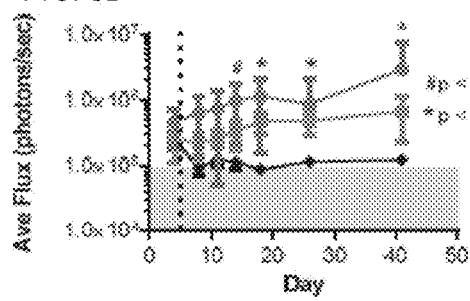
Figure 8C:
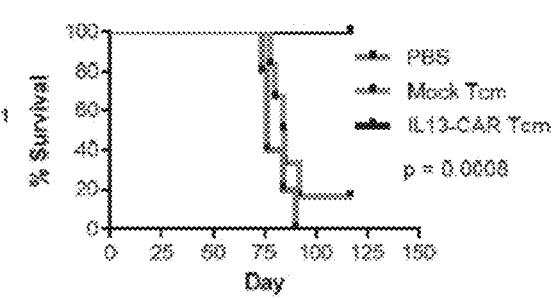

The studies described below demonstrate that IL13(EQ) BBγ/CD19t+ $T_{CM}$ exhibit anti-tumor efficacy in in vivo mouse models. Specifically, we have evaluated the anti-tumor potency of IL13(EQ)BBγ/CD19t+ $T_{CM}$ against the IL13Rα2+ primary low-passage glioblastoma tumor sphere line PBT030-2, which has been engineered to express both EGFP and firefly luciferase (ffLuc) reporter genes (PBT030-2 EGFP:ffLuc) (6). A panel of primary lines (PBT) from patient glioblastoma specimens grown as tumor spheres (TSs) in serum-free media. These expanded TS lines exhibit stem cell-like characteristics, including expression of stem cell markers, multilineage differentiation and capacity to initiate orthotopic tumors in immunocompromised mice (NSG) at low cell numbers. The PBT030-2 EGFP:ffLuc TS-initiated xenograft model ($0.1 \times 10^6$ cells; 5 day engraftment) has been previously used to evaluate in vivo anti-tumor activity in NSG mice of IL13Rα2-specific CAR expressing T cells, whereby three injections of $2 \times 10^6$ cytolytic T lymphocytes (CTLs) over a course of 2 weeks were shown to reduce tumor growth. However, in those experiments the majority of the PBT030-2 tumors eventually recurred. By comparison, a single injection of IL13(EQ) BBγ/CD19t+ $T_{CM}$ ($1.1 \times 10^6$ CAR+ $T_{CM}$; $2 \times 10^6$ total $T_{CM}$) exhibited robust anti-tumor activity against PBT030-2 EGFP:ffLuc TS-initiated tumors ($0.1 \times 10^6$ cells; 5 day engraftment) as shown in FIGS. 8A-C. As compared to NSG mice treated with either PBS or mock transduced $T_{CM}$ (no CAR), IL13(EQ)BBγ/CD19t+ $T_{CM}$ significantly reduce ffLuc flux ($p<0.001$ at >18-days) and significantly improve survival ($p=0.0008$).

Briefly, EGFP-ffLuc+ PBT030-2 tumor cells ($1 \times 10^5$) were stereotactically implanted into the right forebrain of NSG mice. On day 5, mice received either $2 \times 10^6$ IL13(EQ) BBγ/CD19t+ $T_{CM}$ ($1.1 \times 106$ CAR+; n=6), $2 \times 10^6$ mock $T_{CM}$ (no CAR; n=6) or PBS (n=6). FIG. 8A depicts representative mice from each group showing relative tumor burden using Xenogen Living Image. Quantification of ffLuc flux (photons/sec) shows that IL13(EQ)BBζ/CD19t+ $T_{CM}$ induce tumor regression as compared to mock-transduced $T_{CM}$ and PBS (#p<0.02, *p<0.001, repeated measures ANOVA) (FIG. 8B). As shown in FIG. 8C, a Kaplan Meier survival curve (n=6 per group) demonstrates significantly improved survival (p=0.0008; log-rank test) for mice treated with IL13(EQ)BBγ/CD19t+ $T_{CM}$.

Example 8: Comparison of IL13(EQ)BBζ+ Tcm and Non-Tcm IL13-Zetakine CD8+ CTL Clones in Antitumor Efficacy and T Cell Persistence The studies described below compare IL13(EQ)BBζ+ Tcm and a previously created IL13Rα2-specific human CD8+ CTLs (IL13-zetakine CD8+ CTL (described in Brown et al. 2012 Clin Cancer Res 18:2199 and Kahlon et al. 2004 Cancer Res 64:9160). The IL13-zetakine uses a CD3ζ stimulatory domain, lacks a co-stimulatory domain and uses the same IL13 variant as IL13(EQ)BBζ+.

A panel of primary lines (PBT) from patient glioblastoma specimens grown as tumor spheres (TSs) in serum-free media was generated (Brown et al. 2012 Clin Cancer Res 18:2199; Brown et al. 2009 Cancer Res 69:8886). These expanded TS lines exhibit stem cell-like characteristics, including expression of stem cell markers, multi-lineage differentiation and capacity to initiate orthotopic tumors in immunocompromised mice (NSG) at low cell numbers. The IL13Rα2+ primary low-passage glioblastoma TS line PBT030-2, which has been engineered to express both EGFP and firefly luciferase (ffLuc) reporter genes (PBT030-2 EGFP:ffLuc) (Brown et al. 2012 Clin Cancer Res 18:2199) was used for the experiments outlined below.

Figure 9A:
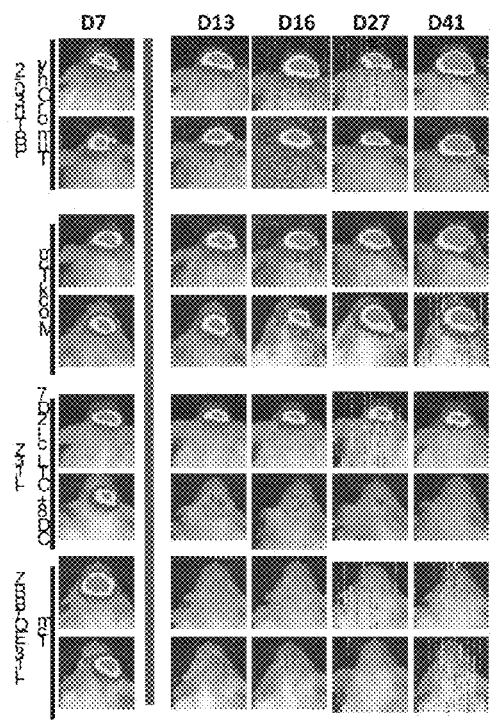
FIGS. 9A-C depict the results of studies comparing ant-tumor efficacy of IL13(EQ)BBZ $T_{CM}$ and IL13-zetakine CTL clones. EGFP-ffLuc+ PBT030-2 TSs (1×10$^5$) were stereotactically implanted into the right forebrain of NSG mice. On day 8, mice received either 1.6×10$^6$ mock $T_{CM}$ (no CAR), 1.0×10$^6$ CAR+ IL13(EQ)BBζ $T_{CM}$ (1.6×10$^6$ total T cells; 63% CAR), 1.0×10$^6$ IL13-zetakine CD8+ CTL cl. 2D7 (clonal CAR+), or no treatment (n=6 per group). Representative mice from each group showing relative tumor burden using Xenogen Living Image (A). Linear regression lines of natural log of ffLuc flux (photons/sec) over time, P-values are for group by time interaction comparisons (B). Kaplan Meier survival analysis (n=6 per group) demonstrate significantly improved survival (p=0.02; log-rank test) for mice treated with IL13(EQ)BBζ $T_{CM}$ as compared to IL13-zetakine CD8+ CTL cl. 2D7 (C).
Figure 9B:
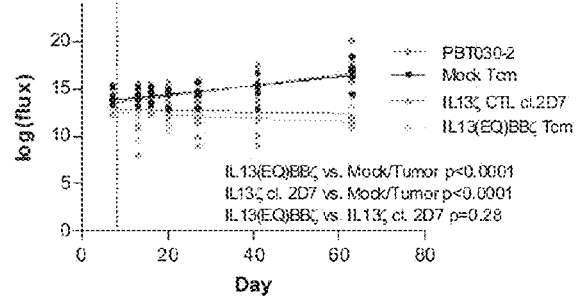
Figure 9C:
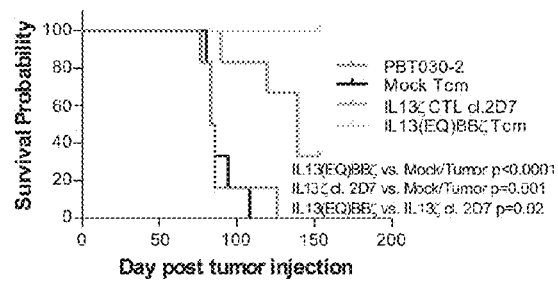

First, a single dose ($1\times10^6$ CAR T cells) of IL13(EQ)BBζ+ Tcm product was compared to IL13-zetakine CD8+ CTL clones evaluated against day 8 PBT030-2 EGFP:ffuc TS-initiated xenografts ($0.1\times10^6$ cells). While both IL13Rα2-specific CAR T cells (IL13-zetakine CTL and IL13(EQ)BBζ Tcm) demonstrated antitumor activity against established PBT030-2 tumors as compared to untreated and mock Tcm (CAR-negative) controls (FIGS. 9A and 9B), IL13(EQ)BBZ+ Tcm mediated significantly improved survival and durable tumor remission with mice living >150 days as compared to our first-generation IL13-zetakine CD8+ CTL clones (FIG. 9C).

Figure 11:
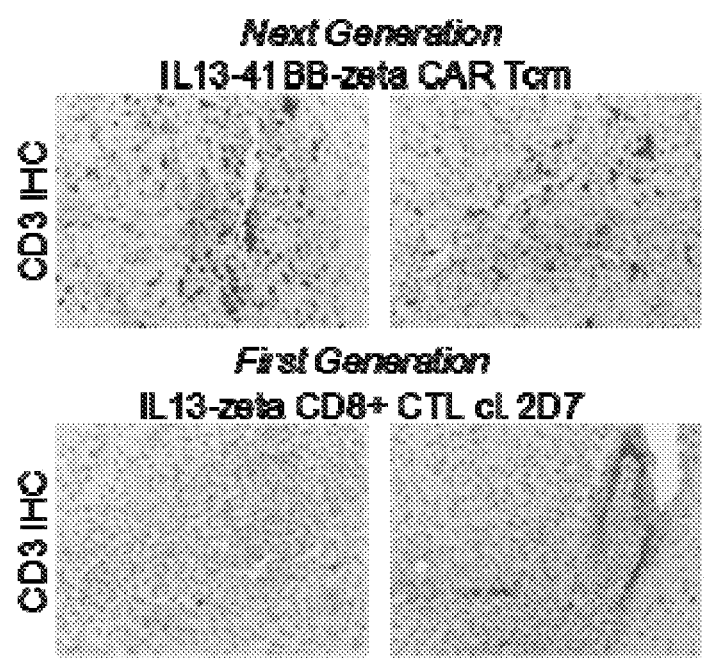
FIG. 11 depicts the results of studies demonstrating IL13 (EQ)BBζ Tcm display improved persistence compared IL13-zetakine CTL clones. CD3 immunohistochemistry evaluating T cell persistence at the tumor site 7-days post T cell infusion. Significant numbers of T cells are detected for IL13(EQ)BBζ Tcm (top panel). By contrast, very few viable CD3+ IL13-zetakine T cells are detected (bottom panel).

To further compare the therapeutic effectiveness of these two IL13Rα2-CAR T cell products, a dose titration of 1.0, 0.3 and $0.1\times10^6$ CAR T cells against day 8 PBT030-2 EGFP:ffuc TS-initiated tumors was performed (FIGS. 10A-C). The highest dose ($1\times10^6$) of IL13-zetakine CD8+ CTL cl. 2D7 mediated antitumor responses as measured by Xenogen flux in 3 of 6 animals (FIG. 10C), but no significant antitumor responses were observed at lower CART cell doses. By comparison, injection of IL13(EQ)BBζ+ Tcm product mediated complete tumor regression in the majority of mice at all dose levels, including treatment with as few as $0.1\times10^6$ CART cells. These data demonstrate that IL13(EQ)BBζ+ Tcm is at least 10-fold more potent than IL13-zetakine CD8+ CTL clones in antitumor efficacy. The improved anti-tumor efficacy of is due to improved T cell persistence in the tumor microenvironment. Evaluation of CD3+ T cells 7-days post i.c. injection revealed significant numbers of IL13(EQ)BBζ+ Tcm in the tumor microenvironment, whereas very few first-generation IL13-zeta CTLs were present (FIG. 11).

Figure 12A:
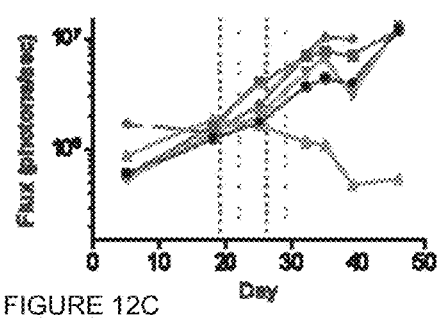
FIGS. 12A-D depict the results of experiments comparing route of CAR+ T cell delivery (i.c. versus i.v.) for large established tumors. EGFP-ffLuc+ PBT030-2 TSs (1×10$^5$) were implanted into the right forebrain of NSG mice. On days 19 and 26, mice were injected i.v. through the tail vein with either 5×10$^6$ CAR+ IL13(EQ)BBζ+ Tcm (11.8×10$^6$ total cells; n=4), or mock Tcm (11.8×10$^6$ cells; n=4). Alternatively, on days 19, 22, 26 and 29 mice were injected i.c. with either 1×10$^6$ CAR+ IL13(EQ)BBζ+ Tcm (2.4×10$^6$ total cells; n=4), or mock Tcm (2.4×10$^6$ cells; n=5). Average ffLuc flux (photons/sec) over time shows that i.c. delivered IL13 (EQ)BBζ Tcm mediates tumor regression of day 19 tumors. By comparison, i.v. delivered T cells do not shown reduction in tumor burden as compared to untreated or mock Tcm controls (A). Kaplan Meier survival curve demonstrates improved survival for mice treated i.c. IL13(EQ)BBZ Tcm as compared to mice treated with i.v. administered CAR+ Tcm (p=0.0003 log rank test) (B). Representative H&E and CD3 IHC of mice treated i.v. (C) versus i.c. (D) with IL13(EQ)BBZ+ Tcm. CD3+ T cells were only detected in the i.c. treated group, with no CD3+ cells detected in the tumor or surrounding brain parenchyma for i.v. treated mice.
Figure 12B:
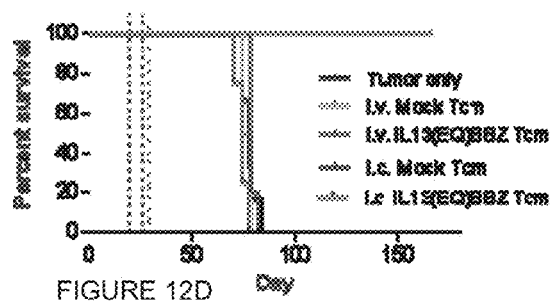
Figure 12C:
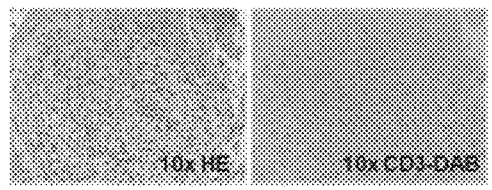
Figure 12D:
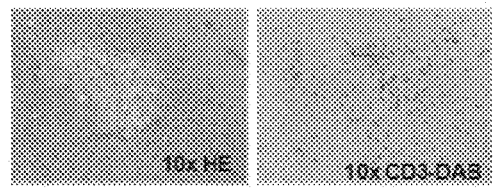

Example 9: Comparison of CART Cell Delivery Route for Treatment of Large TS-Initiated PBT Tumors Described below are studies that compare the route of delivery, intravenous (i.v.) or intracranial (i.c.), on antitumor activity against invasive primary PBT lines. In pilot studies (data not shown), it was unexpectedly observed that i.v. administered IL13(EQ)BBζ+ Tcm provided no therapeutic benefit as compared to PBS for the treatment of small (day 5) PBT030-2 EGFP:ffLuc tumors. This is in contrast to the robust therapeutic efficacy observed with i.c. administered CAR+ T cells. Reasoning that day 5 PBT030-2 tumors may have been too small to recruit therapeutic T cells from the periphery, a comparison was made of i.v. versus i.c. delivery against larger day 19 PBT030-2 EGFP:ffLuc tumors. For these studies, PBT030-2 engrafted mice were treated with either two i.v. infusions ($5\times10^6$ CAR+ Tcm; days 19 and 26) or four i.c. infusions ($1\times10^6$ CAR+ Tcm; days 19, 22, 26 and 29) of IL13(EQ)BBZ+ Tcm, or mock Tcm (no CAR). Here too no therapeutic benefit as monitored by Xenogen imaging or Kaplan-Meier survival analysis for i.v. administered CAR+ T cells (FIGS. 12A and 12B). In contrast, potent antitumor activity was observed for i.c. administered IL13(EQ)BBζ+ Tcm (FIGS. 12A-B). Next, brains from a cohort of mice 7 days post T cell injection were harvested and evaluated for CD3+ human T cells by IHC. Surprisingly, for mice treated i.v. with either mock Tcm or IL13(EQ)BBζ Tcm there were no detectable CD3+ human T cells in the tumor or in others mouse brain regions where human T cells typically reside (i.e. the leptomeninges) (FIG. 12C), suggesting a deficit in tumor tropism. This is in contrast to the significant number of T cells detected in the i.c. treated mice (FIG. 12D).

Figure 13B:
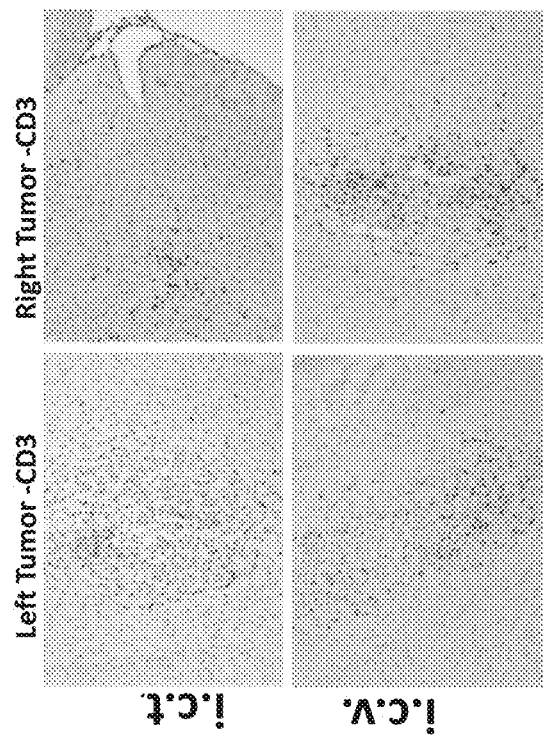
FIGS. 13A-B depict the results of studies showing that CAR+ T cell injected intracranially, either intratumoral (i.c.t.) or intraventricular (i.c.v.), can traffic to tumors on the opposite hemisphere. EGFP-ffLuc+ PBT030-2 TSs (1×105) were stereotactically implanted into the right and left forebrains of NSG mice. On day 6, mice were injected i.c. at the right tumor site with 1.0×106 IL13(EQ)BBζ+ Tcm (1.6×106 total cells; 63% CAR; n=4). Schematic of multifocal glioma experimental model (A). CD3 IHC showing T cells infiltrating both the right and left tumor sites (B).
Figure 13A:
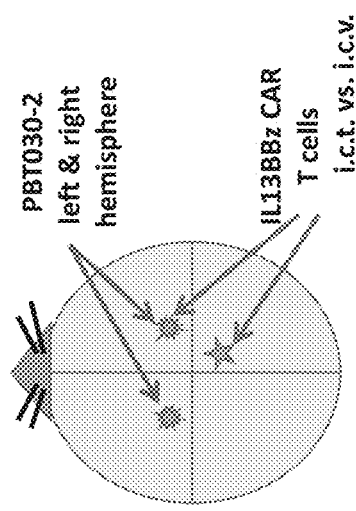

Tumor derived cytokines, particularly MCP-1/CCL2, are important in recruiting T cells to the tumor. Thus, PBT030-2 tumor cells were evaluated and it was found that this line produces high levels of MCP-1/CCL2 comparable to U251T cells (data not shown), a glioma line previously shown to attract i.v. administered effector CD8+ T cells to i.c. engrafted tumors. Malignant gliomas are highly invasive tumors and are often multifocal in presentation. The studies described above establish that IL13BBZ $T_{CM}$ can eliminate infiltrated tumors such as PBT030-2, and mediate long-term durable antitumor activity. The capacity of intracranially delivered CART cells to traffic to multifocal disease was also examined. For this study PBT030-2 EGFP:ffLuc TSs were implanted in both the left and right hemispheres (FIG. 13A) and CAR+ T cells were injected only at the right tumor site. Encouragingly, for all mice evaluated (n=3) we detected T cells by CD3 IHC 7-days post T cell infusion both at the site of injection (i.e. right tumor), as well within the tumor on the left hemisphere (FIG. 13B). These findings provide evidence that CAR+ T cells are able to traffic to and infiltrate tumor foci at distant sites. Similar findings were also observed in a second tumor model using the U251T glioma cell line (data not shown).

Example 10: Comparison of Costimulatory Domains

A series of studies were conducted to evaluate various costimulatory domains. The various CAR evaluated are depicted schematically in FIG. 14A and included a first generation CD3 CAR lacking a costimulatory domain, two second generation CARs incorporating either a 4-1BB costimulatory domain or a CD28 costimulatory domain, and a third generation CAR containing both a CD28 costimulatory domain and 41BB costimulatory domain. All CAR constructs also contain the T2A ribosomal skip sequence and a truncated CD19 (CD19t) sequence as a marker for transduced cells.

CD4 and CD8 $T_{CM}$ were lentivirally transduced and CAR-expressing T cells were immunomagnetically enriched via anti-CD19. CD19 and IL13 (i.e., CAR) expression levels as measured by flow cytometry. The results are shown in FIG. 14B. Stability of each CAR construct was determined by dividing the CAR (IL13) mean flourescence intenstity (MFI) by that of the transduction marker (CD19t) (FIG. 14C). The two CAR including a 4-1BB costimulatory domain exhibited the lowest expression levels as compared to the CD19t transduction marker.

Figure 15B:
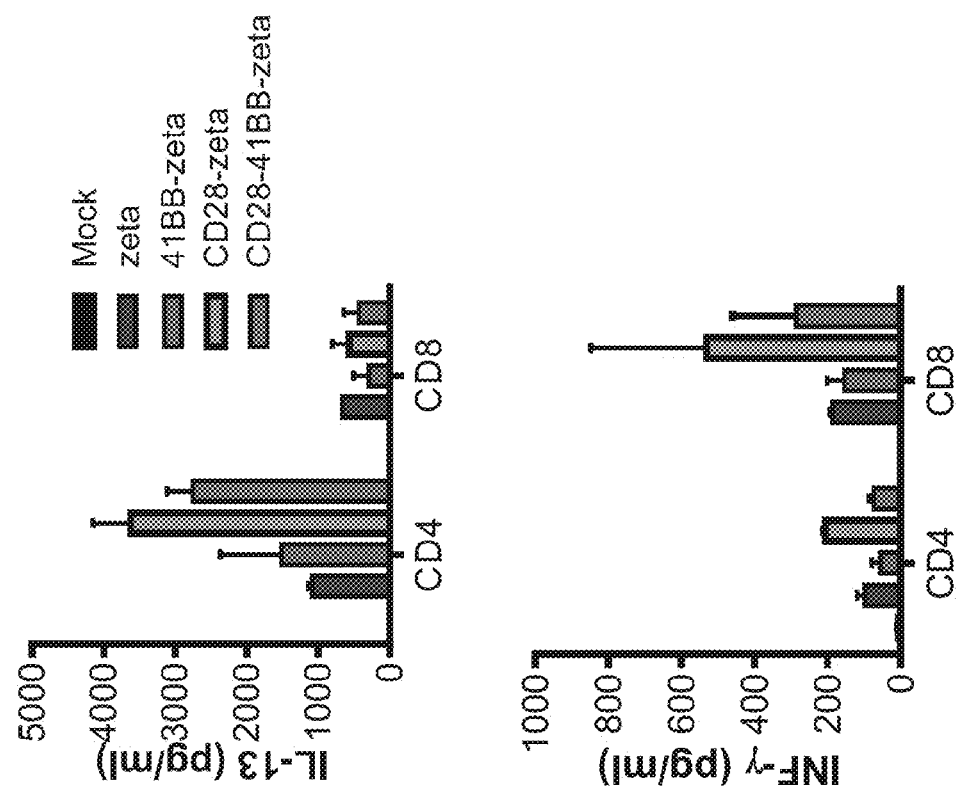
FIGS. 15A-B depict the results of studies demonstrating that IL13Rα2-specific CAR containing the 4-1BB costimulatory domain produce less Th1 and Th2 cytokines. The ability of the indicated mock-transduced or CAR-expressing T cells to kill IL13Rα2-expressing PBT030-2 tumor cell targets was determined in a 4-hour 51Cr-release assay at the indicated effector:target ratios. Mean % chromium release+ S.D. of triplicate wells are depicted (A). As expected, mock-transduced T cells did not efficiently lyse the targets. In contrast, all CAR-expressing T cells lysed the tumor cells in a similar manner. The indicated mock-transduced or CAR-expressing T cells were co-cultured overnight with IL13Rα2-expressing PBT030-2 tumor cells at a 10:1 ratio and supernatants were analyzed for IL-13 and IFN-γ levels by cytometric bead array (B). Means+S.D. of triplicate wells are depicted. Interestingly, T cells expressing the zeta, 41BB-zeta or CD28-41BB-zeta CARs exhibited lower antigen-stimulated cytokine production than T cells expressing the CD28-zeta CAR.
Figure 15A:
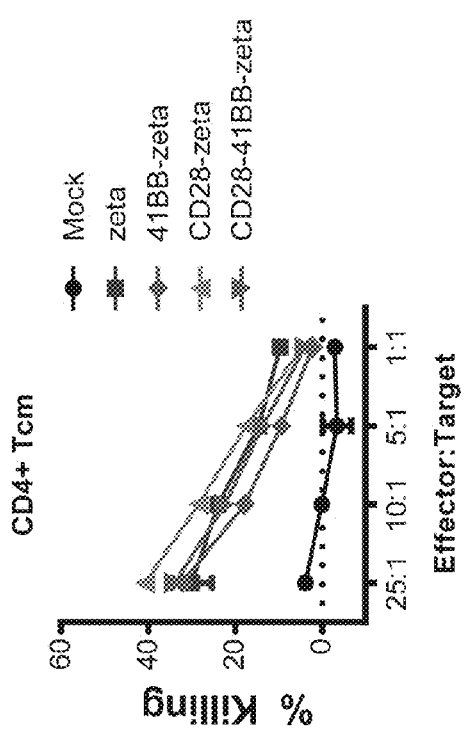

The ability of the indicated mock-transduced or CAR-expressing T cells to kill IL13Rα2-expressing PBT030-2 tumor cell targets was determined in a 4-hour $^{51}$Cr-release assay at the indicated effector:target ratios. The results of this study are in FIG. 15A (mean % chromium release±S.D. of triplicate wells are depicted). As expected, mock-transduced T cells did not efficiently lyse the targets. In contrast, all CAR-expressing T cells lysed the tumor cells in a similar manner. FIG. 15B depicts the results of a study in which the indicated mock-transduced or CAR-expressing T cells were co-cultured overnight with IL13Rα2-expressing PBT030-2 tumor cells at a 10:1 ratio and supernatants were analyzed for IL-13 and IFN-γ levels by cytometric bead array. Interestingly, T cells expressing the zeta, 41BB-zeta or CD28-41BB-zeta CARs exhibited lower antigen-stimulated cytokine production than T cells expressing the CD28-zeta CAR.

The in vivo efficacy of the various CAR was examined as follows. Briefly, NSG mice received an intracranial injection of ffLuc+ PBT030-2 tumor cells on day 0, and were randomized into 6 groups (n=9-10 mice per group) for i.c. treatment with either PBS (Tumor Only), mock-transduced T cells or T cells expressing the indicated IL13Rα2-specific CAR on day 8. Quantitative bioluminescence imaging was then carried out to monitor tumor growth over time. Bioluminescence images for representative mice in each group (FIG. 16A). Flux levels for each mouse at Day 27 (FIG. 16B). All groups treated with IL13Rα2-specific CAR T cells, except those treated with T cells expressing the CD28-CAR, show statistically-significant reduction in tumor volume compared to mice treated with mock-transduced T cells (FIG. 16C).

Example 11: Amino Acid Sequence of IL13(EQ)BBζ/CD19t

The complete amino acid sequence of IL13(EQ)BBζ/CD19t is depicted in FIGS. 17A-B. The entire sequence (SEQ ID NO:1) includes: a 22 amino acid GMCSF signal peptide (SEQ ID NO:2), a 112 amino acid IL-13 sequence (SEQ ID NO:3; amino acid substitution E13Y shown in bold); a 229 amino acid IgG4 sequence (SEQ ID NO:4; with amino acid substitutions L235E and N297Q shown in bold); a 22 amino acid CD4 transmembrane sequence (SEQ ID NO:5); a 42 amino acid 4-1BB sequence (SEQ ID NO:6); a 3 amino acid Gly linker; a 112 amino acid CD3ζ sequence (SEQ ID NO:7); a 24 amino acid T2A sequence (SEQ ID NO:8); and a 323 amino acid CD19t sequence (SEQ ID NO:9).

The mature chimeric antigen receptor sequence (SEQ ID NO:10) includes: a 112 amino acid IL-13 sequence (SEQ ID NO:3; amino acid substitution E13Y shown in bold); a 229 amino acid IgG4 sequence (SEQ ID NO:4; with amino acid substitutions L235E and N297Q shown in bold); at 22 amino acid CD4 sequence (SEQ ID NO:5); a 42 amino acid 4-1BB sequence (SEQ ID NO:6); a 3 amino acid Gly linker; and a 112 amino acid CD3ζ sequence (SEQ ID NO:7). Within this CAR sequence (SEQ ID NO:10) is the IL-13/IgG4/CD4t/41-BB sequence (SEQ ID NO:11), which includes: a 112 amino acid IL-13 sequence (SEQ ID NO:3; amino acid substitution E13Y shown in bold); a 229 amino acid IgG4 sequence (SEQ ID NO:4; with amino acid substitutions L235E and N297Q shown in bold); at 22 amino acid CD4 sequence (SEQ ID NO:5); and a 42 amino acid 4-1BB sequence (SEQ ID NO:6). The IL13/IgG4/CD4t/4-1BB sequence (SEQ ID NO:11) can be joined to the 112 amino acid CD3ζ sequence (SEQ ID NO:7) by a linker such as a Gly Gly Gly linker. The CAR sequence (SEQ ID NO:10) can be preceded by a 22 amino acid GMCSF signal peptide (SEQ ID NO:2).

FIGS. 18A-O depict a comparison of the sequences of IL13(EQ)41BBζ[IL13{EQ}41BBζ T2A-CD19t_epHIV7; pF02630] (SEQ ID NO:12) and CD19Rop_epHIV7 (pJ01683) (SEQ ID NO:13).

Example 12: Amino Acid Sequence of IL13(EQ)BBζ/CD19t

FIGS. 19-26 depict the amino acid sequences of additional CAR directed against IL13Rα2 in each case the various domains are labelled except for the GlyGlyGly spacer located between certain intracellular domains. Each includes human IL13 with and Glu to Tyr (SEQ ID NO:3; amino acid substitution E13Y shown in highlighted). In the expression vector used to express these CAR, the amino acid sequence expressed can include a 24 amino acid T2A sequence (SEQ ID NO:8); and a 323 amino acid CD19t sequence (SEQ ID NO:9) to permit coordinated expression of a truncated CD19 sequence on the surface of CAR-expressing cells.

A panel of CAR comprising human IL13(E13Y) domain, a CD28 tm domain, a CD28gg costimulatory domain, a 4-1BB costimulatory domain, and a CD3ζ domain CAR backbone and including either a HL (22 amino acids) spacer, a CD8 hinge (48 amino acids) spacer, IgG4-HL-CH3 (129 amino acids) spacer or a IgG4(EQ) (229 amino acids) spacer were tested for their ability to mediate IL13Rα2-specific killing as evaluated in a 72-hour co-culture assay. With the exception of HL (22 amino acids) which appeared to have poor CAR expression in this system, all were active.

What is claimed is:

1. A nucleic acid molecule comprising a nucleotide sequence encoding a chimeric antigen receptor molecule comprising the amino acid sequence of SEQ ID NO: 10.

2. An expression vector comprising the nucleic acid molecule of claim 1.

3. The expression vector of claim 2 wherein the expression vector is a lentiviral vector.

4. The nucleic acid molecule of claim 1 further comprising a nucleotide sequence encoding a GMSCFRa signal sequence preceding the nucleotide sequence encoding the chimeric antigen receptor.

5. The nucleic acid molecule of claim 4 wherein the GMSCFRa signal sequence comprises the amino acid sequence of SEQ ID NO:2.

6. The nucleic acid molecule of claim 4 further comprising a nucleotide sequence encoding a T2A ribosome skip sequence following the nucleotide sequence encoding the chimeric antigen receptor.

7. The nucleic acid molecule of claim 6 wherein T2A ribosome skip sequence comprises the amino acid sequence of SEQ ID NO:8.

8. An expression vector comprising the nucleic acid molecule of claim 4.

9. The expression vector of claim 8 wherein the expression vector is a lentiviral vector.

10. The nucleic acid molecule of claim 1 further comprising a nucleotide sequence encoding a T2A ribosome skip sequence following the nucleotide sequence encoding the chimeric antigen receptor.

11. The nucleic acid molecule of claim 10 wherein T2A ribosome skip sequence comprises the amino acid sequence of SEQ ID NO:8.

12. The nucleic acid molecule of claim 10 further comprising a nucleotide sequence encoding a truncated CD19 following the nucleotide sequence encoding the T2A ribosome skip sequence.

13. The nucleic acid molecule of claim 12 wherein the truncated CD19 comprises the amino acid sequence of SEQ ID NO:9.

14. The nucleic acid molecule of claim 12 wherein the truncated CD19 consists of the amino acid sequence of SEQ ID NO:9.

15. The nucleic acid molecule of claim 1 further comprising a nucleotide sequence encoding a truncated CD19.

16. The nucleic acid molecule of claim 15 wherein the truncated CD19 comprises the amino acid sequence of SEQ ID NO:9.

* * * * *

UNITED STATES PATENT AND TRADEMARK OFFICE
CERTIFICATE OF CORRECTION

PATENT NO. : 9,914,909 B2  
APPLICATION NO. : 15/167869  
DATED : March 13, 2018  
INVENTOR(S) : Christine E. Brown, Stephen J. Forman and Armen Mardiros Page 1 of 1

It is certified that error appears in the above-identified patent and that said Letters Patent is hereby corrected as shown below:

On the Title Page

Column 1, under "Inventors", after "Stephen J. Forman, Duarte, CA (US)", add -- Armen Mardiros, Duarte, CA (US) --

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 54

<210> SEQ ID NO 1
<211> LENGTH: 889
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 1

```
Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
130                 135                 140

Cys Pro Ala Pro Glu Phe Glu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Gln Ser Thr Tyr Arg Val Val Ser Val Leu Thr Val
210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350

Thr Gln Lys Ser Leu Ser Leu Ser Leu Gly Lys Met Ala Leu Ile Val
        355                 360                 365

Leu Gly Gly Val Ala Gly Leu Leu Leu Phe Ile Gly Leu Gly Ile Phe
370                 375                 380

Phe Lys Arg Gly Arg Lys Lys Leu Leu Tyr Ile Phe Lys Gln Pro Phe
385                 390                 395                 400
```

-continued

```
Met Arg Pro Val Gln Thr Thr Gln Glu Glu Asp Gly Cys Ser Cys Arg
            405                 410                 415
Phe Pro Glu Glu Glu Gly Gly Cys Glu Leu Gly Gly Gly Arg Val
        420                 425                 430
Lys Phe Ser Arg Ser Ala Asp Ala Pro Ala Tyr Gln Gln Gly Gln Asn
            435                 440                 445
Gln Leu Tyr Asn Glu Leu Asn Leu Gly Arg Arg Glu Glu Tyr Asp Val
        450                 455                 460
Leu Asp Lys Arg Arg Gly Arg Asp Pro Glu Met Gly Gly Lys Pro Arg
465                 470                 475                 480
Arg Lys Asn Pro Gln Glu Gly Leu Tyr Asn Glu Leu Gln Lys Asp Lys
            485                 490                 495
Met Ala Glu Ala Tyr Ser Glu Ile Gly Met Lys Gly Glu Arg Arg Arg
        500                 505                 510
Gly Lys Gly His Asp Gly Leu Tyr Gln Gly Leu Ser Thr Ala Thr Lys
        515                 520                 525
Asp Thr Tyr Asp Ala Leu His Met Gln Ala Leu Pro Pro Arg Leu Glu
        530                 535                 540
Gly Gly Gly Glu Gly Arg Gly Ser Leu Leu Thr Cys Gly Asp Val Glu
545                 550                 555                 560
Glu Asn Pro Gly Pro Arg Met Pro Pro Arg Leu Leu Phe Phe Leu
            565                 570                 575
Leu Phe Leu Thr Pro Met Glu Val Arg Pro Glu Glu Pro Leu Val Val
            580                 585                 590
Lys Val Glu Glu Gly Asp Asn Ala Val Leu Gln Cys Leu Lys Gly Thr
            595                 600                 605
Ser Asp Gly Pro Thr Gln Gln Leu Thr Trp Ser Arg Glu Ser Pro Leu
        610                 615                 620
Lys Pro Phe Leu Lys Leu Ser Leu Gly Leu Pro Gly Leu Gly Ile His
625                 630                 635                 640
Met Arg Pro Leu Ala Ile Trp Leu Phe Ile Phe Asn Val Ser Gln Gln
            645                 650                 655
Met Gly Gly Phe Tyr Leu Cys Gln Pro Gly Pro Pro Ser Glu Lys Ala
            660                 665                 670
Trp Gln Pro Gly Trp Thr Val Asn Val Glu Gly Ser Gly Glu Leu Phe
        675                 680                 685
Arg Trp Asn Val Ser Asp Leu Gly Gly Leu Gly Cys Gly Leu Lys Asn
        690                 695                 700
Arg Ser Ser Glu Gly Pro Ser Ser Pro Ser Gly Lys Leu Met Ser Pro
705                 710                 715                 720
Lys Leu Tyr Val Trp Ala Lys Asp Arg Pro Glu Ile Trp Glu Gly Glu
            725                 730                 735
Pro Pro Cys Val Pro Pro Arg Asp Ser Leu Asn Gln Ser Leu Ser Gln
            740                 745                 750
Asp Leu Thr Met Ala Pro Gly Ser Thr Leu Trp Leu Ser Cys Gly Val
            755                 760                 765
Pro Pro Asp Ser Val Ser Arg Gly Pro Leu Ser Trp Thr His Val His
            770                 775                 780
Pro Lys Gly Pro Lys Ser Leu Leu Ser Leu Glu Leu Lys Asp Asp Arg
785                 790                 795                 800
Pro Ala Arg Asp Met Trp Val Met Glu Thr Gly Leu Leu Leu Pro Arg
            805                 810                 815
```

```
Ala Thr Ala Gln Asp Ala Gly Lys Tyr Tyr Cys His Arg Gly Asn Leu
            820                 825                 830

Thr Met Ser Phe His Leu Glu Ile Thr Ala Arg Pro Val Leu Trp His
        835                 840                 845

Trp Leu Leu Arg Thr Gly Gly Trp Lys Val Ser Ala Val Thr Leu Ala
    850                 855                 860

Tyr Leu Ile Phe Cys Leu Cys Ser Leu Val Gly Ile Leu His Leu Gln
865                 870                 875                 880

Arg Ala Leu Val Leu Arg Arg Lys Arg
                885

<210> SEQ ID NO 2
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 3
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Pro Val Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu His Leu Lys Lys Leu Phe Arg Glu Gly Arg Phe Asn
            100                 105                 110

<210> SEQ ID NO 4
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Ser Lys Tyr Gly Pro Pro Cys Pro Pro Cys Pro Ala Pro Glu Phe
```

```
                1               5                   10                  15
            Glu Gly Gly Pro Ser Val Phe Leu Phe Pro Lys Pro Lys Asp Thr
                            20                  25                  30

Leu Met Ile Ser Arg Thr Pro Glu Val Thr Cys Val Val Asp Val
                            35                  40                  45

Ser Gln Glu Asp Pro Glu Val Gln Phe Asn Trp Tyr Val Asp Gly Val
                50                      55                      60

Glu Val His Asn Ala Lys Thr Lys Pro Arg Glu Glu Gln Phe Gln Ser
            65                      70                      75                  80

Thr Tyr Arg Val Val Ser Val Leu Thr Val Leu His Gln Asp Trp Leu
                            85                  90                  95

Asn Gly Lys Glu Tyr Lys Cys Lys Val Ser Asn Lys Gly Leu Pro Ser
                            100                 105                 110

Ser Ile Glu Lys Thr Ile Ser Lys Ala Lys Gly Gln Pro Arg Glu Pro
                            115                 120                 125

Gln Val Tyr Thr Leu Pro Pro Ser Gln Glu Glu Met Thr Lys Asn Gln
                            130                 135                 140

Val Ser Leu Thr Cys Leu Val Lys Gly Phe Tyr Pro Ser Asp Ile Ala
            145                     150                     155                 160

Val Glu Trp Glu Ser Asn Gly Gln Pro Glu Asn Asn Tyr Lys Thr Thr
                            165                 170                 175

Pro Pro Val Leu Asp Ser Asp Gly Ser Phe Phe Leu Tyr Ser Arg Leu
                            180                 185                 190

Thr Val Asp Lys Ser Arg Trp Gln Gln Gly Asn Val Phe Ser Cys Ser
                            195                 200                 205

Val Met His Glu Ala Leu His Asn His Tyr Thr Gln Lys Ser Leu Ser
                            210                 215                 220

Leu Ser Leu Gly Lys
            225
```

<210> SEQ ID NO 5
<211> LENGTH: 22
<212> TYPE: PRT
<213> ORGANISM: Homo sapiens

<400> SEQUENCE: 5

```
            Met Ala Leu Ile Val Leu Gly Gly Val Ala Gly Leu Leu Leu Phe Ile
            1               5                   10                  15

Gly Leu Gly Ile Phe Phe
                            20
```

<210> SEQ ID NO 6
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
            Lys Arg Gly Arg Lys Lys Leu Leu Tyr Ile Phe Lys Gln Pro Phe Met
            1               5                   10                  15

Arg Pro Val Gln Thr Thr Gln Glu Glu Asp Gly Cys Ser Cys Arg Phe
                            20                  25                  30

Pro Glu Glu Glu Glu Gly Gly Cys Glu Leu
                            35                  40
```

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 9
<211> LENGTH: 323
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu

```
                    85                  90                  95
Cys Gln Pro Gly Pro Ser Glu Lys Ala Trp Gln Pro Gly Trp Thr
                100                 105                 110

Val Asn Val Glu Gly Ser Gly Glu Leu Phe Arg Trp Asn Val Ser Asp
                115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Asp Ser Val Ser
                195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
                275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg

<210> SEQ ID NO 10
<211> LENGTH: 520
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110
```

-continued

```
Glu Ser Lys Tyr Gly Pro Pro Cys Pro Pro Cys Pro Ala Pro Glu Phe
            115                 120                 125
Glu Gly Gly Pro Ser Val Phe Leu Phe Pro Pro Lys Pro Lys Asp Thr
        130                 135                 140
Leu Met Ile Ser Arg Thr Pro Glu Val Thr Cys Val Val Val Asp Val
145                 150                 155                 160
Ser Gln Glu Asp Pro Glu Val Gln Phe Asn Trp Tyr Val Asp Gly Val
                165                 170                 175
Glu Val His Asn Ala Lys Thr Lys Pro Arg Glu Glu Gln Phe Gln Ser
            180                 185                 190
Thr Tyr Arg Val Val Ser Val Leu Thr Val Leu His Gln Asp Trp Leu
        195                 200                 205
Asn Gly Lys Glu Tyr Lys Cys Lys Val Ser Asn Lys Gly Leu Pro Ser
210                 215                 220
Ser Ile Glu Lys Thr Ile Ser Lys Ala Lys Gly Gln Pro Arg Glu Pro
225                 230                 235                 240
Gln Val Tyr Thr Leu Pro Pro Ser Gln Glu Glu Met Thr Lys Asn Gln
                245                 250                 255
Val Ser Leu Thr Cys Leu Val Lys Gly Phe Tyr Pro Ser Asp Ile Ala
            260                 265                 270
Val Glu Trp Glu Ser Asn Gly Gln Pro Glu Asn Asn Tyr Lys Thr Thr
        275                 280                 285
Pro Pro Val Leu Asp Ser Asp Gly Ser Phe Phe Leu Tyr Ser Arg Leu
290                 295                 300
Thr Val Asp Lys Ser Arg Trp Gln Glu Gly Asn Val Phe Ser Cys Ser
305                 310                 315                 320
Val Met His Glu Ala Leu His Asn His Tyr Thr Gln Lys Ser Leu Ser
                325                 330                 335
Leu Ser Leu Gly Lys Met Ala Leu Ile Val Leu Gly Gly Val Ala Gly
            340                 345                 350
Leu Leu Leu Phe Ile Gly Leu Gly Ile Phe Phe Lys Arg Gly Arg Lys
        355                 360                 365
Lys Leu Leu Tyr Ile Phe Lys Gln Pro Phe Met Arg Pro Val Gln Thr
370                 375                 380
Thr Gln Glu Glu Asp Gly Cys Ser Cys Arg Phe Pro Glu Glu Glu Glu
385                 390                 395                 400
Gly Gly Cys Glu Leu Gly Gly Gly Arg Val Lys Phe Ser Arg Ser Ala
                405                 410                 415
Asp Ala Pro Ala Tyr Gln Gln Gly Gln Asn Gln Leu Tyr Asn Glu Leu
            420                 425                 430
Asn Leu Gly Arg Arg Glu Glu Tyr Asp Val Leu Asp Lys Arg Arg Gly
        435                 440                 445
Arg Asp Pro Glu Met Gly Gly Lys Pro Arg Arg Lys Asn Pro Gln Glu
450                 455                 460
Gly Leu Tyr Asn Glu Leu Gln Lys Asp Lys Met Ala Glu Ala Tyr Ser
465                 470                 475                 480
Glu Ile Gly Met Lys Gly Glu Arg Arg Arg Gly Lys Gly His Asp Gly
                485                 490                 495
Leu Tyr Gln Gly Leu Ser Thr Ala Thr Lys Asp Thr Tyr Asp Ala Leu
            500                 505                 510
His Met Gln Ala Leu Pro Pro Arg
        515                 520
```

```
<210> SEQ ID NO 11
<211> LENGTH: 405
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Ala Pro Glu Phe
        115                 120                 125

Glu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
    290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Leu Gly Lys Met Ala Leu Ile Val Leu Gly Val Ala Gly
            340                 345                 350

Leu Leu Leu Phe Ile Gly Leu Gly Ile Phe Phe Lys Arg Gly Arg Lys
        355                 360                 365

```
Lys Leu Leu Tyr Ile Phe Lys Gln Pro Phe Met Arg Pro Val Gln Thr
        370                 375                 380

Thr Gln Glu Glu Asp Gly Cys Ser Cys Arg Phe Pro Glu Glu Glu Glu
385                 390                 395                 400

Gly Gly Cys Glu Leu
            405

<210> SEQ ID NO 12
<211> LENGTH: 7754
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
gttagaccag atctgagcct gggagctctc tggctaacta gggaacccac tgcttaagcc     60
tcaataaagc ttgccttgag tgcttcaagt agtgtgtgcc cgtctgttgt gtgactctgg    120
taactagaga tccctcagac ccttttagtc agtgtggaaa atctctagca gtggcgcccg    180
aacagggact tgaaagcgaa agggaaacca gaggagctct ctcgacgcag gactcggctt    240
gctgaagcgc gcacggcaag aggcgagggg cggcgactgg tgagtacgcc aaaaattttg    300
actagcggag gctagaagga gagagatggg tgcgagagcg tcagtattaa gcggggggaga    360 attagatcga tgggaaaaaa ttcggttaag gccagggggaa agaaaaaat ataaattaaa    420 acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt gggggagggg tcggcaatt gaaccggtgc   1620 ctagagaagt ggcgcggggg taaactggga aagtgatgtc gtgtactggc tccgcctttt   1680
tcccgagggt gggggagaac cgtatataag tgcagtagtc gccgtgaacg ttcttttcg   1740
```

```
caacgggttt gccgccagaa cacagctgaa gcttcgaggg gctcgcatct ctccttcacg    1800
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
accgggcctt tgtccggcgc tcccttggag cctacctaga ctcagccggc tctccacgct    1980
ttgcctgacc ctgcttgctc aactctacgt ctttgtttcg ttttctgttc tgcgccgtta    2040
cagatccaag ctgtgaccgg cgcctacggc tagcgccgcc accatgctgc tgctggtgac    2100
cagcctgctg ctgtgcgagc tgccccaccc cgccttcctg ctgatccctg ccccgtgcc    2160 ccctagcacc gccctgcgct acctgatcga ggaactggtg aacatcaccc agaaccagaa    2220 agccccctg tgcaacggca gcatggtgtg agcatcaac ctgaccgccg gcatgtactg    2280
tgccgccctg gaaagcctga tcaacgtgag cggctgcagc gccatcgaga aaacccagcg    2340
gatgctgtcc ggcttctgcc cccacaaggt gtccgccgga cagttcagca gcctgcacgt    2400
gcgggacacc aagatcgagg tggcccagtt cgtgaaggac ctgctgctgc acctgaagaa    2460
gctgttccgg gagggccggt tcaactacaa gaccaccccc cctgtgctgg acagcgacgg    2520
cagcttcttc ctgtacagca ggctgaccgt ggacaagagc cggtggcagg aaggcaacgt    2580 cttagctgc agcgtgatgc acgaggccct gcacaaccac tacacccaga gagcctgtc    2640 cctgagcctg ggcaagcggg tgaagttcag ccggtccgcc gacgcccctg cctaccagca    2700
gggccagaac cagctgtaca cgagctgaa cctgggcagg cgggaggaat acgacgtgct    2760
ggacaagcgg agaggccggg accctgagat gggcggcaag cctcggcgga agaaccccca    2820
ggaaggcctg tataacgaac tgcagaaaga caagatggcc gaggcctaca gcgagatcgg    2880
catgaagggc gagcggaggc gggcaagggc ccacgacggc ctgtatcagg gcctgtccac    2940
cgccaccaag gatacctacg acgccctgca catgcaggcc ctgccccaa ggtctagacc    3000 cgggctgcag gaattcgata tcaagcttat cgataatcaa cctctggatt acaaaatttg    3060
tgaaagattg actggtattc ttaactatgt tgctcctttt acgctatgtg gatacgctgc    3120
tttaatgcct ttgtatcatg ctattgcttc ccgtatggct ttcattttct cctccttgta    3180
taaatcctgg ttgctgtctc tttatgagga gttgtggccc gttgtcaggc aacgtggcgt    3240
ggtgtgcact gtgtttgctg acgcaacccc cactggttgg ggcattgcca ccacctgtca    3300 gctccttcc gggactttcg ctttcccccct cctattgcc acggcggaac tcatcgccgc    3360
ctgccttgcc cgctgctgga caggggctcg gctgttgggc actgacaatt ccgtggtgtt    3420
gtcggggaaa tcatcgtcct ttccttggct gctcgcctgt gttgccacct ggattctgcg    3480
cgggacgtcc ttctgctacg tcccttcggc cctcaatcca gcggaccttc cttcccgcgg    3540
cctgctgccg gtctgcggc ctcttccgcg tcttcgcctt cgccctcaga cgagtcggat    3600
ctccctttgg gccgcctccc cgcatcgata ccgtcgacta ccgtaccttt aagaccaat    3660 gacttacaag gcagctgtag atcttagcca cttttaaaa gaaaggggg gactggaagg    3720 gctaattcac tcccaaagaa gacaagatct gcttttgcc tgtactgggt ctctctggtt    3780
agaccagatc tgagcctggg agctctctgg ctaactaggg aacccactgc ttaagcctca    3840
ataaagcttg ccttgagtgc ttcaagtagt gtgtgcccgt ctgttgtgtg actctggtaa    3900
ctagagatcc ctcagaccct tttagtcagt gtggaaaatc tctagcagaa ttcgatatca    3960
agcttatcga taccgtcgac ctcgaggggg gcccggtac ccaattcgcc ctatagtgag    4020
tcgtattaca attcactggc cgtcgtttta caacgtcgtg actgggaaaa ccctggcgtt    4080
```

-continued

```
acccaactta atcgccttgc agcacatccc cctttcgcca gctggcgtaa tagcgaagag    4140
gcccgcaccg atcgcccttc ccaacagttg cgcagcctga atggcgaatg gaaattgtaa    4200
gcgttaatat tttgttaaaa ttcgcgttaa attttttgtta aatcagctca tttttttaacc   4260 aataggccga aatcggcaaa atcccttata aatcaaaaga atagaccgag atagggttga   4320
gtgttgttcc agtttggaac aagagtccac tattaaagaa cgtggactcc aacgtcaaag    4380
ggcgaaaaac cgtctatcag ggcgatggcc cactacgtga accatcaccc taatcaagtt    4440 tttttggggtc gaggtgccgt aaagcactaa atcggaaccc taaagggagc ccccgattta    4500
gagcttgacg gggaaagccg cgaacgtgg cgagaaagga agggaagaaa gcgaaaggag    4560
cgggcgctag ggcgctggca agtgtagcgg tcacgctgcg cgtaaccacc acaccgccg    4620 cgcttaatgc gccgctacag ggcgcgtcag gtggcacttt tcggggaaat gtgcgcggaa    4680
cccctatttg tttattttttc taaatacatt caaatatgta tccgctcatg agacaataac    4740
cctgataaat gcttcaataa tattgaaaaa ggaagagtat gagtattcaa catttccgtg    4800
tcgcccttat tcccttttttt gcggcatttt gccttcctgt ttttgctcac ccagaaacgc    4860
tggtgaaagt aaaagatgct gaagatcagt tgggtgcacg agtgggttac atcgaactgg    4920
atctcaacag cggtaagatc cttgagagtt ttcgccccga agaacgtttt ccaatgatga    4980
gcacttttaa agttctgcta tgtggcgcgg tattatcccg tattgacgcc gggcaagagc    5040
aactcggtcg ccgcatacac tattctcaga atgacttggt tgagtactca ccagtcacag    5100
aaaagcatct tacggatggc atgacagtaa gagaattatg cagtgctgcc ataaccatga    5160
gtgataacac tgcggccaac ttacttctga caacgatcgg aggaccgaag gagctaaccg    5220
cttttttgca acatggggg gatcatgtaa ctcgccttga tcgttgggaa ccggagctga    5280
atgaagccat accaaacgac gagcgtgaca ccacgatgcc tgtagcaatg caacaacgt    5340 tgcgcaaact attaactggc gaactactta ctctagcttc ccggcaacaa ttaatagact    5400
ggatggaggc ggataaagtt gcaggaccac ttctgcgctc ggcccttccg gctggctggt    5460
ttattgctga taaatctgga gccggtgagc gtgggtctcg cggtatcatt gcagcactgg    5520
ggccagatgg taagccctcc cgtatcgtag ttatctacac gacggggagt caggcaacta    5580
tggatgaacg aaatagacag atcgctgaga taggtgcctc actgattaag cattggtaac    5640
tgtcagacca agtttactca tatatacttt agattgattt aaaacttcat ttttaattta    5700
aaaggatcta ggtgaagatc ctttttgata atctcatgac caaaatccct taacgtgagt    5760
tttcgttcca ctgagcgtca gaccccgtag aaaagatcaa aggatcttct tgagatcctt    5820 ttttttctgcg cgtaatctgc tgcttgcaaa caaaaaaacc accgctacca gcggtggttt    5880
gtttgccgga tcaagagcta ccaactcttt ttccgaaggt aactggcttc agcagagcgc    5940
agataccaaa tactgttctt ctagtgtagc cgtagttagg ccaccacttc aagaactctg    6000
tagcaccgcc tacatacctc gctctgctaa tcctgttacc agtggctgct gccagtggcg    6060
ataagtcgtg tcttaccggg ttggactcaa gacgatagtt accggataag cgcagcggt    6120 cgggctgaac ggggggttcg tgcacacagc ccagcttgga gcgaacgacc tacaccgaac    6180
tgagatacct acagcgtgag ctatgagaaa gcgccacgct tcccgaaggg agaaaggcgg    6240
acaggtatcc ggtaagcggc agggtcggaa caggagagcg cacgagggag cttccagggg    6300
gaaacgcctg gtatctttat agtcctgtcg ggtttcgcca cctctgactt gagcgtcgat    6360
ttttgtgatg ctcgtcaggg gggcggagcc tatgaaaaaa cgccagcaac gcggcctttt    6420
tacggttcct ggccttttgc tggccttttg ctcacatgtt cttttcctgcg ttatcccctg    6480
```

```
attctgtgga taaccgtatt accgcctttg agtgagctga taccgctcgc cgcagccgaa    6540
cgaccgagcg cagcgagtca gtgagcgagg aagcggaaga gcgcccaata cgcaaaccgc    6600
ctctccccgc gcgttggccg attcattaat gcagctggca cgacaggttt cccgactgga    6660
aagcgggcag tgagcgcaac gcaattaatg tgagttagct cactcattag gcaccccagg    6720
ctttacactt tatgcttccg gctcgtatgt tgtgtggaat tgtgagcgga taacaatttc    6780
acacaggaaa cagctatgac catgattacg ccaagctcga attaaccct cactaaaggg    6840 aacaaaagct ggagctccac cgcggtggcg gcctcgaggt cgagatccgg tcgaccagca    6900
accatagtcc cgcccctaac tccgcccatc ccgcccctaa ctccgcccag ttccgcccat    6960
tctccgcccc atggctgact aattttttt atttatgcag aggccgaggc cgcctcggcc    7020
tctgagctat tccagaagta gtgaggaggc ttttttggag gcctaggctt ttgcaaaaag    7080
cttcgacggt atcgattggc tcatgtccaa cattaccgcc atgttgacat tgattattga    7140
ctagttatta atagtaatca attacggggt cattagttca tagcccatat atggagttcc    7200
gcgttacata acttacggta atggcccgc ctggctgacc gcccaacgac ccccgcccat    7260
tgacgtcaat aatgacgtat gttcccatag taacgccaat agggactttc cattgacgtc    7320
aatgggtgga gtatttacgg taaactgccc acttggcagt acatcaagtg tatcatatgc    7380
caagtacgcc ccctattgac gtcaatgacg gtaaatggcc cgcctggcat tatgcccagt    7440
acatgacctt atgggacttt cctacttggc agtacatcta cgtattagtc atcgctatta    7500
ccatggtgat gcggttttgg cagtacatca atgggcgtgg atagcggttt gactcacggg    7560
gatttccaag tctccacccc attgacgtca atgggagttt gttttggcac caaaatcaac    7620
gggactttcc aaaatgtcgt aacaactccg ccccattgac gcaaatgggc ggtaggcgtg    7680
tacggaattc ggagtggcga gccctcgat cctgcatata agcagctgct ttttgcctgt    7740
actgggtctc tctg                                                     7754
```

<210> SEQ ID NO 13
<211> LENGTH: 8732
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac cctttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcgggggaga     360
attagatcga tgggaaaaaa ttcggttaag gccagggga aagaaaaaat ataaattaaa     420
acatatagta tgggcaagca gggagctaga acgattcga gttaatcctg gcctgttaga     480
aacatcagaa ggctgtagac aaatactggg acagctacaa ccatcccttc agacaggatc     540
agaagaactt agatcattat ataatacagt agcaacctc tattgtgtgc atcaaaggat     600
agagataaaa gacaccaagg aagctttaga caagatagag gaagagcaaa acaaaagtaa     660
```

```
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaagggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt gggggagggg tcggcaattg aaccggtgc    1620
ctagagaagg tggcgcgggg taaactggga aagtgatgtc gtgtactggc tccgcctttt   1680
tccccgagggt gggggagaac cgtatataag tgcagtagtc gccgtgaacg ttcttttttcg   1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt cttttgtttcg ttttctgttc tgcgccgtta   2040
cagatccaag ctgtgaccgg cgcctacggc tagcgccgcc accatgctgc tgctggtgac   2100
cagcctgctg ctgtgcgagc tgccccaccc cgccttttctg ctgatccccg acatccagat   2160
gacccagacc acctccagcc tgagcgccag cctgggcgac cgggtgacca tcagctgccg   2220
ggccagccag gacatcagca gtacctgaaa ctggtatcag cagaagcccg acggcaccgt   2280
caagctgctg atctaccaca ccagccggct gcacagcggc gtgcccagcc ggtttagcgg   2340
cagcggctcc ggcaccgact acagcctgac catctccaac ctggaacagg aagatatcgc   2400
cacctacttt tgccagcagg gcaacacact gccctacacc tttggcggcg gaacaaagct   2460
ggaaatcacc ggcagcacct ccggcagcgg caagcctggc agcggcgagg gcagcaccaa   2520
gggcgaggtg aagctgcagg aaagcggccc tggcctggtg gcccccagcc agagcctgag   2580
cgtgacctgc accgtgagcg gcgtgagcct gcccgactac ggcgtgagct ggatccggca   2640
gcccccccagg aagggcctgg aatggctggg cgtgatctgg ggcagcgaga ccacctacta   2700
caacagcgcc ctgaagagcc ggctgaccat catcaaggac aacagcaaga gccaggtgtt   2760
cctgaagatg aacagcctgc agaccgacga caccgccatc tactactgcg ccaagcacta   2820
ctactacggc ggcagctacg ccatggacta ctggggccag ggcaccagcg tgaccgtgag   2880
cagcgagagc aagtacggcc ctccctgccc ccttgccct gccccgagt tcctgggcgg   2940
acccagcgtg ttcctgttcc cccccaagcc caaggacacc ctgatgatca gccggacccc   3000
cgaggtgacc tgcgtggtgg tggacgtgag ccaggaagat cccgaggtcc agttcaattg   3060
```

-continued

```
gtacgtggac ggcgtggagg tgcacaacgc caagaccaag cccagggaag agcagttcaa    3120
cagcacctac cgggtggtgt ccgtgctgac cgtgctgcac caggactggc tgaacggcaa    3180
agaatacaag tgcaaggtgt ccaacaaggg cctgcccagc agcatcgaga aaaccatcag    3240
caaggccaag ggccagcctc gggagcccca ggtgtacacc ctgccccctt ccaggaaga    3300 gatgaccaag aatcaggtgt ccctgacctg cctggtgaag ggcttctacc ccagcgacat    3360
cgccgtggag tgggagagca acggccagcc cgagaacaac tacaagacca ccccccctgt    3420
gctggacagc gacggcagct tcttcctgta cagcaggctg accgtggaca gagccggtg    3480 gcaggaaggc aacgtcttta gctgcagcgt gatgcacgag gccctgcaca accactacac    3540
ccagaagagc ctgtccctga gcctgggcaa gatggccctg atcgtgctgg gcggcgtggc    3600
cgggctgctg ctgttcatcg gcctgggcat cttttttccgg gtgaagttca gccggtccgc    3660
cgacgcccct gcctaccagc agggccagaa ccagctgtac aacgagctga acctgggcag    3720
gcgggaggaa tacgacgtgc tggacaagcg agaggccgg gaccctgaga tgggcggcaa    3780
gcccaggcgg aagaaccctc aggaaggcct gtataacgaa ctgcagaaag acaagatggc    3840
cgaggcctac agcgagatcg gcatgaaggg cgagcggcgg aggggcaagg ccacgacgg    3900 cctgtaccag ggcctgagca ccgccaccaa ggatacctac gacgccctgc acatgcaggc    3960
cctgcccccc aggtgacccg ggctgcagga attcgatatc aagcttatcg ataatcaacc    4020
tctggattac aaaatttgtg aaagattgac tggtattctt aactatgttg ctccttttac    4080
gctatgtgga tacgctgctt taatgccttt gtatcatgct attgcttccc gtatggcttt    4140
cattttctcc tccttgtata atcctggtt gctgtctctt tatgaggagt tgtggcccgt    4200
tgtcaggcaa cgtggcgtgg tgtgcactgt gtttgctgac gcaaccccca ctggttgggg    4260
cattgccacc acctgtcagc tcctttccgg gactttcgct ttccccctcc ctattgccac    4320
ggcggaactc atcgccgcct gccttgcccg ctgctggaca ggggctcggc tgttgggcac    4380
tgacaattcc gtggtgttgt cggggaaatc atcgtccttt ccttggctgc tcgcctgtgt    4440
tgccacctgg attctgcgcg ggacgtcctt ctgctacgtc ccttcggccc tcaatccagc    4500
ggaccttcct tcccgcggcc tgctgccggc tctgcggcct cttccgcgtc ttcgccttcg    4560
ccctcagacg agtcggatct ccctttgggc cgcctccccg catcgatacc gtcgactagc    4620
cgtaccttta agaccaatga cttacaaggc agctgtagat cttagccact ttttaaaaga    4680
aaagggggga ctggaagggc taattcactc ccaaagaaga caagatctgc ttttttgcctg    4740 tactgggtct ctctggttag accagatctg agcctgggag ctctctggct aactaggaa    4800 cccactgctt aagcctcaat aaagcttgcc ttgagtgctt caagtagtgt gtgcccgtct    4860
gttgtgtgac tctggtaact agagatccct cagaccctt tagtcagtgt ggaaaatctc    4920
tagcagaatt cgatatcaag cttatcgata ccgtcgacct cgagggggg cccggtaccc    4980 aattcgccct atagtgagtc gtattacaat tcactggccg tcgttttaca acgtcgtgac    5040
tgggaaaacc ctggcgttac ccaacttaat cgccttgcag cacatccccc tttcgccagc    5100
tggcgtaata gcgaagaggc ccgcaccgat cgcccttccc aacagttgcg cagcctgaat    5160
ggcgaatgga aattgtaagc gttaatattt tgttaaaatt cgcgttaaat ttttgttaaa    5220
tcagctcatt ttttaaccaa taggccgaaa tcggcaaaat cccttataaa tcaaaagaat    5280
agaccgagat agggttgagt gttgttccag tttggaacaa gagtccacta ttaaagaacg    5340
tggactccaa cgtcaaaggg cgaaaaaccg tctatcaggg cgatggccca ctacgtgaac    5400
```

```
catcaccta atcaagtttt tgggggtcga ggtgccgtaa agcactaaat cggaaccta    5460
aagggagccc ccgatttaga gcttgacggg gaaagccggc gaacgtggcg agaaaggaag    5520
ggaagaaagc gaaaggagcg ggcgctaggg cgctggcaag tgtagcggtc acgctgcgcg    5580
taaccaccac acccgccgcg cttaatgcgc cgctacaggg cgcgtcaggt ggcacttttc    5640
ggggaaatgt gcgcggaacc cctatttgtt tatttttcta atacattca aatatgtatc    5700
cgctcatgag acaataaccc tgataaatgc ttcaataata ttgaaaaagg aagagtatga    5760
gtattcaaca tttccgtgtc gcccttattc ccttttttgc ggcattttgc cttcctgttt    5820
ttgctcaccc agaaacgctg gtgaaagtaa aagatgctga agatcagttg ggtgcacgag    5880
tgggttacat cgaactggat ctcaacagcg gtaagatcct tgagagtttt cgccccgaag    5940
aacgttttcc aatgatgagc acttttaaag ttctgctatg tggcgcggta ttatcccgta    6000
ttgacgccgg gcaagagcaa ctcggtcgcc gcatacacta ttctcagaat gacttggttg    6060
agtactcacc agtcacagaa aagcatctta cggatggcat gacagtaaga gaattatgca    6120
gtgctgccat aaccatgagt gataacactg cggccaactt acttctgaca acgatcggag    6180
gaccgaagga gctaaccgct tttttgcaca acatggggga tcatgtaact cgccttgatc    6240
gttgggaacc ggagctgaat gaagccatac caaacgacga gcgtgacacc acgatgcctg    6300
tagcaatggc aacaacgttg cgcaaactat taactggcga actacttact ctagcttccc    6360
ggcaacaatt aatagactgg atggaggcgg ataaagttgc aggaccactt ctgcgctcgg    6420
cccttccggc tggctggttt attgctgata aatctggagc cggtgagcgt gggtctcgcg    6480
gtatcattgc agcactgggg ccagatggta agccctcccg tatcgtagtt atctacacga    6540
cggggagtca ggcaactatg gatgaacgaa atagacagat cgctgagata ggtgcctcac    6600
tgattaagca ttggtaactg tcagaccaag tttactcata tatactttag attgatttaa    6660
aacttcattt ttaatttaaa aggatctagg tgaagatcct ttttgataat ctcatgacca    6720
aaatccctta acgtgagttt tcgttccact gagcgtcaga ccccgtagaa aagatcaaag    6780
gatcttcttg agatcctttt tttctgcgcg taatctgctg cttgcaaaca aaaaaaccac    6840
cgctaccagc ggtggtttgt ttgccggatc aagagctacc aactcttttt ccgaaggtaa    6900
ctggcttcag cagagcgcag ataccaaata ctgttcttct agtgtagccg tagttaggcc    6960
accacttcaa gaactctgta gcaccgccta catacctcgc tctgctaatc ctgttaccag    7020
tggctgctgc cagtggcgat aagtcgtgtc ttaccgggtt ggactcaaga cgatagttac    7080
cggataaggc gcagcggtcg ggctgaacgg ggggttcgtg cacacagccc agcttggagc    7140
gaacgaccta caccgaactg agatacctac agcgtgagct atgagaaagc gccacgcttc    7200
ccgaagggag aaaggcggac aggtatccgg taagcggcag ggtcggaaca ggagagcgca    7260
cgagggagct tccaggggga aacgcctggt atctttatag tcctgtcggg tttcgccacc    7320
tctgacttga gcgtcgattt ttgtgatgct cgtcaggggg gcggagccta tggaaaaacg    7380
ccagcaacgc ggccttttta cggttcctgg ccttttgctg gccttttgct cacatgttct    7440
ttcctgcgtt atcccctgat tctgtggata accgtattac cgcctttgag tgagctgata    7500
ccgctcgccg cagccgaacg accgagcgca gcgagtcagt gagcgaggaa gcggaagagc    7560
gcccaatacg caaaccgcct ctccccgcgc gttggccgat tcattaatgc agctggcacg    7620
acaggtttcc cgactggaaa gcgggcagtg agcgcaacgc aattaatgtg agttagctca    7680
ctcattaggc accccaggct ttacacttta tgcttccggc tcgtatgttg tgtggaattg    7740
tgagcggata acaatttcac acaggaaaca gctatgacca tgattacgcc aagctcgaaa    7800
```

```
ttaaccctca ctaaagggaa caaaagctgg agctccaccg cggtggcggc ctcgaggtcg    7860
agatccggtc gaccagcaac catagtcccg cccctaactc cgcccatccc gcccctaact    7920
ccgcccagtt ccgcccattc tccgccccat ggctgactaa ttttttttat ttatgcagag    7980
gccgaggccg cctcggcctc tgagctattc cagaagtagt gaggaggctt ttttggaggc    8040
ctaggctttt gcaaaaagct tcgacggtat cgattggctc atgtccaaca ttaccgccat    8100
gttgacattg attattgact agttattaat agtaatcaat tacggggtca ttagttcata    8160
gcccatatat ggagttccgc gttacataac ttacggtaaa tggcccgcct ggctgaccgc    8220
ccaacgaccc ccgcccattg acgtcaataa tgacgtatgt tcccatagta acgccaatag    8280
ggactttcca ttgacgtcaa tgggtggagt atttacggta aactgcccac ttggcagtac    8340
atcaagtgta tcatatgcca agtacgcccc ctattgacgt caatgacggt aaatggcccg    8400
cctggcatta tgcccagtac atgaccttat gggactttcc tacttggcag tacatctacg    8460
tattagtcat cgctattacc atggtgatgc ggttttggca gtacatcaat gggcgtggat    8520
agcggtttga ctcacgggga tttccaagtc tccaccccat tgacgtcaat gggagtttgt    8580
tttggcacca aaatcaacgg gactttccaa aatgtcgtaa caactccgcc ccattgacgc    8640
aaatgggcgg taggcgtgta cggaattcgg agtggcgagc cctcagatcc tgcatataag    8700
cagctgcttt tgcctgtac tgggtctctc tg                                   8732
```

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Gly Ser Ser Gly Gly Gly Ser Gly
1               5                   10

<210> SEQ ID NO 15
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Glu Ser Lys Tyr Gly Pro Pro Cys Pro Pro Cys Pro
1               5                   10

<210> SEQ ID NO 16
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Ser Lys Tyr Gly Pro Pro Cys Pro Pro Cys Pro Gly Gly Gly Ser
1               5                   10                  15

Ser Gly Gly Gly Ser Gly

20

<210> SEQ ID NO 17
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro
            35
```

<210> SEQ ID NO 18
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45
```

<210> SEQ ID NO 19
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45
```

<210> SEQ ID NO 20
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Glu Ser Lys Tyr Gly Pro Pro Cys Pro Pro Cys Pro Gly Gly Gly Ser
1               5                   10                  15
```

```
Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 21
<211> LENGTH: 21
<212> TYPE: PRT
<213> ORGANISM: Homo sapiens

<400> SEQUENCE: 21

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 22
<211> LENGTH: 27
<212> TYPE: PRT
<213> ORGANISM: Homo sapiens

<400> SEQUENCE: 22

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 23
<211> LENGTH: 21
<212> TYPE: PRT
<213> ORGANISM: Homo sapiens

<400> SEQUENCE: 23

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 24
<211> LENGTH: 23
<212> TYPE: PRT
<213> ORGANISM: Homo sapiens

<400> SEQUENCE: 24

Ile Tyr Ile Trp Ala Pro Leu Ala Gly Thr Cys Gly Val Leu Leu Leu
1               5                   10                  15

Ser Leu Val Ile Thr Leu Tyr
            20
```

<210> SEQ ID NO 25
<211> LENGTH: 24
<212> TYPE: PRT
<213> ORGANISM: Homo sapiens

<400> SEQUENCE: 25

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 26
<211> LENGTH: 27
<212> TYPE: PRT
<213> ORGANISM: Homo sapiens

<400> SEQUENCE: 26

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 27
<211> LENGTH: 41
<212> TYPE: PRT
<213> ORGANISM: Homo sapiens

<400> SEQUENCE: 27

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 28
<211> LENGTH: 41
<212> TYPE: PRT
<213> ORGANISM: Homo sapiens

<400> SEQUENCE: 28

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 29
<211> LENGTH: 42
<212> TYPE: PRT
<213> ORGANISM: Homo sapiens

<400> SEQUENCE: 29

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 30
<211> LENGTH: 42
<212> TYPE: PRT
<213> ORGANISM: Homo sapiens

<400> SEQUENCE: 30

```
Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40
```

<210> SEQ ID NO 31
<211> LENGTH: 362
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

```
Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Lys Arg Gly
        195                 200                 205

Arg Lys Lys Leu Leu Tyr Ile Phe Lys Gln Pro Phe Met Arg Pro Val
    210                 215                 220

Gln Thr Thr Gln Glu Glu Asp Gly Cys Ser Cys Arg Phe Pro Glu Glu
225                 230                 235                 240

Glu Glu Gly Gly Cys Glu Leu Gly Gly Gly Arg Val Lys Phe Ser Arg
                245                 250                 255

Ser Ala Asp Ala Pro Ala Tyr Gln Gln Gly Gln Asn Gln Leu Tyr Asn
```

```
              260                 265                 270
Glu Leu Asn Leu Gly Arg Arg Glu Glu Tyr Asp Val Leu Asp Lys Arg
            275                 280                 285

Arg Gly Arg Asp Pro Glu Met Gly Gly Lys Pro Arg Arg Lys Asn Pro
        290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                    325                 330                 335

Asp Gly Leu Tyr Gln Gly Leu Ser Thr Ala Thr Lys Asp Thr Tyr Asp
                340                 345                 350

Ala Leu His Met Gln Ala Leu Pro Pro Arg
            355                 360

<210> SEQ ID NO 32
<211> LENGTH: 410
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Leu Leu Leu Val Thr Ser Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Phe Trp Val Leu Val Val Gly Gly Val
            180                 185                 190

Leu Ala Cys Tyr Ser Leu Leu Val Thr Val Ala Phe Ile Ile Phe Trp
        195                 200                 205

Val Arg Ser Lys Arg Ser Arg Gly Gly His Ser Asp Tyr Met Asn Met
210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser Gly Gly Gly Lys Arg Gly
                245                 250                 255
```

```
Arg Lys Lys Leu Leu Tyr Ile Phe Lys Gln Pro Phe Met Arg Pro Val
            260                 265                 270

Gln Thr Thr Gln Glu Glu Asp Gly Cys Ser Cys Arg Phe Pro Glu Glu
        275                 280                 285

Glu Glu Gly Gly Cys Glu Leu Gly Gly Gly Arg Val Lys Phe Ser Arg
    290                 295                 300

Ser Ala Asp Ala Pro Ala Tyr Gln Gln Gly Gln Asn Gln Leu Tyr Asn
305                 310                 315                 320

Glu Leu Asn Leu Gly Arg Arg Glu Glu Tyr Asp Val Leu Asp Lys Arg
                325                 330                 335

Arg Gly Arg Asp Pro Glu Met Gly Gly Lys Pro Arg Arg Lys Asn Pro
                340                 345                 350

Gln Glu Gly Leu Tyr Asn Glu Leu Gln Lys Asp Lys Met Ala Glu Ala
            355                 360                 365

Tyr Ser Glu Ile Gly Met Lys Gly Glu Arg Arg Arg Gly Lys Gly His
    370                 375                 380

Asp Gly Leu Tyr Gln Gly Leu Ser Thr Ala Thr Lys Asp Thr Tyr Asp
385                 390                 395                 400

Ala Leu His Met Gln Ala Leu Pro Pro Arg
                405                 410

<210> SEQ ID NO 33
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Leu Leu Leu Val Thr Ser Leu Leu Cys Glu Leu Pro His Pro
1               5                   10                  15

Ala Phe Leu Leu Ile Pro Gly Pro Val Pro Pro Ser Thr Ala Leu Arg
                20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
    130                 135                 140

Cys Pro Gly Gly Gly Ser Ser Gly Gly Gly Ser Gly Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190
```

```
Ile Ala Val Glu Trp Glu Ser Asn Gly Gln Pro Glu Asn Asn Tyr Lys
            195                 200                 205

Thr Thr Pro Pro Val Leu Asp Ser Asp Gly Ser Phe Phe Leu Tyr Ser
        210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly Lys Met Ala Leu Ile Val Leu Gly Gly Val
            260                 265                 270

Ala Gly Leu Leu Leu Phe Ile Gly Leu Gly Ile Phe Phe Lys Arg Gly
        275                 280                 285

Arg Lys Lys Leu Leu Tyr Ile Phe Lys Gln Pro Phe Met Arg Pro Val
290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Gly Gly Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
        355                 360                 365

Arg Gly Arg Asp Pro Glu Met Gly Gly Lys Pro Arg Arg Lys Asn Pro
    370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
        435                 440

<210> SEQ ID NO 34
<211> LENGTH: 541
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
```

-continued

```
               100                 105                 110
Val Ala Gln Phe Val Lys Asp Leu Leu His Leu Lys Lys Leu Phe
           115                 120                 125
Arg Glu Gly Arg Phe Asn Glu Ser Lys Tyr Gly Pro Pro Cys Pro Pro
           130                 135                 140
Cys Pro Ala Pro Glu Phe Glu Gly Gly Pro Ser Val Phe Leu Phe Pro
145                 150                 155                 160
Pro Lys Pro Lys Asp Thr Leu Met Ile Ser Arg Thr Pro Glu Val Thr
                   165                 170                 175
Cys Val Val Val Asp Val Ser Gln Glu Asp Pro Glu Val Gln Phe Asn
                   180                 185                 190
Trp Tyr Val Asp Gly Val Glu Val His Asn Ala Lys Thr Lys Pro Arg
               195                 200                 205
Glu Glu Gln Phe Gln Ser Thr Tyr Arg Val Val Ser Val Leu Thr Val
           210                 215                 220
Leu His Gln Asp Trp Leu Asn Gly Lys Glu Tyr Lys Cys Lys Val Ser
225                 230                 235                 240
Asn Lys Gly Leu Pro Ser Ser Ile Glu Lys Thr Ile Ser Lys Ala Lys
                   245                 250                 255
Gly Gln Pro Arg Glu Pro Gln Val Tyr Thr Leu Pro Pro Ser Gln Glu
                   260                 265                 270
Glu Met Thr Lys Asn Gln Val Ser Leu Thr Cys Leu Val Lys Gly Phe
               275                 280                 285
Tyr Pro Ser Asp Ile Ala Val Glu Trp Glu Ser Asn Gly Gln Pro Glu
           290                 295                 300
Asn Asn Tyr Lys Thr Thr Pro Pro Val Leu Asp Ser Asp Gly Ser Phe
305                 310                 315                 320
Phe Leu Tyr Ser Arg Leu Thr Val Asp Lys Ser Arg Trp Gln Glu Gly
                   325                 330                 335
Asn Val Phe Ser Cys Ser Val Met His Glu Ala Leu His Asn His Tyr
                   340                 345                 350
Thr Gln Lys Ser Leu Ser Leu Ser Leu Gly Lys Ile Tyr Ile Trp Ala
               355                 360                 365
Pro Leu Ala Gly Thr Cys Gly Val Leu Leu Leu Ser Leu Val Ile Thr
           370                 375                 380
Lys Arg Gly Arg Lys Lys Leu Leu Tyr Ile Phe Lys Gln Pro Phe Met
385                 390                 395                 400
Arg Pro Val Gln Thr Thr Gln Glu Glu Asp Gly Cys Ser Cys Arg Phe
                   405                 410                 415
Pro Glu Glu Glu Glu Gly Gly Cys Glu Leu Gly Gly Gly Arg Val Lys
                   420                 425                 430
Phe Ser Arg Ser Ala Asp Ala Pro Ala Tyr Gln Gln Gly Gln Asn Gln
               435                 440                 445
Leu Tyr Asn Glu Leu Asn Leu Gly Arg Arg Glu Glu Tyr Asp Val Leu
           450                 455                 460
Asp Lys Arg Arg Gly Arg Asp Pro Glu Met Gly Gly Lys Pro Arg Arg
465                 470                 475                 480
Lys Asn Pro Gln Glu Gly Leu Tyr Asn Glu Leu Gln Lys Asp Lys Met
                   485                 490                 495
Ala Glu Ala Tyr Ser Glu Ile Gly Met Lys Gly Glu Arg Arg Arg Gly
                   500                 505                 510
Lys Gly His Asp Gly Leu Tyr Gln Gly Leu Ser Thr Ala Thr Lys Asp
               515                 520                 525
```

Thr Tyr Asp Ala Leu His Met Gln Ala Leu Pro Pro Arg
            530                 535                 540

<210> SEQ ID NO 35
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
                20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Gly Gly Ser Ser Gly Gly Ser Gly
130                 135                 140

Met Phe Trp Val Leu Val Val Gly Gly Val Leu Ala Cys Tyr Ser
145                 150                 155                 160

Leu Leu Val Thr Val Ala Phe Ile Ile Phe Trp Val Arg Ser Lys Arg
                165                 170                 175

Ser Arg Gly Gly His Ser Asp Tyr Met Asn Met Thr Pro Arg Arg Pro
            180                 185                 190

Gly Pro Thr Arg Lys His Tyr Gln Pro Tyr Ala Pro Pro Arg Asp Phe
        195                 200                 205

Ala Ala Tyr Arg Ser Gly Gly Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Gly Cys
                245                 250                 255

Glu Leu Gly Gly Gly Arg Val Lys Phe Ser Arg Ser Ala Asp Ala Pro
            260                 265                 270

Ala Tyr Gln Gln Gly Gln Asn Gln Leu Tyr Asn Glu Leu Asn Leu Gly
        275                 280                 285

Arg Arg Glu Glu Tyr Asp Val Leu Asp Lys Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

```
Met Lys Gly Glu Arg Arg Gly Lys Gly His Asp Gly Leu Tyr Gln
                340                 345                 350

Gly Leu Ser Thr Ala Thr Lys Asp Thr Tyr Asp Ala Leu His Met Gln
            355                 360                 365

Ala Leu Pro Pro Arg
        370

<210> SEQ ID NO 36
<211> LENGTH: 385
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
    130                 135                 140

Cys Pro Gly Gly Gly Ser Ser Gly Gly Gly Ser Gly Met Phe Trp Val
145                 150                 155                 160

Leu Val Val Val Gly Gly Val Leu Ala Cys Tyr Ser Leu Leu Val Thr
                165                 170                 175

Val Ala Phe Ile Ile Phe Trp Val Arg Ser Lys Arg Ser Arg Gly Gly
            180                 185                 190

His Ser Asp Tyr Met Asn Met Thr Pro Arg Arg Pro Gly Pro Thr Arg
        195                 200                 205

Lys His Tyr Gln Pro Tyr Ala Pro Pro Arg Asp Phe Ala Ala Tyr Arg
    210                 215                 220

Ser Gly Gly Gly Lys Arg Gly Arg Lys Lys Leu Leu Tyr Ile Phe Lys
225                 230                 235                 240

Gln Pro Phe Met Arg Pro Val Gln Thr Thr Gln Glu Glu Asp Gly Cys
                245                 250                 255

Ser Cys Arg Phe Pro Glu Glu Glu Glu Gly Gly Cys Glu Leu Gly Gly
            260                 265                 270

Gly Arg Val Lys Phe Ser Arg Ser Ala Asp Ala Pro Ala Tyr Gln Gln
        275                 280                 285

Gly Gln Asn Gln Leu Tyr Asn Glu Leu Asn Leu Gly Arg Arg Glu Glu
    290                 295                 300

Tyr Asp Val Leu Asp Lys Arg Arg Gly Arg Asp Pro Glu Met Gly Gly
```

```
                305                 310                 315                 320
Lys Pro Arg Arg Lys Asn Pro Gln Glu Gly Leu Tyr Asn Glu Leu Gln
                    325                 330                 335

Lys Asp Lys Met Ala Glu Ala Tyr Ser Glu Ile Gly Met Lys Gly Glu
                340                 345                 350

Arg Arg Arg Gly Lys Gly His Asp Gly Leu Tyr Gln Gly Leu Ser Thr
                355                 360                 365

Ala Thr Lys Asp Thr Tyr Asp Ala Leu His Met Gln Ala Leu Pro Pro
            370                 375                 380

Arg
385

<210> SEQ ID NO 37
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
130                 135                 140

Cys Pro Gly Gly Gly Ser Gly Gly Gly Ser Gly Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
    210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly Lys Met Phe Trp Val Leu Val Val Val Gly
            260                 265                 270
```

```
Gly Val Leu Ala Cys Tyr Ser Leu Leu Val Thr Val Ala Phe Ile Ile
            275                 280                 285

Phe Trp Val Arg Ser Lys Arg Ser Arg Gly Gly His Ser Asp Tyr Met
290                 295                 300

Asn Met Thr Pro Arg Arg Pro Gly Pro Thr Arg Lys His Tyr Gln Pro
305                 310                 315                 320

Tyr Ala Pro Pro Arg Asp Phe Ala Ala Tyr Arg Ser Gly Gly Gly Lys
            325                 330                 335

Arg Gly Arg Lys Lys Leu Leu Tyr Ile Phe Lys Gln Pro Phe Met Arg
            340                 345                 350

Pro Val Gln Thr Thr Gln Glu Asp Gly Cys Ser Cys Arg Phe Pro
            355                 360                 365

Glu Glu Glu Glu Gly Gly Cys Glu Leu Gly Gly Gly Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 38
<211> LENGTH: 592
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Leu Leu Leu Val Thr Ser Leu Leu Cys Glu Leu Pro His Pro
1               5                   10                  15

Ala Phe Leu Leu Ile Pro Gly Pro Val Pro Ser Thr Ala Leu Arg
                20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
            115                 120                 125
```

-continued

```
Arg Glu Gly Arg Phe Asn Glu Ser Lys Tyr Gly Pro Pro Cys Pro Pro
    130                 135                 140

Cys Pro Ala Pro Glu Phe Glu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Gln Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350

Thr Gln Lys Ser Leu Ser Leu Ser Leu Gly Lys Met Phe Trp Val Leu
        355                 360                 365

Val Val Val Gly Gly Val Leu Ala Cys Tyr Ser Leu Leu Val Thr Val
    370                 375                 380

Ala Phe Ile Ile Phe Trp Val Arg Ser Lys Arg Ser Arg Gly Gly His
385                 390                 395                 400

Ser Asp Tyr Met Asn Met Thr Pro Arg Arg Pro Gly Pro Thr Arg Lys
                405                 410                 415

His Tyr Gln Pro Tyr Ala Pro Pro Arg Asp Phe Ala Ala Tyr Arg Ser
            420                 425                 430

Gly Gly Gly Lys Arg Gly Arg Lys Lys Leu Leu Tyr Ile Phe Lys Gln
        435                 440                 445

Pro Phe Met Arg Pro Val Gln Thr Thr Gln Glu Glu Asp Gly Cys Ser
    450                 455                 460

Cys Arg Phe Pro Glu Glu Glu Glu Gly Gly Cys Glu Leu Gly Gly Gly
465                 470                 475                 480

Arg Val Lys Phe Ser Arg Ser Ala Asp Ala Pro Ala Tyr Gln Gln Gly
                485                 490                 495

Gln Asn Gln Leu Tyr Asn Glu Leu Asn Leu Gly Arg Arg Glu Glu Tyr
            500                 505                 510

Asp Val Leu Asp Lys Arg Arg Gly Arg Asp Pro Glu Met Gly Gly Lys
        515                 520                 525

Pro Arg Arg Lys Asn Pro Gln Glu Gly Leu Tyr Asn Glu Leu Gln Lys
    530                 535                 540

Asp Lys Met Ala Glu Ala Tyr Ser Glu Ile Gly Met Lys Gly Glu Arg
```

Arg Arg Gly Lys Gly His Asp Gly Leu Tyr Gln Gly Leu Ser Thr Ala
545                 550                 555                 560

Thr Lys Asp Thr Tyr Asp Ala Leu His Met Gln Ala Leu Pro Pro Arg
            565                 570                 575

580                 585                 590

<210> SEQ ID NO 39
<211> LENGTH: 340
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gly Pro Val Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Ala Lys Pro Thr Thr Pro Ala Pro Arg Pro Thr Pro Ala Pro
        115                 120                 125

Thr Ile Ala Ser Gln Pro Leu Ser Leu Arg Pro Glu Ala Cys Arg Pro
    130                 135                 140

Ala Ala Gly Gly Ala Val His Thr Arg Gly Leu Asp Phe Ala Cys Asp
145                 150                 155                 160

Ile Tyr Ile Trp Ala Pro Leu Ala Gly Thr Cys Gly Val Leu Leu Leu
                165                 170                 175

Ser Leu Val Ile Thr Leu Tyr Lys Arg Gly Arg Lys Lys Leu Leu Tyr
            180                 185                 190

Ile Phe Lys Gln Pro Phe Met Arg Pro Val Gln Thr Thr Gln Glu Glu
        195                 200                 205

Asp Gly Cys Ser Cys Arg Phe Pro Glu Glu Glu Glu Gly Gly Cys Glu
    210                 215                 220

Leu Gly Gly Gly Arg Val Lys Phe Ser Arg Ser Ala Asp Ala Pro Ala
225                 230                 235                 240

Tyr Gln Gln Gly Gln Asn Gln Leu Tyr Asn Glu Leu Asn Leu Gly Arg
                245                 250                 255

Arg Glu Glu Tyr Asp Val Leu Asp Lys Arg Arg Gly Arg Asp Pro Glu
            260                 265                 270

Met Gly Gly Lys Pro Arg Arg Lys Asn Pro Gln Glu Gly Leu Tyr Asn
        275                 280                 285

Glu Leu Gln Lys Asp Lys Met Ala Glu Ala Tyr Ser Glu Ile Gly Met
    290                 295                 300

Lys Gly Glu Arg Arg Arg Gly Lys Gly His Asp Gly Leu Tyr Gln Gly
305                 310                 315                 320

Leu Ser Thr Ala Thr Lys Asp Thr Tyr Asp Ala Leu His Met Gln Ala
            325                 330                 335

Leu Pro Pro Arg
            340

<210> SEQ ID NO 40
<211> LENGTH: 388
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Ala Lys Pro Thr Thr Thr Pro Ala Pro Arg Pro Pro Thr Pro Ala Pro
        115                 120                 125

Thr Ile Ala Ser Gln Pro Leu Ser Leu Arg Pro Glu Ala Cys Arg Pro
    130                 135                 140

Ala Ala Gly Gly Ala Val His Thr Arg Gly Leu Asp Phe Ala Cys Asp
145                 150                 155                 160

Phe Trp Val Leu Val Val Val Gly Gly Val Leu Ala Cys Tyr Ser Leu
                165                 170                 175

Leu Val Thr Val Ala Phe Ile Ile Phe Trp Val Arg Ser Lys Arg Ser
            180                 185                 190

Arg Gly Gly His Ser Asp Tyr Met Asn Met Thr Pro Arg Arg Pro Gly
        195                 200                 205

Pro Thr Arg Lys His Tyr Gln Pro Tyr Ala Pro Pro Arg Asp Phe Ala
    210                 215                 220

Ala Tyr Arg Ser Gly Gly Gly Lys Arg Gly Arg Lys Lys Leu Leu Tyr
225                 230                 235                 240

Ile Phe Lys Gln Pro Phe Met Arg Pro Val Gln Thr Thr Gln Glu Glu
                245                 250                 255

Asp Gly Cys Ser Cys Arg Phe Pro Glu Glu Glu Glu Gly Gly Cys Glu
            260                 265                 270

Leu Gly Gly Gly Arg Val Lys Phe Ser Arg Ser Ala Asp Ala Pro Ala
        275                 280                 285

Tyr Gln Gln Gly Gln Asn Gln Leu Tyr Asn Glu Leu Asn Leu Gly Arg
    290                 295                 300

Arg Glu Glu Tyr Asp Val Leu Asp Lys Arg Arg Gly Arg Asp Pro Glu
305                 310                 315                 320

```
Met Gly Gly Lys Pro Arg Arg Lys Asn Pro Gln Glu Gly Leu Tyr Asn
            325                 330                 335

Glu Leu Gln Lys Asp Lys Met Ala Glu Ala Tyr Ser Glu Ile Gly Met
        340                 345                 350

Lys Gly Glu Arg Arg Arg Gly Lys Gly His Asp Gly Leu Tyr Gln Gly
    355                 360                 365

Leu Ser Thr Ala Thr Lys Asp Thr Tyr Asp Ala Leu His Met Gln Ala
370                 375                 380

Leu Pro Pro Arg
385

<210> SEQ ID NO 41
<211> LENGTH: 420
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Gly Gly Gly Ser
        115                 120                 125

Ser Gly Gly Gly Ser Gly Gly Gln Pro Arg Glu Pro Gln Val Tyr Thr
    130                 135                 140

Leu Pro Pro Ser Gln Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Arg Leu Thr Val Asp Lys
        195                 200                 205

Ser Arg Trp Gln Glu Gly Asn Val Phe Ser Cys Ser Val Met His Glu
    210                 215                 220

Ala Leu His Asn His Tyr Thr Gln Lys Ser Leu Ser Leu Ser Leu Gly
225                 230                 235                 240

Lys Met Ala Leu Ile Val Leu Gly Gly Val Ala Gly Leu Leu Leu Phe
                245                 250                 255

Ile Gly Leu Gly Ile Phe Phe Lys Arg Gly Arg Lys Lys Leu Leu Tyr
            260                 265                 270

Ile Phe Lys Gln Pro Phe Met Arg Pro Val Gln Thr Thr Gln Glu Glu
```

```
                 275                 280                 285

Asp Gly Cys Ser Cys Arg Phe Pro Glu Glu Glu Gly Gly Cys Glu
    290                 295                 300

Leu Gly Gly Gly Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
                340                 345                 350

Met Gly Gly Lys Pro Arg Arg Lys Asn Pro Gln Glu Gly Leu Tyr Asn
                355                 360                 365

Glu Leu Gln Lys Asp Lys Met Ala Glu Ala Tyr Ser Glu Ile Gly Met
    370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
                420

<210> SEQ ID NO 42
<211> LENGTH: 519
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gly Pro Val Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
                100                 105                 110

Glu Ser Lys Tyr Gly Pro Pro Cys Pro Pro Cys Pro Ala Pro Glu Phe
            115                 120                 125

Glu Gly Gly Pro Ser Val Phe Leu Phe Pro Pro Lys Pro Lys Asp Thr
        130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
                180                 185                 190

Thr Tyr Arg Val Val Ser Val Leu Thr Val Leu His Gln Asp Trp Leu
            195                 200                 205
```

```
Asn Gly Lys Glu Tyr Lys Cys Lys Val Ser Asn Lys Gly Leu Pro Ser
            210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
            245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
            275                 280                 285

Pro Pro Val Leu Asp Ser Asp Gly Ser Phe Phe Leu Tyr Ser Arg Leu
290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
            325                 330                 335

Leu Ser Leu Gly Lys Ile Tyr Ile Trp Ala Pro Leu Ala Gly Thr Cys
            340                 345                 350

Gly Val Leu Leu Leu Ser Leu Val Ile Thr Arg Gly Arg Lys Lys
            355                 360                 365

Leu Leu Tyr Ile Phe Lys Gln Pro Phe Met Arg Pro Val Gln Thr Thr
370                 375                 380

Gln Glu Glu Asp Gly Cys Ser Cys Arg Phe Pro Glu Glu Glu Glu Gly
385                 390                 395                 400

Gly Cys Glu Leu Gly Gly Arg Val Lys Phe Ser Arg Ser Ala Asp
            405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
            435                 440                 445

Asp Pro Glu Met Gly Gly Lys Pro Arg Arg Lys Asn Pro Gln Glu Gly
            450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
            485                 490                 495

Tyr Gln Gly Leu Ser Thr Ala Thr Lys Asp Thr Tyr Asp Ala Leu His
            500                 505                 510

Met Gln Ala Leu Pro Pro Arg
            515

<210> SEQ ID NO 43
<211> LENGTH: 351
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30
```

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
 50                  55                  60

Met Leu Ser Gly Phe Cys Pro His Lys Val Ser Ala Gly Gln Phe Ser
 65                  70                  75                  80

Ser Leu His Val Arg Asp Thr Lys Ile Glu Val Ala Gln Phe Val Lys
                 85                  90                  95

Asp Leu Leu His Leu Lys Lys Leu Phe Arg Glu Gly Arg Phe Asn
            100                 105                 110

Gly Gly Gly Ser Ser Gly Gly Ser Gly Met Phe Trp Val Leu Val
            115                 120                 125

Val Val Gly Gly Val Leu Ala Cys Tyr Ser Leu Leu Val Thr Val Ala
 130                 135                 140

Phe Ile Ile Phe Trp Val Arg Ser Lys Arg Ser Arg Gly Gly His Ser
145                 150                 155                 160

Asp Tyr Met Asn Met Thr Pro Arg Arg Pro Gly Pro Thr Arg Lys His
                165                 170                 175

Tyr Gln Pro Tyr Ala Pro Pro Arg Asp Phe Ala Ala Tyr Arg Ser Gly
            180                 185                 190

Gly Gly Lys Arg Gly Arg Lys Lys Leu Leu Tyr Ile Phe Lys Gln Pro
            195                 200                 205

Phe Met Arg Pro Val Gln Thr Thr Gln Glu Glu Asp Gly Cys Ser Cys
210                 215                 220

Arg Phe Pro Glu Glu Glu Glu Gly Gly Cys Glu Leu Gly Gly Gly Arg
225                 230                 235                 240

Val Lys Phe Ser Arg Ser Ala Asp Ala Pro Ala Tyr Gln Gln Gly Gln
                245                 250                 255

Asn Gln Leu Tyr Asn Glu Leu Asn Leu Gly Arg Arg Glu Glu Tyr Asp
            260                 265                 270

Val Leu Asp Lys Arg Arg Gly Arg Asp Pro Glu Met Gly Gly Lys Pro
            275                 280                 285

Arg Arg Lys Asn Pro Gln Glu Gly Leu Tyr Asn Glu Leu Gln Lys Asp
290                 295                 300

Lys Met Ala Glu Ala Tyr Ser Glu Ile Gly Met Lys Gly Glu Arg Arg
305                 310                 315                 320

Arg Gly Lys Gly His Asp Gly Leu Tyr Gln Gly Leu Ser Thr Ala Thr
                325                 330                 335

Lys Asp Thr Tyr Asp Ala Leu His Met Gln Ala Leu Pro Pro Arg
            340                 345                 350

<210> SEQ ID NO 44
<211> LENGTH: 363
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 44

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu

```
                35                  40                  45
Ser Leu Ile Asn Val Ser Gly Cys Ser Ala Ile Glu Lys Thr Gln Arg
 50                  55                  60

Met Leu Ser Gly Phe Cys Pro His Lys Val Ser Ala Gly Gln Phe Ser
 65                  70                  75                  80

Ser Leu His Val Arg Asp Thr Lys Ile Glu Val Ala Gln Phe Val Lys
                 85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Gly Gly Gly Ser
        115                 120                 125

Ser Gly Gly Gly Ser Gly Met Phe Trp Val Leu Val Val Val Gly Gly
    130                 135                 140

Val Leu Ala Cys Tyr Ser Leu Leu Val Thr Val Ala Phe Ile Ile Phe
145                 150                 155                 160

Trp Val Arg Ser Lys Arg Ser Arg Gly Gly His Ser Asp Tyr Met Asn
                165                 170                 175

Met Thr Pro Arg Arg Pro Gly Pro Thr Arg Lys His Tyr Gln Pro Tyr
            180                 185                 190

Ala Pro Pro Arg Asp Phe Ala Ala Tyr Arg Ser Gly Gly Gly Lys Arg
        195                 200                 205

Gly Arg Lys Lys Leu Leu Tyr Ile Phe Lys Gln Pro Phe Met Arg Pro
    210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Gly Gly Arg Val Lys Phe Ser
                245                 250                 255

Arg Ser Ala Asp Ala Pro Ala Tyr Gln Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
        355                 360

<210> SEQ ID NO 45
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gly Pro Val Pro Pro Ser Thr Ala Leu Arg Tyr Leu Ile Glu Glu Leu
 1               5                  10                  15

Val Asn Ile Thr Gln Asn Gln Lys Ala Pro Leu Cys Asn Gly Ser Met
                20                  25                  30
```

```
Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
50                      55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu His Leu Lys Lys Leu Phe Arg Glu Gly Arg Phe Asn
                100                 105                 110

Glu Ser Lys Tyr Gly Pro Pro Cys Pro Pro Cys Pro Gly Gly Ser
        115                 120                 125

Ser Gly Gly Gly Ser Gly Gly Gln Pro Arg Glu Pro Gln Val Tyr Thr
        130                 135                 140

Leu Pro Pro Ser Gln Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
        180                 185                 190

Asp Ser Asp Gly Ser Phe Phe Leu Tyr Ser Arg Leu Thr Val Asp Lys
        195                 200                 205

Ser Arg Trp Gln Glu Gly Asn Val Phe Ser Cys Ser Val Met His Glu
        210                 215                 220

Ala Leu His Asn His Tyr Thr Gln Lys Ser Leu Ser Leu Ser Leu Gly
225                 230                 235                 240

Lys Met Phe Trp Val Leu Val Val Val Gly Gly Val Leu Ala Cys Tyr
                245                 250                 255

Ser Leu Leu Val Thr Val Ala Phe Ile Ile Phe Trp Val Arg Ser Lys
                260                 265                 270

Arg Ser Arg Gly Gly His Ser Asp Tyr Met Asn Met Thr Pro Arg Arg
        275                 280                 285

Pro Gly Pro Thr Arg Lys His Tyr Gln Pro Tyr Ala Pro Pro Arg Asp
        290                 295                 300

Phe Ala Ala Tyr Arg Ser Gly Gly Gly Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
        340                 345                 350

Cys Glu Leu Gly Gly Gly Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
        370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
                420                 425                 430

Gly Met Lys Gly Glu Arg Arg Arg Gly Lys Gly His Asp Gly Leu Tyr
                435                 440                 445
```

```
Gln Gly Leu Ser Thr Ala Thr Lys Asp Thr Tyr Asp Ala Leu His Met
    450                 455                 460

Gln Ala Leu Pro Pro Arg
465             470

<210> SEQ ID NO 46
<211> LENGTH: 570
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

Glu Ser Lys Tyr Gly Pro Pro Cys Pro Pro Cys Pro Ala Pro Glu Phe
        115                 120                 125

Glu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
    290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
```

```
                    325                 330                 335
Leu Ser Leu Gly Lys Met Phe Trp Val Leu Val Val Gly Gly Val
                340                 345                 350
Leu Ala Cys Tyr Ser Leu Leu Val Thr Val Ala Phe Ile Ile Phe Trp
            355                 360                 365
Val Arg Ser Lys Arg Ser Arg Gly Gly His Ser Asp Tyr Met Asn Met
    370                 375                 380
Thr Pro Arg Arg Pro Gly Pro Thr Arg Lys His Tyr Gln Pro Tyr Ala
385                 390                 395                 400
Pro Pro Arg Asp Phe Ala Ala Tyr Arg Ser Gly Gly Lys Arg Gly
                405                 410                 415
Arg Lys Lys Leu Leu Tyr Ile Phe Lys Gln Pro Phe Met Arg Pro Val
            420                 425                 430
Gln Thr Thr Gln Glu Glu Asp Gly Cys Ser Cys Arg Phe Pro Glu Glu
        435                 440                 445
Glu Glu Gly Gly Cys Glu Leu Gly Gly Gly Arg Val Lys Phe Ser Arg
    450                 455                 460
Ser Ala Asp Ala Pro Ala Tyr Gln Gln Gly Gln Asn Gln Leu Tyr Asn
465                 470                 475                 480
Glu Leu Asn Leu Gly Arg Arg Glu Glu Tyr Asp Val Leu Asp Lys Arg
                485                 490                 495
Arg Gly Arg Asp Pro Glu Met Gly Gly Lys Pro Arg Arg Lys Asn Pro
            500                 505                 510
Gln Glu Gly Leu Tyr Asn Glu Leu Gln Lys Asp Lys Met Ala Glu Ala
        515                 520                 525
Tyr Ser Glu Ile Gly Met Lys Gly Glu Arg Arg Arg Gly Lys Gly His
    530                 535                 540
Asp Gly Leu Tyr Gln Gly Leu Ser Thr Ala Thr Lys Asp Thr Tyr Asp
545                 550                 555                 560
Ala Leu His Met Gln Ala Leu Pro Pro Arg
                565                 570

<210> SEQ ID NO 47
<211> LENGTH: 363
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Leu Leu Leu Val Thr Ser Leu Leu Leu Cys Glu Leu Pro His Pro
1               5                   10                  15
Ala Phe Leu Leu Ile Pro Gly Pro Val Pro Ser Thr Ala Leu Arg
                20                  25                  30
Tyr Leu Ile Glu Glu Leu Val Asn Ile Thr Gln Asn Gln Lys Ala Pro
            35                  40                  45
Leu Cys Asn Gly Ser Met Val Trp Ser Ile Asn Leu Thr Ala Gly Met
        50                  55                  60
Tyr Cys Ala Ala Leu Glu Ser Leu Ile Asn Val Ser Gly Cys Ser Ala
65                  70                  75                  80
Ile Glu Lys Thr Gln Arg Met Leu Ser Gly Phe Cys Pro His Lys Val
                85                  90                  95
Ser Ala Gly Gln Phe Ser Ser Leu His Val Arg Asp Thr Lys Ile Glu
            100                 105                 110
```

```
Val Ala Gln Phe Val Lys Asp Leu Leu His Leu Lys Lys Leu Phe
            115                 120                 125

Arg Glu Gly Arg Phe Asn Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Gly Gly Lys Arg
            195                 200                 205

Gly Arg Lys Lys Leu Leu Tyr Ile Phe Lys Gln Pro Phe Met Arg Pro
        210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Gly Gly Arg Val Lys Phe Ser
                245                 250                 255

Arg Ser Ala Asp Ala Pro Ala Tyr Gln Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
        290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
            355                 360

<210> SEQ ID NO 48
<211> LENGTH: 341
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gly Pro Val Pro Pro Ser Thr Ala Leu Arg Tyr Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95
```

```
Asp Leu Leu Leu His Leu Lys Lys Leu Phe Arg Glu Gly Arg Phe Asn
                100                 105                 110
Ala Lys Pro Thr Thr Thr Pro Ala Pro Arg Pro Pro Thr Pro Ala Pro
            115                 120                 125
Thr Ile Ala Ser Gln Pro Leu Ser Leu Arg Pro Glu Ala Cys Arg Pro
        130                 135                 140
Ala Ala Gly Gly Ala Val His Thr Arg Gly Leu Asp Phe Ala Cys Asp
145                 150                 155                 160
Ile Tyr Ile Trp Ala Pro Leu Ala Gly Thr Cys Gly Val Leu Leu Leu
                165                 170                 175
Ser Leu Val Ile Thr Gly Gly Lys Arg Gly Arg Lys Lys Leu Leu
            180                 185                 190
Tyr Ile Phe Lys Gln Pro Phe Met Arg Pro Val Gln Thr Thr Gln Glu
        195                 200                 205
Glu Asp Gly Cys Ser Cys Arg Phe Pro Glu Glu Glu Glu Gly Gly Cys
210                 215                 220
Glu Leu Gly Gly Gly Arg Val Lys Phe Ser Arg Ser Ala Asp Ala Pro
225                 230                 235                 240
Ala Tyr Gln Gln Gly Gln Asn Gln Leu Tyr Asn Glu Leu Asn Leu Gly
                245                 250                 255
Arg Arg Glu Glu Tyr Asp Val Leu Asp Lys Arg Arg Gly Arg Asp Pro
            260                 265                 270
Glu Met Gly Gly Lys Pro Arg Arg Lys Asn Pro Gln Glu Gly Leu Tyr
        275                 280                 285
Asn Glu Leu Gln Lys Asp Lys Met Ala Glu Ala Tyr Ser Glu Ile Gly
290                 295                 300
Met Lys Gly Glu Arg Arg Arg Gly Lys Gly His Asp Gly Leu Tyr Gln
305                 310                 315                 320
Gly Leu Ser Thr Ala Thr Lys Asp Thr Tyr Asp Ala Leu His Met Gln
                325                 330                 335
Ala Leu Pro Pro Arg
            340

<210> SEQ ID NO 49
<211> LENGTH: 112
<212> TYPE: PRT
<213> ORGANISM: Homo sapiens

<400> SEQUENCE: 49

Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 50
```

```
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 51
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Glu Ser Lys Tyr Gly Pro Pro Cys Pro Ser Cys Pro
1               5                   10

<210> SEQ ID NO 53
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys

```
225

<210> SEQ ID NO 54
<211> LENGTH: 28
<212> TYPE: PRT
<213> ORGANISM: Homo sapiens

<400> SEQUENCE: 54

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```